(12) United States Patent
Boone et al.

(10) Patent No.: US 8,221,749 B2
(45) Date of Patent: Jul. 17, 2012

(54) ANTIBODIES DIRECTED TO ANGIOPOIETIN-1 AND ANGIOPOIETIN-2 AND USES THEREOF

(75) Inventors: Thomas C. Boone, Newbury Park, CA (US); Jonathan D. Oliner, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/194,854

(22) Filed: Jul. 29, 2011

(65) Prior Publication Data

US 2012/0034237 A1 Feb. 9, 2012

Related U.S. Application Data

(62) Division of application No. 12/378,993, filed on Feb. 19, 2009, now Pat. No. 8,030,025.

(60) Provisional application No. 61/066,632, filed on Feb. 20, 2008, provisional application No. 61/061,943, filed on Jun. 16, 2008, provisional application No. 61/139,361, filed on Dec. 19, 2008.

(51) Int. Cl.
*A61K 39/395* (2006.01)

(52) U.S. Cl. ............... 424/130.1; 424/133.1; 424/138.1; 424/158.1; 530/350; 530/387.1; 530/387.3; 530/387.7; 530/388.23; 530/388.24

(58) Field of Classification Search ............... 424/130.1, 424/133.1, 138.1, 158.1; 530/350, 387.1, 530/387.3, 387.7, 388.23, 388.24
See application file for complete search history.

(56) References Cited

U.S. PATENT DOCUMENTS

| | | | |
|---|---|---|---|
| 4,816,567 A | 3/1989 | Cabilly et al. |
| 5,447,860 A | 9/1995 | Ziegler |
| 5,480,981 A | 1/1996 | Goodwin et al. |
| 5,521,073 A | 5/1996 | Davis et al. |
| 5,530,101 A | 6/1996 | Queen et al. |
| 5,545,807 A | 8/1996 | Surani et al. |
| 5,562,903 A | 10/1996 | Co et al. |
| 5,565,332 A | 10/1996 | Hoogenboom et al. |
| 5,585,089 A | 12/1996 | Queen et al. |
| 5,608,039 A | 3/1997 | Pastan et al. |
| 5,639,641 A | 6/1997 | Pedersen et al. |
| 5,643,755 A | 7/1997 | Davis et al. |
| 5,650,490 A | 7/1997 | Davis et al. |
| 5,681,722 A | 10/1997 | Newman et al. |
| 5,693,761 A | 12/1997 | Queen et al. |
| 5,693,762 A | 12/1997 | Queen et al. |
| 5,744,580 A | 4/1998 | Better et al. |
| 5,750,106 A | 5/1998 | Ostberg |
| 5,766,886 A | 6/1998 | Studnicka et al. |
| 5,770,196 A | 6/1998 | Studnicka |
| 5,773,218 A | 6/1998 | Gallatin et al. |
| 5,811,517 A | 9/1998 | Gallatin et al. |
| 5,814,464 A | 9/1998 | Davis et al. |
| 5,837,491 A | 11/1998 | Better et al. |
| 5,837,822 A | 11/1998 | Gallatin et al. |
| 5,859,205 A | 1/1999 | Adair et al. |
| 5,869,619 A | 2/1999 | Studnicka |
| 5,879,672 A | 3/1999 | Davis et al. |
| 5,885,793 A | 3/1999 | Griffiths et al. |
| 5,889,157 A | 3/1999 | Pastan et al. |
| 5,955,291 A | 9/1999 | Alitalo et al. |
| 5,972,338 A | 10/1999 | Godowski et al. |
| 5,977,319 A | 11/1999 | Pope et al. |
| 5,977,322 A | 11/1999 | Marks et al. |
| 5,981,726 A | 11/1999 | Pastan et al. |
| 6,030,831 A | 2/2000 | Godowski et al. |
| 6,046,310 A | 4/2000 | Queen et al. |
| 6,054,297 A | 4/2000 | Carter et al. |
| 6,072,035 A | 6/2000 | Hardman et al. |
| 6,146,629 A | 11/2000 | Dagan |
| 6,150,584 A | 11/2000 | Kucherlapati et al. |
| 6,166,185 A | 12/2000 | Davis et al. |
| 6,171,586 B1 | 1/2001 | Lam et al. |
| 6,287,562 B1 | 9/2001 | Pastan et al. |
| 6,300,064 B1 | 10/2001 | Knappik et al. |
| 6,455,035 B1 | 9/2002 | Sun et al. |
| 6,777,540 B1 | 8/2004 | Okumura et al. |
| 6,794,363 B2 | 9/2004 | Bejanin et al. |
| 6,924,360 B2 | 8/2005 | Green et al. |
| 7,067,131 B2 | 6/2006 | Gudas et al. |
| 7,074,571 B2 | 7/2006 | Bejanin et al. |
| 7,084,257 B2 | 8/2006 | Deshpande et al. |
| 7,090,844 B2 | 8/2006 | Bar-Eli et al. |
| 7,112,661 B1 | 9/2006 | Miller |
| 7,135,174 B2 | 11/2006 | Corvalan et al. |
| 7,138,501 B2 | 11/2006 | Ruben et al. |
| 7,147,851 B1 | 12/2006 | Ponath et al. |
| 7,179,892 B2 | 2/2007 | Basi et al. |

(Continued)

FOREIGN PATENT DOCUMENTS

CA 2375033 12/2000
(Continued)

OTHER PUBLICATIONS

Hu et al. (Curr. Oncol. Rep. Mar. 2009; 11 (2): 111-6; pp. 1-9).*
Coxon et al. (Mol. Cancer Ther. Oct. 2010; 9 (10): 2641-51).*
Brown et al. (Mol. Cancer Ther. Jan. 2010; 9 (1): 145-56).*
International Preliminary Report on Patentability, International Application No. PCT/US2007/001122, mailed Aug. 24, 2010.
Office Action, Australian Application No. 2005295260, mailed Jul. 12, 2010.
Office Action, Australian Application No. 2006228095, mailed Sep. 3, 2009.
Ahmad et al. (2001), "Differential Expression of Angiopoietin-1 and Angiopoietin-2 in Colon Carcinoma. A Possible Mechanism for the Installation of Angiogenesis," Cancer, vol. 92(5):1138-1143.
Ahmad et al., "The effects of angiopoietin-1 and -2 on tumor growth and angiogenesis in human colon cancer," Cancer Res., 61:1255-1259 (2001).
Barbas et al., "Assembly of combinatorial antibody libraries on phage surfaces: The gene III site," Proc Natl Acad Sci (USA) 88:7978-7982 (1991).

(Continued)

*Primary Examiner* — Stephen Rawlings
(74) *Attorney, Agent, or Firm* — Michael G. Penn

(57) ABSTRACT

Disclosed are specific binding agents, such as fully human antibodies, that bind to angiopoietin 1 and/or angiopoietin-2. Also disclosed are heavy chain fragments, light chain fragments, and CDRs of the antibodies, as well as methods of making and using the antibodies.

13 Claims, 11 Drawing Sheets

U.S. PATENT DOCUMENTS

| | | |
|---|---|---|
| 7,193,064 B2 | 3/2007 | Mikayama et al. |
| 7,193,069 B2 | 3/2007 | Isogai et al. |
| RE39,586 E | 4/2007 | Dagan |
| 7,220,840 B2 | 5/2007 | Ruben et al. |
| 7,241,444 B2 | 7/2007 | Goetsch et al. |
| 7,250,166 B2 | 7/2007 | Drakenberg et al. |
| 7,256,273 B2 | 8/2007 | Basi et al. |
| 7,262,028 B2 | 8/2007 | Van Berkel et al. |
| 7,521,053 B2 | 4/2009 | Oliner |
| 7,658,924 B2 | 2/2010 | Oliner et al. |
| 8,030,025 B2 | 10/2011 | Boone et al. |
| 2002/0048763 A1 | 4/2002 | Penn et al. |
| 2002/0146750 A1 | 10/2002 | Hoogenboom et al. |
| 2003/0054407 A1 | 3/2003 | Luo |
| 2003/0082177 A1 | 5/2003 | Kalish |
| 2003/0096226 A1 | 5/2003 | Logtenberg |
| 2003/0099647 A1 | 5/2003 | Deshpande et al. |
| 2003/0099655 A1 | 5/2003 | Watkins et al. |
| 2003/0124129 A1 | 7/2003 | Oliner |
| 2003/0161809 A1 | 8/2003 | Houston et al. |
| 2003/0194405 A1 | 10/2003 | Takeuchi et al. |
| 2003/0223994 A1 | 12/2003 | Hoogenboom et al. |
| 2004/0018198 A1 | 1/2004 | Gudas et al. |
| 2004/0058365 A1 | 3/2004 | Panzer et al. |
| 2004/0110933 A1 | 6/2004 | Rondon et al. |
| 2004/0151724 A1 | 8/2004 | Coronella-Wood |
| 2004/0219542 A1 | 11/2004 | Houston et al. |
| 2004/0253234 A1 | 12/2004 | Shitara et al. |
| 2004/0258699 A1 | 12/2004 | Bowdish et al. |
| 2005/0009136 A1 | 1/2005 | Nixon et al. |
| 2005/0013830 A1 | 1/2005 | Owens et al. |
| 2005/0026182 A1 | 2/2005 | Bejanin et al. |
| 2005/0031614 A1 | 2/2005 | Roskos et al. |
| 2005/0049402 A1 | 3/2005 | Babcook et al. |
| 2005/0053608 A1 | 3/2005 | Weber et al. |
| 2005/0054055 A1 | 3/2005 | Kucherlapati et al. |
| 2005/0058649 A1 | 3/2005 | Landes et al. |
| 2005/0084449 A1 | 4/2005 | Landes et al. |
| 2005/0095238 A1 | 5/2005 | Brettman et al. |
| 2005/0112698 A1 | 5/2005 | Neben et al. |
| 2005/0118651 A1 | 6/2005 | Basi et al. |
| 2005/0136055 A1 | 6/2005 | Gladue et al. |
| 2005/0169925 A1 | 8/2005 | Bardroff et al. |
| 2005/0175608 A1 | 8/2005 | Tamura et al. |
| 2005/0180977 A1 | 8/2005 | Nixon et al. |
| 2005/0221400 A1 | 10/2005 | Gudas et al. |
| 2005/0232917 A1 | 10/2005 | Pullen et al. |
| 2005/0249730 A1 | 11/2005 | Goetsch et al. |
| 2005/0260195 A1 | 11/2005 | Dagan et al. |
| 2005/0287630 A1 | 12/2005 | Kucherlapati et al. |
| 2005/0288864 A1 | 12/2005 | Cattaneo et al. |
| 2006/0018909 A1 | 1/2006 | Oliner et al. |
| 2006/0024297 A1 | 2/2006 | Wood et al. |
| 2006/0057138 A1 | 3/2006 | Wood et al. |
| 2006/0062783 A1 | 3/2006 | Roskos et al. |
| 2006/0063234 A1 | 3/2006 | Jones |
| 2006/0073148 A1 | 4/2006 | Tchistiakova et al. |
| 2006/0088883 A1 | 4/2006 | Smider et al. |
| 2006/0093600 A1 | 5/2006 | Bedian et al. |
| 2006/0099150 A1 | 5/2006 | Houston et al. |
| 2006/0121580 A1 | 6/2006 | Ter Meulen et al. |
| 2006/0134103 A1 | 6/2006 | Hawley et al. |
| 2006/0222643 A1 | 10/2006 | Tsunoda et al. |
| 2006/0235207 A1 | 10/2006 | Tsuchiya et al. |
| 2006/0246071 A1 | 11/2006 | Green et al. |
| 2006/0246077 A1 | 11/2006 | Bar-Eli et al. |
| 2006/0251668 A1 | 11/2006 | Goletz et al. |
| 2006/0275211 A1 | 12/2006 | Jakobovits et al. |
| 2006/0280743 A1 | 12/2006 | Basi et al. |
| 2006/0281072 A1 | 12/2006 | Bakker |
| 2007/0072177 A1 | 3/2007 | Bakker et al. |
| 2007/0098718 A1 | 5/2007 | Long et al. |
| 2007/0104715 A1 | 5/2007 | Nordstedt et al. |
| 2007/0154480 A1 | 7/2007 | Schenk |
| 2007/0190599 A1 | 8/2007 | Nakano et al. |
| 2008/0267971 A1 | 10/2008 | Green et al. |
| 2009/0149637 A1 | 6/2009 | Kucherlapati et al. |
| 2009/0191212 A1 | 7/2009 | Oliner et al. |
| 2010/0010202 A1 | 1/2010 | Kucherlapati et al. |

FOREIGN PATENT DOCUMENTS

| | | |
|---|---|---|
| EP | 0133988 | 3/1985 |
| EP | 0143949 | 6/1985 |
| EP | 0088046 | 12/1987 |
| EP | 0036676 B2 | 9/1990 |
| EP | 0528767 | 2/1993 |
| EP | 0592106 | 4/1994 |
| EP | 0546073 | 9/1997 |
| EP | 0873363 | 10/1998 |
| EP | 0957166 | 11/1999 |
| EP | 1051620 | 11/2000 |
| EP | 1071458 | 1/2001 |
| EP | 1130030 | 9/2001 |
| EP | 1245676 | 10/2002 |
| EP | 1303303 | 4/2003 |
| EP | 0058481 | 5/2003 |
| EP | 1422243 | 5/2004 |
| EP | 1438339 | 7/2004 |
| EP | 1461428 | 9/2004 |
| EP | 1466623 | 10/2004 |
| EP | 1478764 | 11/2004 |
| EP | 1479696 | 11/2004 |
| EP | 1508576 | 2/2005 |
| EP | 1539236 | 6/2005 |
| EP | 1554311 | 7/2005 |
| EP | 1680140 | 7/2006 |
| EP | 1693385 | 8/2006 |
| EP | 2272869 | 1/2011 |
| JP | 2005160485 | 12/1991 |
| JP | 06-153984 | 6/1994 |
| JP | 2000080100 | 3/2000 |
| JP | 2001507210 | 6/2001 |
| JP | 2001292787 | 10/2001 |
| JP | 2003531129 | 10/2003 |
| JP | 2004500847 | 1/2004 |
| JP | 2005500808 | 1/2005 |
| JP | 2005046143 | 2/2005 |
| WO | WO 90/04036 | 4/1990 |
| WO | WO 91/07492 | 5/1991 |
| WO | WO 93/11794 | 6/1993 |
| WO | WO 94/02602 | 2/1994 |
| WO | WO 95/13387 | 5/1995 |
| WO | WO 95/21866 | 8/1995 |
| WO | WO 96/13594 | 5/1996 |
| WO | WO 97/00271 | 1/1997 |
| WO | WO 97/08320 | 3/1997 |
| WO | WO 97/48418 | 12/1997 |
| WO | WO 98/05779 | 2/1998 |
| WO | WO 98/06248 | 2/1998 |
| WO | WO 98/18914 | 5/1998 |
| WO | WO 98/39027 | 9/1998 |
| WO | WO 99/10494 | 3/1999 |
| WO | WO 99/43801 | 9/1999 |
| WO | WO 99/45959 | 9/1999 |
| WO | WO 00/06195 | 2/2000 |
| WO | WO 00/23593 | 4/2000 |
| WO | WO 00/24782 | 5/2000 |
| WO | WO 00/26667 | 5/2000 |
| WO | WO 00/37504 | 6/2000 |
| WO | WO 00/57901 | 10/2000 |
| WO | WO 00/73430 | 12/2000 |
| WO | WO 00/75323 | 12/2000 |
| WO | WO 00/77037 | 12/2000 |
| WO | WO 01/27279 | 4/2001 |
| WO | WO 01/36642 | 5/2001 |
| WO | WO 01/57226 | 8/2001 |
| WO | WO 01/57276 | 8/2001 |
| WO | WO 01/78779 | 10/2001 |
| WO | WO 01/86003 | 11/2001 |
| WO | WO 01/87338 | 11/2001 |
| WO | WO 02/46237 | 6/2002 |
| WO | WO 02/059260 | 8/2002 |
| WO | WO 02/087611 | 11/2002 |
| WO | WO 03/002608 | 1/2003 |
| WO | WO 03/030833 | 4/2003 |

| | | |
|---|---|---|
| WO | WO 03/033674 | 4/2003 |
| WO | WO 03/046204 | 6/2003 |
| WO | WO 03/048321 | 6/2003 |
| WO | WO 03/057134 | 7/2003 |
| WO | WO 03/057251 | 7/2003 |
| WO | WO 03077858 | 9/2003 |
| WO | WO 2004/005890 | 1/2004 |
| WO | WO 2004/024098 | 3/2004 |
| WO | WO 2004/046306 | 6/2004 |
| WO | WO 2005/037235 | 4/2005 |
| WO | WO 2005/042578 | 5/2005 |
| WO | WO 2005/044294 | 5/2005 |
| WO | WO 2005/051998 | 6/2005 |
| WO | WO 2005/056601 | 6/2005 |
| WO | WO 2005/103083 | 11/2005 |
| WO | WO 2005/107784 | 11/2005 |
| WO | WO 2005/118644 | 12/2005 |
| WO | WO 2006/005367 | 1/2006 |
| WO | WO 2006/007850 | 1/2006 |
| WO | WO 2006/037604 | 4/2006 |
| WO | WO 2006/045049 | 4/2006 |
| WO | WO 2006/068953 | 6/2006 |
| WO | WO 2006/069202 | 6/2006 |
| WO | WO 2007/027713 | 3/2007 |
| WO | WO 2009/105269 | 8/2009 |

OTHER PUBLICATIONS

Bowie et al., "A Method to Identify Protein Sequences That Fold into a Known Three-Dimensional Stucture," Science, 253:164-170 (1991).
Brams et al., "Antigen-specific IgG responses from naive human splenocytes: in vitro priming followed by antigen boost in the SCID mouse," J Immunol, 160: 2051-2058 (1998).
Brenner et al., "Population statistics of protein structures: lessons from structural classifications," Curr. Op. Struct. Biol., 7(3):369-376 (1997).
Brodeur et al., "Mouse-Human Myeloma Partners for the Production of Heterohybridomas," Monoclonal Antibody Production Techniques and Applications, pp. 51-63, Marcel Dekker, Inc., New York, (1987).
Brorson et al. (1999), "Mutational analysis of avidity and fine specificity of anti-levan antibodies," Journal of Immunology, vol. 163:6694-6701.
Bruggemann et al., "Designer Mice: The production of human antibody repertoires in transgenic animals," Year in Immuno, 7: 33-40 (1993).
Bruggemann et al., "Strategies for expressions human antibody repertoires in transgenic mice," Immunol Today 17:391-7 (1996).
Brummell et al. (1993), "Probing the combining site of an anti-carbohydrate antibody by saturation-mutagenesis: role of the heavy-chain CDR3 residues," Biochemistry, vol. 32:1180-1187.
Bunone et al., "Expression of angiogenesis stimulators and inhibitors in human thyroid tumors and correlation with clinical pathological features," American Journal of Pathology, 155:1967-1976 (1999).
Burks et al. (1997), "In vitro scanning saturation mutagenesis of an antibody binding pocket," PNAS, vol. 94:412-417.
Capon et al., "Designing CD4 immunoadhesins for AIDS therapy," Nature, 337: 525-31 (1989).
Carballido et al., "Generation of primary antigen-specific human T- and B-cell responses in immunocompetent SCID-hu mice," Nat Med, 6: 103-106 (2000).
Casset et al. (2003), "A peptide mimetic of an anti-CD4 monoclonal antibody by rational design," Biochem and Biophysical Research Comms. 307, 198-205.
Chen et al. (1999), "Selection and analysis of an optimized anti-VEGF antibody: crystal structure of an affinity-matured Fab in complex with antigen," Journal of Molecular Biology, vol. 293:865-881.
Chothia et al., "Canonical structures for the hypervariable regions of immunoglobulins," J Mol Biol, 196: 901-17 (1987).
Chothia et al., "Conformations of immunoglobulin hypervariable regions," Nature, 342: 877-83 (1989).
Chou et al., "Conformational parameters for amino acids in helical, β-sheet, and random coil regions calculated from proteins," Biochemistry, 113(2):211-222 (1974).
Chou et al., "Empirical predictions of protein confirmation," Ann. Rev. Biochem., 47:251-276 (1978).
Chou et al., "Prediction of protein conformation," Biochemistry, 13(2):222-245 (1974).
Chou et al., "Prediction of the secondary structure of proteins from their amino acid sequence," Adv. Enzymol. Relat. Areas Mol. Biol., 47:45-148 (1978).
Chou et al., "Prediction of β-turns," Biophys. J., 26:367-384 (1979).
Chowdhury et al., Improving antibody affinity by mimicking somatic hypermutation in vitro,: Nature Biotech, 17: 568-572 (1999).
Co et al., "Genetically engineered deglycosylation of the variable domain increases the affinity of an anti-CD33 monoclonal antibody," Mol Immunol 30:1361-1367 (1993).
Cole et al., "The EBV-Hybridoma Technique and Its Appliction to Human Lung Cancer,"Monoclonal Antibodies and Cancer Therapy, Alan R Liss Inc, New York N.Y., pp. 77-96, (1985).
Colman, "Effects of amino acid sequence changes on antibody-antigen interactions," Research in Immunology, 145:33-36 (1994).
Connell et al., "Patent focus on cancer chemotherapeutics. III Angiogenesis agents: Oct. 2000-Mar. 2001," Expert Opinion on Therapeutic Patents, Ashley Publications Ltd. ISSN 1354-3776, pp. 1171-1203 (2001).
Cote et al., "Generation of human monoclonal antibodies reactive with cellular antigens," Proc Natl Acad Sci (USA) 80: 2026-2030 (1983).
Coxon et al., "Inhibition of interleukin-1 but not tumor necrosis factor suppresses neovascularization in rat models of corneal angiogenesis and adjuvant arthritis," Arthritis Rheum. 46:2604-2612 (2002).
Davis et al., "Isolation of Angiopoietin-1, a Ligand for the TIE2 Receptor, by Secretion-Trap Expression Cloning," Cell, 87:1161-1169 (1996).
Dayhoff et al., "A model of evolutionary change in proteins," Atlas of Protein Sequence and Structure, 5(3)345-352 (1978).
De Haard et al., "A large non-immunized human Fab fragment phage library that permits rapid isolation and kinetic analysis of high affinity antibodies," J Biol Chem (274) 18218-30 (1999).
Depascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., vol. 169: 3076-3084 (2002).
Dufner et al., "Harnessing phage and ribosome display for antibody optimization," Trends in Biotechnol., vol. 24(11):523-529 (2006).
Dumont et al., "Dominant-negative and targeted null mutations in the endothelial receptor tyrosine kinase, tek, reveal a critical role in vasculogenesis of the embryo," Genes & Development, 8:1897-1909 (1994).
Etoh et al., "Angiopoietin-2 is related to tumor angiogenesis in gastric carcinoma: possible in vivo regulation via induction of proteases," Cancer Research, 61:2145-2153 (2001).
Feige et al., "Anti-interleukin-1 and anti-tumor necrosis factor-a synergistically inhibit adjuvant arthritis in Lewis rats," Cell Mol. Life Sci. 57:1457-1470 (2000).
Folkman, J., "Angiogenesis in cancer, vascular, rheumatoid and other disease," Nat. Med., 1:27-31 (1995).
Gale et al., "Growth factors acting via endothelial cell-specific receptor tyrosine kinases: VEGFs, angiopoietins, and ephrins in vascular development," Genes Dev. 13:1055-1066 (1999).
Gilliland et al., "Elimination of the immunogenicity of therapeutic antibodies," J Immunol 62(6): 3663-71 (1999).
Gribskov et al., "Profile analysis," Meth. Enzym., 183:146-159 (1990).
Gribskov et al., "Profile analysis: Detection of distantly related proteins," Proc. Nat. Acad. Sci., 84(13):4355-4358 (1987).
Griffiths et al., "Human anti-self antibodies with high specificity from phage display libraries," EMBO J (12) 725-734 (1993).
Griffiths et al., "Isolation of high affinity human antibodies directly from large synthetic repertoires," EMBO J 13:3245-3260 (1994).
Grosios et al., "Assignment1 of ANGPT4, ANGPT1, and ANGPT2 encoding angiopoietins 4, 1 and 2 to human chromosome bands 20p13, 8q22.3 q23 and 8p23.1, respectively, by in situ hybridization and radiation hybrid mapping," Cytogenet Cell Genet, 84:118-120 (1999).

Hanahan, D., "Signaling vascular morphogenesis and maintenance," Science, 277:48-50 (1997).

Hangai et al., "Angiopoietin-1 upregulation by vascular endothelial growth factor in human retinal pigment epithelial cells," Investigative Ophthalmology & Visual Science, 42:1617-1625 (2001).

Henikoff et al., "Amino acid substitution matrices from protein blocks," Proc. Natl. Acad. Sci USA, 89:10915-10919 (1992).

Hodous et al., "Evolution of a highly selective and potent 2-(pyridin-2-yl)-1,3,5-triazine Tie-2 kinase inhibitor," J. Med. Chem 50:611-626 (2007).

Holash et al., "Vessel cooption, regression, and growth in tumors mediated by angiopoietins and VEGF," Science, 284:1994-1998 (1999).

Holm et al., "Functional mapping and single chain construction of the anti-cytokeratin 8 monoclonal antibody TS1," Mol. Immunology, vol. 44:1075-1084 (2007).

Holm et al., "Protein folds and families: sequence and structure alignments," Nucl. Acid. Res., 27(1):244-247 (1999).

Hoogenboom et al., "Human antibodies from synthetic repertoires of germline $V_H$ gene segments rearranged in vitro," J Mol Biol (227) 381-388 (1992).

Hoogenboom et al., "Multi-subunit proteins on the surface of filamentous phage: methodologies for displaying antibody (Fab) heavy and light chains," Nucl Acids Res 19:4133-4137 (1991).

Hudson, "Recombinant antibody fragments," Curr Opin Biotech, 9:395-402 (1998).

Ibragimova et al. (1999), "Stability of the β-sheet of the WW domain: A molecular dynamics simulation study," Biophysical Journal, vol. 77:2191-2198.

Ifversen et al., "SCID-hu-PBL: a model for making human antibodies," Sem Immunol 8:243-248 (1996).

Jakobovits et al., "Analysis of homozygous mutant chimeric mice: Deletion of the immunoglobulin heavy-chain joining region blocks B-cell development and antibody production," Proc Natl Acad Sci (USA), 90: 2551-2555 (1993).

Jakobovits et al., "Germ-line transmission and expression of a human-derived yeast artificial chromosome," Nature 362: 255-258 (1993).

Jang et al., "The structural basis for DNA binding by an anti-DNA autoantibody," Molecular Immunology, vol. 35:1207-1217 (1998).

Johnson et al., "Kabat Database and its applications: 30 years after the first variability plot," Nucleic Acids Res, 28: 214-8 (2000).

Jones et al., "Replacing the complementarity-determining regions in a human antibody with those from a mouse," Nature, vol. 321:522-525 (1986).

Jones, D., "Progress in protein structure prediction," Curr. Opin. Struct. Biol., 7(3):377-87 (1997).

Kabat et al., Sequences of Proteins of Immunological Interest, 5th ed., pp. iii-xi (1991) Table of Contents Only.

Kao et al., "Genetics of somatic mammalian cells. VII. Induction and isolation of nutritional mutants in Chinese hamster cells," Proc. Nat. Acad. Sci. 60: 1275-1281, (1968).

Kim, I. et al., "Angiopoietin-2 at high concentration can enhance endothelial cell survival through the phosphatidylinositol 3'-kinase/Akt signal transduction pathway," Oncogene 19(39): 4549-4552 (2000).

Kobayashi et al., "Tryptophan H33 plays an important role in pyrimidine (6-4) pyrimidone photoproduct binding by a high-affinity antibody," Protein Engineering, vol. 12:879-884 (1999).

Koblizek et al., "Angiopoietin-1 induces sprouting angiogenesis in vitro," Current Biology, 8:529-532 (1998).

Kohler et al., "Continuous cultures of fused cells secreting antibody of predefined specificity," Nature 256:495-497 (1975).

Kozbor et al., "The production of monoclonal antibodies from human lymphocytes," Immunol Today 4:72 (1983).

Kuroda, K., et al., "Altered expression of angiopoietins and Tie2 endothelium receptor in psoriasis," Journal of Investigative Dermatology, 116:713-720 (2001).

Kyte et al., "A simple method for displaying the hydropathic character of a protein," J. Mol. Biol., 157:105-131 (1982).

Lantto et al., "Chain shuffling to modify properties of recombinant immunoglobulins," Methods Mol. Biol. 178:303-16 (2002).

Lin et al., "Antiangiogenic gene therapy targeting the endothelium-specific receptor tyrosine kinase Tie2," Proc. Natl. Acad. Sci USA, 95:8829-8834 (1998).

Lin et al., "Inhibition of tumor angiogenesis using a soluble receptor establishes a role for Tie2 in pathologic vascular growth," J. Clin. Invest.,100:2072-2078 (1997).

Little et al., "Of mice and men: hybridoma and recombinant antibodies," Immunol Today 8:364-370 (2000).

MacCallum et al., "Antibody-antigen Interactions: Contact Analysis and Binding Site Topography," Journal of Molecular Biology, vol. 262:732-745 (1996).

Maisonpierre, et al., "Angiopoietin-2, a natural antagonist for Tie2 that disrupts in vivo angiogenesis," Science, 277:55-60 (1997).

Marks et al., "By-passing immunization," J Mol Biol 222: 581 (1991).

Martin et al., "Modeling antibody hypervariable loops: a combined algorithm," Proc Natl Acad Sci (USA) 86:9268-9272 (1989).

McCune et al., "A common PDGF receptor is activated by homodimeric A and B forms of PDGF," Science 241:1532-1639 (1988).

McLane et al., "Transplantation of a 17-amino acid alpha-helical DNA-binding domain into an antibody molecule confers sequence-dependent DNA recognition," PNAS USA vol. 92:5214-5218 (1995).

Mezquita, J., et al., "Characterization of a Novel Form of Angiopoietin-2 (Ang-2B) and Expression of VEGF and Angiopoietin-2 during Chicken Testicular Development and Regression," Biochemical and Biophysical Research Communications, 260:492-498 (1999).

Mosier et al., "Transfer of a functional human immune system to mice with severe combined immunodeficiency," Nature 335:256-259 (1988).

Moult J., "The current state of the art in protein structure prediction," Curr. Op. in Biotech., 7(4):422-427 (1996).

Mullinax et al., "Identification of human antibody fragment clones specific for tetanus toxoid in a bacteriophage lambda immunoexpression library," Proc Natl Acad Sci (USA) 87: 8095-8099 (1990).

Murphy et al., "Antibodies to CD40 prevent Epstein-Barr virus-mediated human B-cell lymphomagenesis in severe combined immune deficient mice given human peripheral blood lymphocytes," Blood 86:1946-1953 (1995).

Nachman et al., "Pseudodipeptide analogs of the pyrokinin/PBAN (FXPRLa) insect neuropeptide family containing carbocyclic Pro-mimetic conformational components," Regul Pept 57:359-370 (1995).

Needleman et al., "A general method applicable to the search for similarities in the amino acid sequence of two proteins," J. Mol. Biol., 48:443-453 (1970).

Ogoshi et al., "In situ hybridization analysis of the expression of human telomerase RNA in normal and pathologic conditions of the skin," J. Inv. Dermatol., 110:818-23 (1998).

Oliner et al., "Suppression of Angiogenesis and Tumor Growth by selective inhibition of angiopoietin-2," Cancer Cell, vol. 6(5):507-516 (2004).

Otani, A., et al., "Expressions of angiopoietins and Tie2 in human choroidal neovascular membranes," Investigative Ophthalmology & Visual Science, 40:1912-1920 (1999).

Papapetropoulos, A., et al., "Direct actions of angiopoietin-1 on human endothelium: evidence for network stabilization, cell survival, and interaction with other angiogenic growth factors," Lab Invest, 79:213-223 (1999).

Peacock et al., "Angiogenesis inhibition suppresses collagen arthritis," J. Exp. Med. 175:1135-1138 (1992).

Peacock et al. "A novel angiogenesis inhibitor suppresses rat adjuvant arthritis," Cell Immunol. 160:178-184 (1995).

Riechmann et al., "Reshaping human antibodies for therapy," Nature, 332: 323-327 (1988).

Roguska et al., "A comparison of two murine monoclonal antibodies humanized by CDR-grafting and variable domain resurfacing," Prot Engineer 9:895-904 (1996).

Rudikoff et al., "Single amino acid substitution altering antigen-binding specificity," PNAS, USA, vol. 79:1979-1983 (1982).

Saldanha et al., "A single backmutation in the human kIV framework of a previously unsuccessfully humanized antibody restores the binding activity and increases the secretion in cos cells," Mol Immunol 36:709-19 (1999).

Sato, T. N., et al., "Distinct roles of the receptor tyrosine kinases Tie-1 and Tie-2 in blood vessel formation," Nature, 376:70-74 (1995).

Shyu, KG et al., "Direct intramuscular injection of plasmid DNA encoding angiopoietin-1 but not angiopoietin-2 augments revascularization in the rabbit ischemic hindlimb," Circulation, 98:2081-2087 (1998).

Siemeister et al., "Two independent mechanisms essential for tumor angiogenesis inhibition of human melanoma xenograft growth by interfering with either the vascular endothelial growth factor receptor pathway or the Tie-2 pathway," Cancer Res., 59:3185-3189 (1999).

Sippl et al., "Threading thrills and threats," Structure, 4(1):15-19 (1996).

Smith et al., "Molecular Engineering of the Autographa californica Nuclear Polyhedrosis Virus Genome: Deletion Mutations Within the Polyhedrin Gene," J Virol 46: 584-593 (1983).

Smith et al., "Oxygen-induced retinopathy in the mouse," Invest. Ophthalmol Vis Sci 35: 101-111, (1994).

Stratmann, A., et al., "Cell type-specific expression of angiopoietin-1 and angiopoietin-2 suggests a role in glioblastoma angiogenesis," American Journal of Pathology, 153:1459-1466 (1998).

Suri, C., et al., "Increased vascularization in mice overexpressing angiopoietin-1," Science, 282:468-471 (1998).

Suri, C., et al., "Requisite Role of Angiopoietin-1, a Ligand for the TIE2 Receptor, during Embryonic Angiogenesis," Cell, 87:1171-1180 (1996).

Tam et al., "An SN2 deprotection of synthetic peptides with a low concentration of hydrofluoric acid in dimethyl sulfide: evidence and application in peptide synthesis," J Am Chem Soc, 105:6442-6455, (1983).

Tanaka, S., et al., "Biologic significance of angiopoietin-2 expression in human hepatocellular carcinoma," J Clin Invest, 103:341-345 (1999).

Teichert-Kuliszewska, K., P.C. Maisonpierre, et al., "Biological action of angiopoietin-2 in a fibrin matrix model of angiogenesis is associated with activation of Tie2," Cardiovascular Research 49(3): 659-70 (2001).

Vajdos et al., "Comprehensive functional maps of the antigen-binding site of an anti-ErbB2 antibody obtained with shotgun scanning mutagenesis," Journal of Molecular Biology, vol. 320:415-428 (2002).

Valenzuela et al., "Angiopoietins 3 and 4: diverging gene counterparts in mice and humans," Proceedings of the National Academy of Sciences of the USA, 96:1904-1909 (1999).

Vaswani et al., "Humanized antibodies as potential therapeutic drugs," Annals of Allergy, Asthma, & Immunol 81:105-115 (1998).

Vaughan TP et al., "Human Antibodies with Sub-nanomolar Affinities Isolated from a Large Non-immunized Phage Display Library," Nat Biotechnol (14) 309-314 (1996).

Verhoeyen et al., "Reshaping human antibodies: grafting an antilysozyme activity," Science 239:1534-1536 (1988).

Walsh et al., "Angiogenesis in the pathogenesis of inflammatory joint and lung diseases," Arthritis Res. 3:147-153 (2001).

Winter, "Synthetic human antibodies and a strategy for protein engineering," FEBS Letters 430:92-94 (1998).

Witzenbichler, B., et al., "Chemotactic Properties of Angiopoietin-1 and -2, Ligands for the Endothelial-specific Receptor Tyrosine Kinase Tie2," J Biol Chem, 273:18514-18521 (1998).

Wu et al., "Humanization of a murine monoclonal antibody by simultaneous optimization of framework and CDR residues," Journal of Molecular Biology, vol. 294:151-162 (1999).

Yang W-P. et al., "CDR Walking Mutagenesis for the Affinity Maturation of a Potent Human Anti-HIV-1 Antibody into the Picomolar Range," J Mol Biol (254) 392-403 (1995).

Yelton et al., "Affinity maturation of the BR96 anti-carcinoma antibody by codon-based mutagenesis," J Immunol (155) 1994-2004 (1995).

Yoshida, Y., et al.,"Expression of angiostatic factors in colorectal cancer," International Journal of Oncology, 15:1221-1225 (1999).

Yu et al., "Angiopoietin-2 is implicated in the regulation of tumor angiogenesis," Am. J. Path., 158:563-570 (2001).

Yuan, K., et al., "Expression of Tie-2, angiopoietin-1, angiopoietin-2, ephrinB2 and EphB4 in pyogenic granuloma of human gingiva implicates their roles in inflammatory angiogenesis," Journal of Periodontal Research, 35:165-171 (2000).

Zagzag et al., "In Situ Expression of Angiopoietins in Astrocytomas Identifies Angiopoietin-2 as an Early Marker of Tumor Angiogenesis," Experimental Neurology, 159:391-400 (1999).

* cited by examiner

FIGURE 1. Activity of Angiopoietin Antibodies in Colo205 Tumor Xenografts

FIGURE 2. Viable Tumor Burden of Angiopoietin Antibodies in Colo205 Tumor Xenografts p<0.0001 for all groups vs IgG2 control FIGURE 3. Effect of Anti-Ang-1 and/or Ang-2 Antibodies on Endothelial cell Proliferation *In Vivo*

FIGURE 4. Low Doses of H4L4 Inhibit Colo205 Tumor Growth

FIGURE 5. Low Doses of Antibody H4L4 Reduces Viable Tumor Burden

FIGURE 6. Effect of H4L4 on Colo205 Tumor Endothelial Cell Proliferation *In Vivo*

A.

B.

| Cardiac Appearance | Interpretation | Incidence n (%) | |
|---|---|---|---|
| | | Fc | mL4-3 |
| Normal size, many trabeculae | Normal | 9 (56%) | 0 |
| Normal size, mildly fewer trabeculae | Normal | 6 (38%) | 3 (20%) |
| Normal size, moderately fewer trabeculae | Normal | 0 | 1 (7%) |
| Reduced size, many fewer trabeculae | Abnormal | 1 (6%) | 11 (73%)* |
| | Total | 16 (100%) | 15 (100%) |

SEQUENCE LISTING

<160> NUMBER OF SEQ ID NOS: 48

<210> SEQ ID NO 1
<211> LENGTH: 122
<212> TYPE: PRT
<213> ORGANISM: Homo sapiens

<400> SEQUENCE: 1

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Tyr Trp
            100                 105                 110

Gly Gln Gly Thr Leu Val Thr Val Ser Ser
        115                 120

<210> SEQ ID NO 2
<211> LENGTH: 122
<212> TYPE: PRT
<213> ORGANISM: Homo sapiens

<400> SEQUENCE: 2

Glu Val Gln Leu Val Gln Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Gln Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Asp Tyr Asp Ile Leu Thr Gly Tyr Gly Tyr Trp
                100                 105                 110

Gly Gln Gly Thr Leu Val Thr Val Ser Ser
                115                 120

<210> SEQ ID NO 3
<211> LENGTH: 122
<212> TYPE: PRT
<213> ORGANISM: Homo sapiens

<400> SEQUENCE: 3

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Asp Tyr Asp Leu Leu Thr Gly Tyr Gly Tyr Trp
                100                 105                 110

Gly Gln Gly Thr Leu Val Thr Val Ser Ser
                115                 120

<210> SEQ ID NO 4
<211> LENGTH: 122
<212> TYPE: PRT
<213> ORGANISM: Homo sapiens

<400> SEQUENCE: 4

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Arg Asp Leu Leu Asp Tyr Asp Ile Tyr Thr Gly Tyr Gly Tyr Trp
            100                 105                 110

Gly Gln Gly Thr Leu Val Thr Val Ser Ser
            115                 120

<210> SEQ ID NO 5
<211> LENGTH: 122
<212> TYPE: PRT
<213> ORGANISM: Homo sapiens

<400> SEQUENCE: 5

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Leu Trp
            100                 105                 110

Gly Gln Gly Thr Leu Val Thr Val Ser Ser
            115                 120

<210> SEQ ID NO 6
<211> LENGTH: 122
<212> TYPE: PRT
<213> ORGANISM: Homo sapiens

<400> SEQUENCE: 6

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Met Trp
            100                 105                 110

Gly Gln Gly Thr Leu Val Thr Val Ser Ser
            115                 120

<210> SEQ ID NO 7
<211> LENGTH: 122
<212> TYPE: PRT
<213> ORGANISM: Homo sapiens

<400> SEQUENCE: 7

Glu Val Gln Leu Val Gln Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Trp Thr Gly Tyr Gly Tyr Trp
            100                 105                 110

Gly Gln Gly Thr Leu Val Thr Val Ser Ser
            115                 120

<210> SEQ ID NO 8
<211> LENGTH: 112
<212> TYPE: PRT
<213> ORGANISM: Homo sapiens

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ile Gln Ser Leu Leu Gln Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

<210> SEQ ID NO 9
<211> LENGTH: 112
<212> TYPE: PRT
<213> ORGANISM: Homo sapiens

<400> SEQUENCE: 9

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Leu Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110
```

<210> SEQ ID NO 10
<211> LENGTH: 112
<212> TYPE: PRT
<213> ORGANISM: Homo sapiens

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

<210> SEQ ID NO 11
<211> LENGTH: 112
<212> TYPE: PRT
<213> ORGANISM: Homo sapiens

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Val Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110

<210> SEQ ID NO 12
<211> LENGTH: 112
<212> TYPE: PRT
<213> ORGANISM: Homo sapiens

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Pro Thr Phe Gly Gln Gly Thr Lys Leu Glu Ile Lys
            100                 105                 110

<210> SEQ ID NO 13
<211> LENGTH: 112
<212> TYPE: PRT
<213> ORGANISM: Homo sapiens

<400> SEQUENCE: 13

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Met Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Pro Thr Phe Gly Gln Gly Thr Lys Leu Glu Ile Lys
            100                 105                 110

<210> SEQ ID NO 14
<211> LENGTH: 112
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Ala Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr His Trp Pro Pro Thr Phe Gly Gln Gly Thr Lys Leu Glu Ile Lys
            100                 105                 110

<210> SEQ ID NO 15
<211> LENGTH: 112
<212> TYPE: PRT
<213> ORGANISM: Homo sapiens

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser

```
            35                  40                  45
Pro Gln Leu Leu Ile Tyr Leu Gly Ser Asp Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Thr Phe Gly Gln Gly Thr Lys Leu Glu Ile Lys
            100                 105                 110
```

<210> SEQ ID NO 16
<211> LENGTH: 112
<212> TYPE: PRT
<213> ORGANISM: Homo sapiens

<400> SEQUENCE: 16

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr His Trp Pro Pro Thr Phe Gly Gln Gly Thr Lys Leu Glu Ile Lys
            100                 105                 110
```

<210> SEQ ID NO 17
<211> LENGTH: 112
<212> TYPE: PRT
<213> ORGANISM: Homo sapiens

<400> SEQUENCE: 17

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Val
                 85                  90                  95

Thr His Trp Pro Pro Thr Phe Gly Gln Gly Thr Lys Leu Glu Ile Lys
            100                 105                 110
```

<210> SEQ ID NO 18
<211> LENGTH: 5
<212> TYPE: PRT
<213> ORGANISM: Homo sapiens

<400> SEQUENCE: 18

```
Ser Tyr Gly Met His
1               5
```

<210> SEQ ID NO 19
<211> LENGTH: 16
<212> TYPE: PRT
<213> ORGANISM: Homo sapiens

<400> SEQUENCE: 19

```
Arg Ser Ser Gln Ser Leu Leu His Ser Asn Gly Tyr Asn Phe Leu Asp
1               5                   10                  15
```

<210> SEQ ID NO 20
<211> LENGTH: 16
<212> TYPE: PRT
<213> ORGANISM: Homo sapiens

<400> SEQUENCE: 20

```
Arg Ser Ser Gln Ser Leu Leu His Ser Asn Gly Tyr Asn Tyr Leu Asp
1               5                   10                  15
```

<210> SEQ ID NO 21
<211> LENGTH: 16
<212> TYPE: PRT
<213> ORGANISM: Homo sapiens

<400> SEQUENCE: 21

```
Arg Ser Ser Gln Ser Leu Leu His Ser Val Gly Tyr Asn Tyr Leu Asp
1               5                   10                  15
```

<210> SEQ ID NO 22
<211> LENGTH: 16
<212> TYPE: PRT
<213> ORGANISM: Homo sapiens

<400> SEQUENCE: 22

```
Arg Ser Ser Gln Ser Leu Leu His Ser Asn Gly Tyr Asn Met Leu Asp
1               5                   10                  15
```

<210> SEQ ID NO 23
<211> LENGTH: 16
<212> TYPE: PRT
<213> ORGANISM: Homo sapiens

<400> SEQUENCE: 23

```
Arg Ser Ser Gln Ser Leu Leu His Ser His Gly Tyr Asn Tyr Leu Asp
1               5                   10                  15
```

<210> SEQ ID NO 24
<211> LENGTH: 16
<212> TYPE: PRT
<213> ORGANISM: Homo sapiens

<400> SEQUENCE: 24

```
Arg Ser Ser Gln Ser Leu Leu Leu Ser Asn Gly Tyr Asn Tyr Leu Asp
1               5                   10                  15
```

<210> SEQ ID NO 25
<211> LENGTH: 16
<212> TYPE: PRT
<213> ORGANISM: Homo sapiens

<400> SEQUENCE: 25

```
Arg Ser Ile Gln Ser Leu Leu Gln Ser Asn Gly Tyr Asn Tyr Leu Asp
1               5                   10                  15
```

```
<210> SEQ ID NO 26
<211> LENGTH: 17
<212> TYPE: PRT
<213> ORGANISM: Homo sapiens

<400> SEQUENCE: 26

Tyr Ile Ser Ser Ser Gly Ser Thr Ile Tyr Tyr Ala Asp Ser Val Lys
1               5                   10                  15
Gly

<210> SEQ ID NO 27
<211> LENGTH: 7
<212> TYPE: PRT
<213> ORGANISM: Homo sapiens

<400> SEQUENCE: 27

Leu Gly Ser Asn Arg Ala Ser
1               5

<210> SEQ ID NO 28
<211> LENGTH: 17
<212> TYPE: PRT
<213> ORGANISM: Homo sapiens

<400> SEQUENCE: 28

Tyr Ile Ser Ser Ser Gly Ser Thr Ile Glu Tyr Ala Asp Ser Val Lys
1               5                   10                  15
Gly

<210> SEQ ID NO 29
<211> LENGTH: 17
<212> TYPE: PRT
<213> ORGANISM: Homo sapiens

<400> SEQUENCE: 29

Tyr Ile Ser Ser Ser Gly Ser Thr Ile Gln Tyr Ala Asp Ser Val Lys
1               5                   10                  15
Gly

<210> SEQ ID NO 30
<211> LENGTH: 7
<212> TYPE: PRT
<213> ORGANISM: Homo sapiens

<400> SEQUENCE: 30

Leu Gly Ser Asp Arg Ala Ser
1               5

<210> SEQ ID NO 31
<211> LENGTH: 7
<212> TYPE: PRT
<213> ORGANISM: Homo sapiens

<400> SEQUENCE: 31

Ala Gly Ser Asn Arg Ala Ser
1               5

<210> SEQ ID NO 32
<211> LENGTH: 13
<212> TYPE: PRT
<213> ORGANISM: Homo sapiens

<400> SEQUENCE: 32
```

-continued

Asp Leu Leu Asp Tyr Asp Ile Tyr Thr Gly Tyr Gly Tyr
1               5                   10

<210> SEQ ID NO 33
<211> LENGTH: 9
<212> TYPE: PRT
<213> ORGANISM: Homo sapiens

<400> SEQUENCE: 33

Met Gln Gly Thr His Trp Pro Pro Thr
1               5

<210> SEQ ID NO 34
<211> LENGTH: 13
<212> TYPE: PRT
<213> ORGANISM: Homo sapiens

<400> SEQUENCE: 34

Asp Leu Leu Asp Tyr Asp Ile Trp Thr Gly Tyr Gly Tyr
1               5                   10

<210> SEQ ID NO 35
<211> LENGTH: 13
<212> TYPE: PRT
<213> ORGANISM: Homo sapiens

<400> SEQUENCE: 35

Asp Leu Leu Asp Tyr Asp Leu Leu Thr Gly Tyr Gly Tyr
1               5                   10

<210> SEQ ID NO 36
<211> LENGTH: 9
<212> TYPE: PRT
<213> ORGANISM: Homo sapiens

<400> SEQUENCE: 36

Met Gln Val Thr His Trp Pro Pro Thr
1               5

<210> SEQ ID NO 37
<211> LENGTH: 13
<212> TYPE: PRT
<213> ORGANISM: Homo sapiens

<400> SEQUENCE: 37

Asp Leu Leu Asp Tyr Asp Ile Leu Thr Gly Met Gly Tyr
1               5                   10

<210> SEQ ID NO 38
<211> LENGTH: 13
<212> TYPE: PRT
<213> ORGANISM: Homo sapiens

<400> SEQUENCE: 38

Asp Leu Leu Asp Tyr Asp Ile Leu Thr Gly Leu Gly Tyr
1               5                   10

<210> SEQ ID NO 39
<211> LENGTH: 13
<212> TYPE: PRT
<213> ORGANISM: Homo sapiens

<400> SEQUENCE: 39

Asp Leu Leu Asp Tyr Asp Ile Leu Thr Gly Tyr Gly Tyr
1               5                   10

<210> SEQ ID NO 40
<211> LENGTH: 9
<212> TYPE: PRT
<213> ORGANISM: Homo sapiens

<400> SEQUENCE: 40

Met Gln Ala Thr His Trp Pro Pro Thr
1               5

<210> SEQ ID NO 41
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 41

| | | | | | | | | | | | | | | | | |
|---|---|---|---|---|---|---|---|---|---|---|---|---|---|---|---|---|
| gct | agc | acc | aag | ggc | cca | tcg | gtc | ttc | ccc | ctg | gcg | ccc | tgc | tcc | agg | 48 |
| Ala | Ser | Thr | Lys | Gly | Pro | Ser | Val | Phe | Pro | Leu | Ala | Pro | Cys | Ser | Arg | |
| 1 | | | | 5 | | | | | 10 | | | | | 15 | | |
| agc | acc | tcc | gag | agc | aca | gcg | gcc | ctg | ggc | tgc | ctg | gtc | aag | gac | tac | 96 |
| Ser | Thr | Ser | Glu | Ser | Thr | Ala | Ala | Leu | Gly | Cys | Leu | Val | Lys | Asp | Tyr | |
| | | 20 | | | | | 25 | | | | | 30 | | | | |
| ttc | ccc | gaa | ccg | gtg | acg | gtg | tcg | tgg | aac | tca | ggc | gct | ctg | acc | agc | 144 |
| Phe | Pro | Glu | Pro | Val | Thr | Val | Ser | Trp | Asn | Ser | Gly | Ala | Leu | Thr | Ser | |
| | 35 | | | | | 40 | | | | | 45 | | | | | |
| ggc | gtg | cac | acc | ttc | cca | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| 50 | | | | | 55 | | | | | 60 | | | | | | |
| ctc | agc | agc | gtg | gtg | acc | gtg | ccc | tcc | agc | aac | ttc | ggc | acc | cag | acc | 240 |
| Leu | Ser | Ser | Val | Val | Thr | Val | Pro | Ser | Ser | Asn | Phe | Gly | Thr | Gln | Thr | |
| 65 | | | | 70 | | | | | 75 | | | | | 80 | | |
| tac | acc | tgc | aac | gta | gat | cac | aag | ccc | agc | aac | acc | aag | gtg | gac | aag | 288 |
| Tyr | Thr | Cys | Asn | Val | Asp | His | Lys | Pro | Ser | Asn | Thr | Lys | Val | Asp | Lys | |
| | | | 85 | | | | | 90 | | | | | 95 | | | |
| aca | gtt | gag | cgc | aaa | tgt | tgt | gtc | gag | tgc | cca | ccg | tgc | cca | gca | cca | 336 |
| Thr | Val | Glu | Arg | Lys | Cys | Cys | Val | Glu | Cys | Pro | Pro | Cys | Pro | Ala | Pro | |
| | | | 100 | | | | | 105 | | | | | 110 | | | |
| cct | gtg | gca | gga | ccg | tca | gtc | ttc | ctc | ttc | ccc | cca | aaa | ccc | aag | gac | 384 |
| Pro | Val | Ala | Gly | Pro | Ser | Val | Phe | Leu | Phe | Pro | Pro | Lys | Pro | Lys | Asp | |
| | | 115 | | | | | 120 | | | | | 125 | | | | |
| acc | ctc | atg | atc | tcc | cgg | acc | cct | gag | gtc | acg | tgc | gtg | gtg | gtg | gac | 432 |
| Thr | Leu | Met | Ile | Ser | Arg | Thr | Pro | Glu | Val | Thr | Cys | Val | Val | Val | Asp | |
| | 130 | | | | | 135 | | | | | 140 | | | | | |
| gtg | agc | cac | gaa | gac | ccc | gag | gtc | cag | ttc | aac | tgg | tac | gtg | gac | ggc | 480 |
| Val | Ser | His | Glu | Asp | Pro | Glu | Val | Gln | Phe | Asn | Trp | Tyr | Val | Asp | Gly | |
| 145 | | | | | 150 | | | | | 155 | | | | | 160 | |
| gtg | gag | gtg | cat | aat | gcc | aag | aca | aag | cca | cgg | gag | gag | cag | ttc | aac | 528 |
| Val | Glu | Val | His | Asn | Ala | Lys | Thr | Lys | Pro | Arg | Glu | Glu | Gln | Phe | Asn | |
| | | | 165 | | | | | 170 | | | | | 175 | | | |
| agc | acg | ttc | cgt | gtg | gtc | agc | gtc | ctc | acc | gtt | gtg | cac | cag | gac | tgg | 576 |
| Ser | Thr | Phe | Arg | Val | Val | Ser | Val | Leu | Thr | Val | Val | His | Gln | Asp | Trp | |
| | | 180 | | | | | 185 | | | | | 190 | | | | |
| ctg | aac | ggc | aag | gag | tac | aag | tgc | aag | gtc | tcc | aac | aaa | ggc | ctc | cca | 624 |
| Leu | Asn | Gly | Lys | Glu | Tyr | Lys | Cys | Lys | Val | Ser | Asn | Lys | Gly | Leu | Pro | |
| | 195 | | | | | 200 | | | | | 205 | | | | | |
| gcc | ccc | atc | gag | aaa | acc | atc | tcc | aaa | acc | aaa | ggg | cag | ccc | cga | gaa | 672 |
| Ala | Pro | Ile | Glu | Lys | Thr | Ile | Ser | Lys | Thr | Lys | Gly | Gln | Pro | Arg | Glu | |
| 210 | | | | | 215 | | | | | 220 | | | | | | |
| cca | cag | gtg | tac | acc | ctg | ccc | cca | tcc | cgg | gag | gag | atg | acc | aag | aac | 720 |
| Pro | Gln | Val | Tyr | Thr | Leu | Pro | Pro | Ser | Arg | Glu | Glu | Met | Thr | Lys | Asn | |

```
                    225                 230                 235                 240
cag gtc agc ctg acc tgc ctg gtc aaa ggc ttc tac ccc agc gac atc       768
Gln Val Ser Leu Thr Cys Leu Val Lys Gly Phe Tyr Pro Ser Asp Ile
                245                 250                 255 gcc gtg gag tgg gag agc aat ggg cag ccg gag aac aac tac aag acc       816
Ala Val Glu Trp Glu Ser Asn Gly Gln Pro Glu Asn Asn Tyr Lys Thr
            260                 265                 270 aca cct ccc atg ctg gac tcc gac ggc tcc ttc ttc ctc tac agc aag       864
Thr Pro Pro Met Leu Asp Ser Asp Gly Ser Phe Phe Leu Tyr Ser Lys
        275                 280                 285 ctc acc gtg gac aag agc agg tgg cag cag ggg aac gtc ttc tca tgc       912
Leu Thr Val Asp Lys Ser Arg Trp Gln Gln Gly Asn Val Phe Ser Cys
    290                 295                 300 tcc gtg atg cat gag gct ctg cac aac cac tac acg cag aag agc ctc       960
Ser Val Met His Glu Ala Leu His Asn His Tyr Thr Gln Lys Ser Leu
305                 310                 315                 320 tcc ctg tct ccg ggt aaa tga                                           981
Ser Leu Ser Pro Gly Lys
                325

<210> SEQ ID NO 42
<211> LENGTH: 326
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
```

```
                245                 250                 255
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 43
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 43 cgt acg gtg gct gca cca tct gtc ttc atc ttc ccg cca tct gat gag        48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc        96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa       144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc       192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag       240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg       288
Lys His Lys Val Tyr Ala Cys Glu Val Thr His Gln Gly Leu Ser Ser
                85                  90                  95 ccc gtc aca aag agc ttc aac agg gga gag tgt tag                       324
Pro Val Thr Lys Ser Phe Asn Arg Gly Glu Cys
            100                 105

<210> SEQ ID NO 44
<211> LENGTH: 107
<212> TYPE: PRT
<213> ORGANISM: Homo sapiens

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

```
                     85                  90                  95
Pro Val Thr Lys Ser Phe Asn Arg Gly Glu Cys
                100                 105

<210> SEQ ID NO 45
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 45 ggc caa ccg aaa gcg gcg ccc tcg gtc act ctg ttc ccg ccc tcc tct      48
Gly Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac      96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc     144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac     192
Val Lys Ala Gly Val Glu Thr Thr Thr Pro Ser Lys Gln Ser Asn Asn
    50                  55                  60 aag tac gcg gcc agc agc tat ctg agc ctg acg cct gag cag tgg aag     240
Lys Tyr Ala Ala Ser Ser Tyr Leu Ser Leu Thr Pro Glu Gln Trp Lys
65                  70                  75                  80 tcc cac aga agc tac agc tgc cag gtc acg cat gaa ggg agc acc gtg     288
Ser His Arg Ser Tyr Ser Cys Gln Val Thr His Glu Gly Ser Thr Val
                85                  90                  95 gag aag aca gtg gcc cct aca gaa tgt tca tag                         321
Glu Lys Thr Val Ala Pro Thr Glu Cys Ser
            100                 105

<210> SEQ ID NO 46
<211> LENGTH: 106
<212> TYPE: PRT
<213> ORGANISM: Homo sapiens

<400> SEQUENCE: 46

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 47
<211> LENGTH: 72
<212> TYPE: PRT
<213> ORGANISM: Homo sapiens

<400> SEQUENCE: 47
```

```
Met Arg Glu Trp Thr Glu Met Gln Val Ile Phe Asp Ala Met Met
1               5                   10                  15

Phe Gly Pro Arg Asn Asp Arg Gly Gly Ser Gly Ser Ala Thr Gly Ser
                20                  25                  30

Gly Ser Thr Ala Ser Ser Gly Ser Gly Ser Ala Thr His Arg Glu Trp
                35                  40                  45

Thr Glu Glu Met Gln Val Ile Phe Asp Ala Met Met Phe Gly Pro Arg
                50                  55                  60

Asn Asp Arg Gly Gly Gly Gly
65              70
```

<210> SEQ ID NO 48
<211> LENGTH: 227
<212> TYPE: PRT
<213> ORGANISM: Homo sapiens

<400> SEQUENCE: 48

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
                50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225
```

ANTIBODIES DIRECTED TO ANGIOPOIETIN-1 AND ANGIOPOIETIN-2 AND USES THEREOF

REFERENCE TO RELATED APPLICATIONS

This application is a divisional of U.S. Ser. No. 12/378,993 filed Feb. 19, 2009, now U.S. Pat. No. 8,030,025, which claims the benefit of U.S. Provisional Application Ser. No. 61/139,361 filed Dec. 19, 2008, and U.S. Provisional Application Ser. No. 61/061,943 filed Jun. 16, 2008, and U.S. Provisional Application Ser. No. 61/066,632 filed Feb. 20, 2008, which are incorporated herein by reference.

The present application is being filed along with a Sequence Listing in text format. The Sequence Listing is provided as a file entitled A-1382-US-NP_ Seq Listing AsFiledInParent02192009.txt, created Feb. 19, 2009, which is 38 KB in size. The information in the text format of the Sequence Listing is incorporated herein by reference in its entirety.

FIELD OF THE INVENTION

The present invention relates to specific binding agents that recognize and bind to angiopoietins-1 (Ang-1) and/or angiopoetin-2 (Ang-2). More specifically, the invention relates to the production, diagnostic use, and therapeutic use of monoclonal and polyclonal antibodies, and the antigen-binding fragments thereof, which specifically bind Ang-1 and/or Ang-2. Aspects of the invention also relate to hybridomas or other cell lines expressing such antibodies. The described antibodies are useful for diagnostics and for the treatment of diseases associated with the activity and overproduction of Ang-1 or Ang-2.

BACKGROUND OF THE INVENTION

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. Folkman, *J. Nat. Med.,* 1:27-31 (1995).

There are a number of diseases known to be associated with deregulated or undesired angiogenesis. Such diseases include, but are not limited to, ocular neovascularisation, such as retinopathies, including diabetic retinopathy, age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one of the best-characterized and most endothelial cell-selective systems involves the Tie-2 receptor tyrosine kinase (referred to as "Tie-2" or "Tie-2R" (also referred to as "ORK"); murine Tie-2 is also referred to as "tek") and its ligands, the angiopoietins (Gale, N. W. and Yancopoulos, G. D., *Genes Dev.* 13:1055-1066 [1999]). There are 4 known angiopoietins; angiopoietin-1 ("Ang-1") through angiopoietin-4 ("Ang-4"). These angiopoietins are also referred to as "Tie-2 ligands". (Davis, S., et al., *Cell,* 87:1161-1169 [1996]; Grosios, K., et al., *Cytogenet Cell Genet,* 84:118-120 [1999]; Holash, J., et al., *Investigative Ophthalmology & Visual Science,* 42:1617-1625 [1999]; Koblizek, T. I., et al., *Current Biology,* 8:529-532 [1998]; Lin, P., et al., *Proc Natl Acad Sci USA,* 95:8829-8834 [1998]; Maisonpierre, P. C., et al., *Science,* 277:55-60 [1997]; Papapetropoulos, A., et al., *Lab Invest,* 79:213-223 [1999]; Sato, T. N., et al., *Nature,* 375:70-74 [1998]; Shyu, K. G., et al., *Circulation,* 98:2081-2087 [1998]; Suri, C., et al., *Cell,* 87:1171-1180 [1996]; Suri, C., et al., *Science,* 282:468-471 [1998]; Valenzuela, D. M., et al., *Proceedings of the National Academy of Sciences of the USA,* 96:1904-1909 [1999]; Witzenbichler, B., et al., *J Biol Chem,* 273:18514-18521 [1998]). Whereas Ang-1 binding to Tie-2 stimulates receptor phosphorylation in cultured endothelial cells, Ang-2 has been observed to both agonize and antagonize Tie-2 receptor phosphorylation (Davis, S., et al., [1996], supra; Maisonpierre, P. C., et al., [1997], supra; Kim, I., J. H. Kim, et al., *Oncogene* 19(39): 4549-4552 (2000); Teichert-Kuliszewska, K., P. C. Maisonpierre, et al., *Cardiovascular Research* 49(3): 659-70 (2001)).

The phenotypes of mouse Tie-2 and Ang-1 knockouts are similar and suggest that Ang-1-stimulated Tie-2 phosphorylation mediates remodeling and stabilization of developing vessels in utero through maintenance of endothelial cell-support cell adhesion (Dumont, D. J., et al., *Genes & Development,* 8:1897-1909 [1994]; Sato, T. N., et al., *Nature,* 376: 70-74 [1995]; Suri, C., et al., [1996], supra). The role of Ang-1 in vessel stabilization is thought to be conserved in the adult, where it is expressed widely and constitutively (Hanahan, D., *Science,* 277:48-50 [1997]; Zagzag, D., et al., *Experimental Neurology,* 159:391-400 [1999]). In contrast, Ang-2 expression is primarily limited to sites of vascular remodeling, where it is thought to block Ang-1 function, thereby inducing a state of vascular plasticity conducive to angiogenesis (Hanahan, D., [1997], supra; Holash, J., et al., *Science,* 284:1994-1998 [1999]; Maisonpierre, P. C., et al., [1997], supra).

Numerous published studies have purportedly demonstrated vessel-selective Ang-2 expression in disease states associated with angiogenesis. These pathological conditions include, for example, psoriasis, macular degeneration, and cancer (Bunone, G., et al., *American Journal of Pathology,* 155:1967-1976 [1999]; Etoh, T., et al., *Cancer Research,* 61:2145-2153 [2001]; Hangai, M., et al., *Investigative Ophthalmology & Visual Science,* 42:1617-1625 [2001]; Holash, J., et al., [1999] supra; Kuroda, K., et al., *Journal of Investigative Dermatology,* 116:713-720 [2001]; Otani, A., et al., *Investigative Ophthalmology & Visual Science,* 40:1912-1920 [1999]; Stratmann, A., et al., *American Journal of Pathology,* 153:1459-1466 [1998]; Tanaka, S., et al., *J Clin Invest,* 103:34-345 [1999]; Yoshida, Y., et al., *International Journal of Oncology,* 15:1221-1225 [1999]; Yuan, K., et al., *Journal of Periodontal Research,* 35:165-171 [2000]; Zagzag, D., et al., [1999] supra). Most of these studies have focused on cancer, in which many tumor types appear to display vascular Ang-2 expression. In contrast with its expression in pathological angiogenesis, Ang-2 expression in normal tissues is extremely limited (Maisonpierre, P. C., et al., [1997], supra; Mezquita, J., et al., *Biochemical and Biophysical Research Communications,* 260:492-498 [1999]). In the normal adult, the three main sites of angiogenesis are the ovary, placenta, and uterus; these are the primary tissues in normal (i.e., non-cancerous) tissues in which Ang-2 mRNA has been detected.

Certain functional studies suggest that Ang-2 may be involved in tumor angiogenesis. Ahmad et al. (*Cancer Res.*, 61:1255-1259 [2001]) describe Ang-2 over-expression and show that it is purportedly associated with an increase in tumor growth in a mouse xenograft model. See also Etoh et al., supra, and Tanaka et al., supra, wherein data is presented purportedly associating Ang-2 over expression with tumor hypervascularity. However, in contrast, Yu et al. (*Am. J. Path.*, 158:563-570 [2001]) report data to show that overexpression of Ang-2 in Lewis lung carcinoma and TA3 mammary carcinoma cells purportedly prolonged the survival of mice injected with the corresponding transfectants.

In the past few years, various publications have suggested Ang-1, Ang-2 and Tie-2 as a possible target for anti-cancer therapy. For example, U.S. Pat. Nos. 6,166,185, 5,650,490, and 5,814,464 each disclose the concept of anti-Tie-2 ligand antibodies and receptor bodies. U.S. Patent App. Pub. No. 2003/0124129A1 describes certain anti-Ang 2 antibodies and their use in treatment of cancer. Lin et al. (*Proc. Natl. Acad. Sci. USA*, 95:8829-8834 [1998]) injected an adenovirus expressing soluble Tie-2 into mice; the soluble Tie-2 purportedly decreased the number and size of the tumors developed by the mice. In a related study, Lin et al. (*J. Clin. Invest.*, 100:2072-2078 [1997]) injected a soluble form of Tie-2 into rats; this compound purportedly reduced tumor size in the rats. Siemeister et al. (*Cancer Res.*, 59:3185-3189 [1999]) generated human melanoma cell lines expressing the extracellular domain of Tie-2, injected these cell lines into nude mice, and concluded that soluble Tie-2 purportedly resulted in a "significant inhibition" of tumor growth and tumor angiogenesis.

Hence, an effective anti-Ang-2 therapy might benefit a vast population of cancer patients because most solid tumors require neovascularization to grow beyond 1-2 millimeters in diameter. Such therapy might have wider application in other angiogenesis-associated diseases as well, such as retinopathies, arthritis, and psoriasis.

SUMMARY OF THE INVENTION

Although much evidence points to the usefulness of inhibiting Ang2 levels in treatment of unwanted angiogenesis (or any subset of conditions involving unwanted generation of blood vessels, like arteriogenesis), the present state of the art does not make clear whether the simultaneous inhibition of Ang1 would be beneficial in such therapies and if so what degree of Ang1 inhibition, in addition to Ang2 inhibition, might prove to provide at least an additive therapeutic effect. Accordingly, the present invention addresses an unrecognized need to identify new agents that specifically recognize and bind both Ang-1 and Ang-2 ligands. The binding agents, such as the antibodies of the present invention, have the desired activity levels in inhibiting Ang2 as well as Ang1 that make them particularly useful in a variety of settings such as diagnostic screening, bioassays, and therapeutic intervention in diseases that are associated with Ang-1 and/or Ang-2 activity, such as cancer, inflammation, and other diseases related to undesired angiogenesis.

The various embodiments of the invention relate to targeted binding agents that specifically bind to Ang-1 and/or Ang-2 and therein inhibit physiological or pathological angiogenesis. Mechanisms by which this can be achieved can include, but are not limited to, either inhibition of binding of Ang-1 and/or Ang-2 to the Tie1 and/or Tie2 receptor, inhibition of Ang-1 and/or Ang-2 induced Tie1 and/or Tie2 signaling, or increased clearance of Ang1 and/or Ang-2 from a patient's body, therein reducing the effective concentration of Ang-1 and/or Ang-2.

One embodiment of the invention, the specific binding agent is a fully human antibody that specifically binds to Ang-1 and/or Ang-2 and prevents Ang-1 and/or Ang-2 binding to Tie1 and/or Tie2 receptors. Yet another embodiment of the invention is a fully human monoclonal antibody that binds to Ang-1 and/or Ang-2 and also inhibits Ang-1 and/or Ang-2 induced Tie1 and/or Tie2 phosphorylation. The antibody may bind Ang-1 and/or Ang-2 with a Kd of less than about 100 pM, 30 pM, 20 pM, 10 pM, 5 pM or 1 pM. Certain embodiments of the invention are antibodies of the IgG type, e.g., IgG1, IgG2, IgG3, and IgG4.

Another embodiment of the invention provides a binding agent such as an antibody comprising a heavy chain and a light chain, wherein said heavy chain comprises a heavy chain variable region selected from the group consisting of H2 (SEQ ID NO. 1); H3 (SEQ ID NO. 2); H4 (SEQ ID NO. 3); H6 (SEQ ID NO. 4); H10 (SEQ ID NO. 5); H11 (SEQ ID NO. 6); H5P (SEQ ID NO. 7); and antigen binding fragments thereof; and said light chain comprises a light chain variable region selected from the group consisting of: L1 (SEQ ID NO. 8); L2 (SEQ ID NO. 9); L4 (SEQ ID NO. 10); L6 (SEQ ID NO. 11); L7 (SEQ ID NO. 12); L8 (SEQ ID NO. 13); L9 (SEQ ID NO. 14); L11 (SEQ ID NO. 15); L12 (SEQ ID NO. 16); L13 (SEQ ID NO. 17); and antigen binding fragments thereof.

The invention also provides a specific binding agent comprising at least one peptide selected from the group consisting of: H2 (SEQ ID NO. 1); H3 (SEQ ID NO. 2); H4 (SEQ ID NO. 3); H6 (SEQ ID NO. 4); H10 (SEQ ID NO. 5); H11 (SEQ ID NO. 6); H5P (SEQ ID NO. 7); L1 (SEQ ID NO. 8); L2 (SEQ ID NO. 9); L4 (SEQ ID NO. 10); L6 (SEQ ID NO. 11); L7 (SEQ ID NO. 12); L8 (SEQ ID NO. 13); L9 (SEQ ID NO. 14); L11 (SEQ ID NO. 15); L12 (SEQ ID NO. 16); L13 (SEQ ID NO. 17); and antigen binding fragments thereof.

It will be appreciated that the specific binding agent can be, for example, an antibody, such as a polyclonal, monoclonal, chimeric, humanized, or a fully human antibody. The antibody may also be a single chain antibody. Other examples of specific binding agents include peptibodies, such as peptibody mL4-3, avimers, other forms of peptide molecules (such as Fc-fusion molecules and Ab-fusion molecules (see CovX-Pfizer technology)) that contain peptide sequences which recognize and bind to a protein target (in this context, Ang2 and or Ang1 ligand(s)), etc.

A specific embodiment of the invention relates to peptibodies such as mL4-3 that bind Ang1. Other embodiments of the invention include the peptide portion of mL4-3 as well as similar Ang1-binding peptides that can be made by addition, deletion, and/or insertion of amino acids to and from this peptide. Similar additions, deletions, or insertions can be made to the Fc portion of the mL4-3 peptibody. Further alterations to the mL4-3 and peptibodies in general are well-known in the art and taught in, for example, WO00/24782 and WO03/057134 which are incorporated herein by reference to the sections which describe and teach making binding agents that contain a randomly generated peptide which binds a desired target.

The invention further relates to a hybridoma that produces a monoclonal antibody according to the invention, as well as a cell lines contining (through any means such as by transfection, transformation, electroporation) with the nucleic acid sequences necessary to express the present specific binding agents such as the antibodies described herein.

It will also be appreciated that the invention relates to conjugates as described herein. The conjugate can be, for example, a specific binding agent (such as an antibody) of the invention conjugated to other proteinatious, carbohydrate, lipid, or mixed moiety molecule(s).

The invention further relates to nucleic acid molecules encoding the specific binding agents (such as an antibody) of the invention, as well as a vector comprising such nucleic acid molecule, as well as a host cell containing the vector.

Additionally, the invention provides a method of making a specific binding agent comprising, (a) transforming a host cell with at least one nucleic acid molecule encoding the specific binding agent; (b) expressing the nucleic acid molecule in said host cell; and (c) isolating said specific binding agent. The invention further provides a method of making an antibody comprising: (a) transforming a host cell with at least one nucleic acid molecule encoding the antibody according to the invention; (b) expressing the nucleic acid molecule in said host cell; and (c) isolating said specific binding agent.

Further, the invention relates to a method of inhibiting undesired angiogenesis in a mammal by administering a therapeutically effective amount of a specific binding agent according to the invention. The invention also provides a method of treating cancer in a mammal by administering a therapeutically effective amount of a specific binding agent according to the invention.

The invention also relates to a method of inhibiting undesired angiogenesis in a mammal comprising by administering a therapeutically effective amount of an antibody according to the invention. The invention additionally provides a method of treating cancer in a mammal comprising administering a therapeutically effective amount of antibody according to the invention.

It will be appreciated that the invention further relates to pharmaceutical compositions comprising the specific binding agent according to the invention and a pharmaceutically acceptable formulation agent. The pharmaceutical composition may comprise an antibody according to the invention and a pharmaceutically acceptable formulation agent.

The invention provides a method of modulating or inhibiting angiopoietin-2 activity by administering one or more specific binding agents of the invention. The invention also provides a method of modulating or inhibiting angiopoietin-2 activity by administering an antibody of the invention.

The invention further relates to a method of modulating at least one of vascular permeability or plasma leakage in a mammal comprising administering a therapeutically effective amount of the specific binding agent according to the invention. The invention also relates to a method of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis in a mammal comprising administering a therapeutically effective amount of a specific binding agent according to the invention.

The invention further provides a method of modulating at least one of vascular permeability or plasma leakage in a mammal comprising administering a therapeutically effective amount of an antibody according to the invention. The invention also relates to a method of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis in a mammal comprising administering a therapeutically effective amount of an antibody according to the invention.

Furthermore, the invention relates to a method of treating cancer in a mammal comprising administering a therapeutically effective amount of a specific binding agent according to the invention and a chemotherapeutic agent. It will be appreciated by those in the art that the specific binding agent and chemotherapeutic agent need not be administered simultaneously.

The invention also provides a specific binding agent comprising heavy chain complementarity determining region 1 (CDR 1) of any of: SEQ ID NO. 18; The invention further relates to a specific binding agent comprising heavy chain complementarity determining region 2 (CDR 2) of any of: SEQ ID NO. 26; SEQ ID NO. 27; SEQ ID NO. 28; SEQ ID NO. 29; and antigen binding fragments thereof.

The invention also relates to a specific binding agent comprising heavy chain complementarity determining region 3 (CDR 3) of any of: SEQ ID NO. 32; SEQ ID NO. 34; SEQ ID NO. 35; SEQ ID NO. 37; SEQ ID NO. 38; SEQ ID NO. 39); and antigen binding fragments thereof.

The invention also provides a specific binding agent comprising light chain complementarity determining region 1 (CDR 1) of any of: SEQ ID NO. 19; SEQ ID NO. 20; SEQ ID NO. 21; SEQ ID NO. 22; SEQ ID NO. 23; SEQ ID NO. 24; SEQ ID NO. 25; and antigen binding fragments thereof;

The invention further relates to a specific binding agent comprising light chain complementarity determining region 2 (CDR 2) of any of: SEQ ID NO. 27; SEQ ID NO. 30; SEQ ID NO. 31; and antigen binding fragments thereof.

The invention also relates to a specific binding agent comprising light chain complementarity determining region 3 (CDR 3) of any of: SEQ ID NO. 33; SEQ ID NO. 36; SEQ ID NO. 40; and antigen binding fragments thereof.

Other embodiments of the invention include isolated nucleic acid molecules encoding any of the antibodies described herein, vectors having isolated nucleic acid molecules encoding anti-Ang-1 and/or Anti-Ang-2 antibodies or a host cell transformed with any of such nucleic acid molecules. In addition, one embodiment of the invention is a method of producing an anti-Ang-1 and/or anti-Ang-2 antibody by culturing host cells under conditions wherein a nucleic acid molecule is expressed to produce the antibody followed by recovering the antibody. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

A further embodiment herein includes a method of producing high affinity antibodies to Ang-1 and/or Ang-2 by immunizing a mammal with human Ang-1 or 2, or a fragment thereof, and one or more orthologous sequences or fragments thereof.

Moreover, the invention relates to a method of detecting the level of Ang-1 or Ang-2 in a biological sample by (a) contacting a specific binding agent of the invention with the sample; and (b) determining the extent of binding of the specific binding agent to the sample. The invention also relates to a method of detecting the level of Ang-2 in a biological sample by (a) contacting an antibody of the invention with the sample; and (b) determining the extent of binding of the antibody to the sample.

The invention also relates to a method of inhibiting undesired angiogenesis in a mammal comprising administering a therapeutically effective amount of a polypeptide or composition as described herein. The invention also relates to a method of modulating angiogenesis in a mammal comprising administering a therapeutically effective amount of a polypeptide or composition as described herein. The invention further relates to a method of inhibiting tumor growth characterized by undesired angiogenesis in a mammal comprising administering a therapeutically effective amount of a polypeptide or composition as described herein. Additionally, the invention relates to a method of treating cancer in a mammal comprising administering a therapeutically effective amount of a polypeptide or composition as described herein, and a chemotherapeutic agent. The specific polypeptide or composition as described herein and chemotherapeutic agent need not be administered simultaneously. In a preferred embodiment, the chemotherapeutic agent is at least one of 5-FU, CPT-11, and Taxotere. It will be appreciated, however, that other suitable chemotherapeutic agents and other cancer therapies can be used.

Additionally, the invention relates to a method of treating cancer in a mammal comprising administering a therapeutically effective amount of a polypeptide or composition as described herein, and an anti-VEGF agent or a multikinase inhibitor (MKI). In a preferred embodiment, the anti-VEGF agent or a multikinase inhibitor (MKI) would be chosen from Avastin® (bevacizumab), Lucentis® (ranibizumab), Macugen® (pegaptanib), Sutent® (sunitinib), Nexavar® (sorafenib), motesanib diphosphate, Zactima® (vandetanib), Recentin (AZD 2171), AG-013736 (axitinib). It will be appreciated, however, that other suitable anti-angiogenic agents and other cancer therapies can be used.

It will be appreciated that the specific binding agents of the invention are used to treat a number of diseases associated with deregulated or undesired angiogenesis. Such diseases include, but are not limited to, ocular neovascularisation, such as retinopathies (including diabetic retinopathy and age-related macular degeneration) psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Additional diseases which can be treated by administration of the specific binding agents will be apparent to those skilled in the art. Such additional diseases include, but are not limited to, obesity, vascular permeability, plasma leakage, and bone-related disorders, including osteoporosis. Thus, the invention further relates to methods of treating these diseases associated with deregulated or undesired angiogenesis.

Additional embodiments of the invention include a specific binding agent comprising at least one peptide selected from the group consisting of: SEQ ID NO. 1; SEQ ID NO. 2; SEQ ID NO. 3; SEQ ID NO. 4; SEQ ID NO. 5; SEQ ID NO. 6; SEQ ID NO. 7; SEQ ID NO. 8; SEQ ID NO. 9; SEQ ID NO. 10; SEQ ID NO. 11; SEQ ID NO. 12; SEQ ID NO. 13; SEQ ID NO. 14; SEQ ID NO. 15; SEQ ID NO. 16; SEQ ID NO. 17; and antigen-binding fragments thereof. Also contemplated are antibodies containing the aforementioned polypeptide sequences. These antibodies are polyclonal, monoclonal, chimeric, humanized, or fully human antibodies. They are single chain antibody as well as multi-chain antibodies. Hybridomas that produce the monoclonal antibodies are also contemplated, as well as, nucleic acid molecules encoding the polypeptides and the antibodies, the vectors containing these nucleic acid molecules, and the host cells, such as CHO cells, that contain and express them. A method of making a binding agent or an antibody of the present invention comprises transforming a host cell with at least one nucleic acid molecule encoding the binding agent or antibody; expressing the nucleic acid molecule in said host cell; and isolating said specific binding agent or antibody.

A diagnostic use of the invention includes a method of detecting the level of angiopoietin-1 and/or angiopoietin-in a biological sample comprising contacting an antibody or binding agent described herein with said biological sample; and determining the extent of binding of the antibody or binding agent to said sample.

Amongst the specific therapeutic uses of the invention are methods of inhibiting undesired angiogenesis (or any subset of conditions involving unwanted generation of blood vessels, like arteriogenesis), in a mammal comprising administering a therapeutically effective amount of the isolated polypeptides or the binding agents such as antibodies made therefrom. Amongst such undesired angiogenesis (or any subset of conditions involving unwanted generation of blood vessels, like arteriogenesis), are cancer and inflammatory diseases in mammals. Therefore, a pharmaceutical composition is contemplated that comprises the isolated polypeptide, binding agent or antibody of the invention in admixture with a pharmaceutical carrier therefore. Pharmaceutically acceptable formulation agents, of course, are often used to prepare such pharmaceutical compositions for administration to subjects in need thereof.

Other methods of using the compositions of the present invention include a method of modulating or inhibiting angiopoietin-1 and/or angiopoietin-2 activity comprising administering to a patient the isolated polypeptide, binding agent or antibody described herein. Such methods of modulating or inhibiting angiopoietin-1 and/or angiopoietin-2 activity comprise administering to a patient the polypeptide, binding agent, or antibody described herein. Such methods include modulating at least one of vascular permeability or plasma leakage in a mammal comprising administering to a mammal a therapeutically effective amount of the isolated polypeptide, binding agent or antibody described herein. Also included are methods of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis.

Also contemplated is a combotherapy (combination therapy) method such as a method of treating cancer in a mammal comprising administering a therapeutically effective amount of an isolated polypeptide, binding agent or antibody described herein and a chemotherapeutic agent. In such methods, sometimes the isolated polypeptide, binding agent or antibody and the chemotherapeutic agent are administered simultaneously and at other times are not, depending upon the specific condition, regulatory approval, and the judgement of the medical professionals.

Other types of combotherapy include a method of treating cancer in a mammal comprising administering to a subject in need thereof a therapeutically effective amount of an isolated polypeptide, binding agent or antibody described herein and a second molecule that binds a ligand to any one of the VEGF receptors 1-3. Examples of such second molecules that bind a ligand to any one of the VEGF receptors 1-3 are Avastin®, Lucentis®, and Macugen®.

Use of the polypeptides, binding agents, or antibodies described herein are also contemplated in combination with small molecule agents for therapeutic administration to subjects in need thereof. Such small molecule agents include those that modulate the signaling of any one of the VEGF receptors 1-3 as well as those that are multikinase inhibitors. For example, Sutent®, Nexavar®, Motesanib diphosphate, Axitinib, Zactima, AZD 2171, Recentin, and AG-013736 are contemplated for use in combotherapy with the polypeptides, binding agents, and antibodies described herein.

Certain other embodiments of the invention relate to a specific binding agent comprising CDR 1 of any of SEQ ID NO. 18; SEQ ID NO. 19; SEQ ID NO. 20; SEQ ID NO. 21; SEQ ID NO. 22; SEQ ID NO. 23; SEQ ID NO. 24; SEQ ID NO. 25; a specific binding agent comprising CDR 2 of any of SEQ ID NO. 26; SEQ ID NO. 27; SEQ ID NO. 28; SEQ ID NO. 29; SEQ ID NO. 30; SEQ ID NO. 31; and a specific binding agent comprising CDR 3 of any of SEQ ID NO. 32; SEQ ID NO. 33; SEQ ID NO. 34; SEQ ID NO. 35; SEQ ID NO. 36; SEQ ID NO. 37; SEQ ID NO. 38; SEQ ID NO. 39; SEQ ID NO. 40. The specific binding agent may comprise 1, 2, 3, 4, 5, or 6 CDRs.

Similarly, nucleic acid molecules encoding the above-mentioned specific binding agents are contemplated. Also contemplated is a method of detecting the level of angiopoietin-1 and/or angiopoietin-2 in a biological sample comprising contacting a specific binding agent as described herein with said biological sample; and determining the extent of binding of the specific binding agent to said sample. Additionally, a method is contemplated for detecting the level of angiopoietin-1 and/or angiopoietin-2 in a biological sample comprising contacting any one of the antibodies described herein with said biological sample; and determining the extent of binding of the antibody to said sample.

A further embodiment of the invention is an antibody comprising a heavy chain and a light chain, the heavy chain comprising a heavy chain variable region selected from the group consisting of SEQ ID NO. 1; SEQ ID NO. 2; SEQ ID NO. 3; SEQ ID NO. 4; SEQ ID NO. 5; SEQ ID NO. 6 and, SEQ ID NO. 7; and the light chain comprising a light chain variable region selected from the group consisting of SEQ ID NO. 8; SEQ ID NO. 9; SEQ ID NO. 10; SEQ ID NO. 11; SEQ ID NO. 12; SEQ ID NO. 13; SEQ ID NO. 14; SEQ ID NO. 15; SEQ ID NO. 16 and, SEQ ID NO. 17; as well as antigen binding fragments thereof. Naturally, nucleic acid molecules encoding the above-described antibodies and antigen-binding fragments are also contemplated.

In another embodiment, the present invention is directed to an isolated antibody comprising a heavy chain and a light chain, the light chain comprising a light chain variable domain and the heavy chain comprising a heavy chain variable domain, the heavy chain variable domain having the sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7; wherein the antibody specifically binds to at least one of Ang1 and Ang2 ligands of Tie 2 receptor.

In a further embodiment, the invention is an isolated antibody comprising a heavy chain and a light chain, the heavy chain comprising a heavy chain variable domain and the light chain comprising a light chain variable domain, the light chain variable domain having the sequence selected from the group consisting of SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17; wherein the antibody specifically binds to at least one of Ang1 and Ang2 ligands of Tie 2 receptor.

In an additional embodiment, the invention is directed to an isolated antibody comprising a heavy chain and light chain, the heavy chain comprising a heavy chain variable domain and the light chain comprising a light chain variable domain, wherein the heavy chain variable domain comprises 1, 2, or 3 heavy chain CDRs selected from the group of HC CDRs consisting of SEQ ID NOs: 18, 26, 28, 32, 34, 35, 37, 38 and, 39, and wherein the antibody specifically binds to at least one of Ang1 and Ang2 ligands of Tie 2 receptor.

In another embodiment, the invention is directed to an isolated antibody which comprises a light chain and a heavy chain, wherein the light chain comprises a light chain variable domain and the heavy chain comprises a heavy chain variable domain, wherein the light chain variable domain comprises 1, 2, or 3 light chain CDRs selected from the group of LC CDRs consisting of SEQ ID NOs: 19, 20, 21, 22, 23, 27, 33, 36, 40, and wherein the antibody specifically binds to at least one of Ang1 and Ang2 ligands of Tie 2 receptor.

In a further embodiment, the invention is an isolated antibody which comprises a heavy chain and a light chain, wherein the heavy chain comprises a heavy chain variable domain and the light chain comprises a light chain variable domain, wherein the heavy chain comprises 3 heavy chain (HC) CDRs and said light chain variable domain comprises 3 light chain (LC) CDRs, wherein the sequences of said HC and LC CDRs of the antibody are selected from the group consisting of:

(a) SEQ ID NOs: 18, 26, 32 of the HC plus SEQ ID NOs: 19, 27, 33 of the LC,
(b) SEQ ID NOs: 18, 26, 34 of the HC plus SEQ ID NOs: 19, 27, 33 of the LC,
(c) SEQ ID NOs: 18, 26, 35 of the HC plus SEQ ID NOs: 20, 27, 36 of the LC,
(d) SEQ ID NOs: 18, 26, 37 of the HC plus SEQ ID NOs: 19, 27, 33 of the LC,
(e) SEQ ID NOs: 18, 26, 38 of the HC plus SEQ ID NOs: 19, 27, 33 of the LC,
(f) SEQ ID NOs: 18, 26, 35 of the HC plus SEQ ID NOs: 19, 27, 33 of the LC,
(g) SEQ ID NOs: 18, 26, 34 of the HC plus SEQ ID NOs: 21, 27, 33 of the LC,
(h) SEQ ID NOs: 18, 28, 39 of the HC plus SEQ ID NOs: 19, 27, 33 of the LC,
(i) SEQ ID NOs: 18, 26, 34 of the HC plus SEQ ID NOs: 22, 27, 33 of the LC,
(j) SEQ ID NOs: 18, 26, 32 of the HC plus SEQ ID NOs: 22, 27, 33 of the LC,
(k) SEQ ID NOs: 18, 29, 39 of the HC plus SEQ ID NOs: 19, 27, 33 of the LC,
(l) SEQ ID NOs: 18, 26, 34 of the HC plus SEQ ID NOs: 23, 27, 33 of the LC,
(m) SEQ ID NOs: 18, 26, 35 of the HC plus SEQ ID NOs: 20, 27, 40 of the LC,
(n) SEQ ID NOs: 18, 26, 32 of the HC plus SEQ ID NOs: 21, 27, 33 of the LC,
(o) SEQ ID NOs: 18, 26, 35 of the HC plus SEQ ID NOs: 24, 27, 33 of the LC,
(p) SEQ ID NOs: 18, 26, 35 of the HC plus SEQ ID NOs: 21, 27, 33 of the LC,
(q) SEQ ID NOs: 18, 26, 35 of the HC plus SEQ ID NOs: 23, 27, 33 of the LC,
(r) SEQ ID NOs: 18, 26, 34 of the HC plus SEQ ID NOs: 20, 30, 33 of the LC,
(s) SEQ ID NOs: 18, 26, 34 of the HC plus SEQ ID NOs: 25, 27, 33 of the LC,
(t) SEQ ID NOs: 18, 26, 35 of the HC plus SEQ ID NOs: 20, 30, 33 of the LC,
(u) SEQ ID NOs: 18, 26, 34 of the HC plus SEQ ID NOs: 20, 27, 40 of the LC, and
(v) SEQ ID NOs: 18, 26, 34 of the HC plus SEQ ID NOs: 20, 31, 33 of the LC;
wherein the antibody specifically binds to at least one of Ang1 and Ang2 ligands of Tie 2 receptor.

The present invention also is directed to an antibody having a heavy chain and light chain, where the light chain has a light chain variable domain having three LC CDRs of any one of (a) through (v), supra, wherein the antibody specifically to at least one of Ang1 and Ang2 ligands of Tie 2 receptor.

Additionally, the present invention also is directed to an antibody having a heavy chain and light chain, where the heavy chain has a heavy chain variable domain having three HC CDRs of any one of (a) through (v), supra, wherein the antibody specifically to at least one of Ang1 and Ang2 ligands of Tie 2 receptor.

Nucleic acid molecules encoding any of the aforementioned antibodies and antigen-binding fragments thereof are also contemplated. Other embodiments of this invention will be readily apparent from the disclosure provided herewith.

DETAILED DESCRIPTION OF INVENTION

The section headings are used herein for organizational purposes only, and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Sambrook et al. (Molecular Cloning: A Laboratory Manual. Cold Spring Harbor Laboratory Press, Cold Spring Harbor, N.Y. [1989]), or as described herein. Unless specific definitions are provided, the nomenclature utilized in connection with, and the laboratory procedures and techniques of analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

The terms used to describe the present invention, unless specifically defined herein, shall have their meaning as understood and used in the art.

It should be noted that the terms H5 and H5P are used interchangeably and refer to the heavy chain used in various embodiments of the invention, e.g., mAbs named as H5L7, H5L6, H5L8, H5L4, H5L11, H5L1, H5L12, and H5L9.

Figure 6:
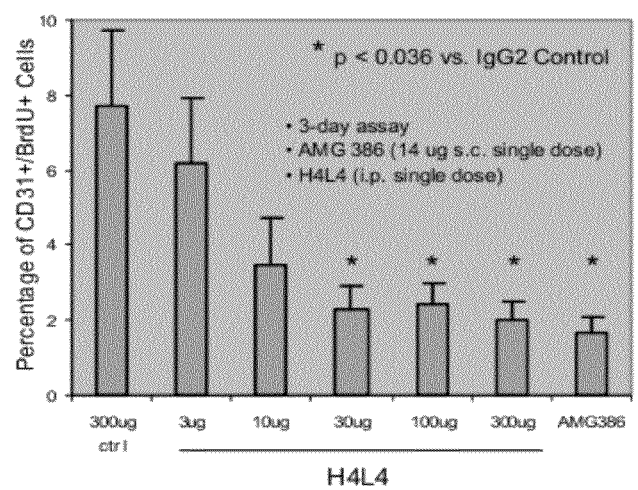
FIG. 6 depicts the effect of the antibody H4L4 on endothelial cell proliferation in Colo205 tumor-bearing mice. Details are described in the Examples.

The term "Ang-2" refers to the polypeptide set forth in FIG. 6 of U.S. Pat. No. 6,166,185 ("Tie-2 ligand-2"), incorporated herein by reference, or fragments thereof as well as related polypeptides which include allelic variants, splice variants, derivatives, substitution, deletions, and/or insertion variants, fusion peptides and polypeptides, and interspecies homologs. The Ang-2 polypeptide may or may not include additional terminal residues, e.g., leader sequences, targeting sequences, amino terminal methionine, amino terminal methionine and lysine residues, and/or tag or fusion proteins sequences, depending on the manner in which it is prepared.

The term "specific binding agent" refers to a molecule, preferably a proteinaceous molecule, that binds Ang-2 as well as Ang-1 (and variants and derivatives thereof as defined herein) with a greater affinity than other angiopoietins. A specific binding agent may be a protein, peptide, nucleic acid, carbohydrate, lipid, or small molecular weight compound which binds preferentially to Ang-2 and Ang-1. In a preferred embodiment, the specific binding agent according to the present invention is an antibody, such as a polyclonal antibody, a monoclonal antibody (mAb), a chimeric antibody, a CDR-grafted antibody, a multi-specific antibody, a bi-specific antibody, a catalytic antibody, a humanized antibody, a human antibody, an anti-idiotypic (anti-Id) antibody, and antibodies that can be labeled in soluble or bound form, as well as antigen-binding fragments, variants or derivatives thereof, either alone or in combination with other amino acid sequences, provided by known techniques. Such techniques include, but are not limited to enzymatic cleavage, chemical cleavage, peptide synthesis or recombinant techniques. The anti-Ang-2 and Ang-1 specific binding agents of the present invention are capable of binding portions of Ang-2 and Ang-1 that modulate, e.g., inhibit or promote, the biological activity of Ang-2 and Ang-1 and/or other Ang-2- and Ang-1-associated activities.

The term "polyclonal antibody" refers to a heterogeneous mixture of antibodies that recognize and bind to different epitopes on the same antigen. Polyclonal antibodies may be obtained from crude serum preparations or may be purified using, for example, antigen affinity chromatography, or Protein A/Protein G affinity chromatography.

The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same epitope on the antigen. The term "monoclonal" is not limited to any particular method for making the antibody, nor is the term limited to antibodies produced in a particular species, e.g., mouse, rat, etc.

The term "chimeric antibodies" refers to antibodies in which a portion of the heavy and/or light chain is identical with or homologous to a corresponding sequence in an antibody derived from a particular species or belonging to a particular antibody class or subclass, while the remainder of the chain(s) is/are identical with or homologous to a corresponding sequence in antibodies derived from another species or belonging to another antibody class or subclass. Also included are antigen-binding fragments of such antibodies that exhibit the desired biological activity (i.e., the ability to specifically bind Ang-2). See, U.S. Pat. No. 4,816,567 and Morrison et al., *Proc Natl Acad Sci (USA)*, 81:6851-6855 [1985].

The term "CDR grafted antibody" refers to an antibody in which the CDR from one antibody of a particular species or isotype is recombinantly inserted into the framework of another antibody of the same or different species or isotype.

The term "multi-specific antibody" refers to an antibody having variable regions that recognize more than one epitope on one or more antigens. A subclass of this type of antibody is a "bi-specific antibody" which recognizes two distinct epitopes on the same or different antigens.

"Catalytic" antibodies refers to antibodies wherein one or more cytotoxic, or more generally one or more biologically active, moieties are attached to the targeting binding agent.

The term "humanized antibody" refers to a specific type of CDR-grafted antibody in which the antibody framework region is derived from a human but each CDR is replaced with that derived from another species, such as a murine CDR. The term "CDR" is defined infra.

The term "fully human" antibody refers to an antibody in which both the CDR and the framework are derived from one or more human DNA molecules.

The term "anti-idiotype" antibody refers to any antibody that specifically binds to another antibody that recognizes an antigen. Production of anti-idiotype antibodies can be performed by any of the methods described herein for production of Ang-2-specific antibodies except that these antibodies arise from e.g., immunization of an animal with an Ang-2-specific antibody or Ang-2-binding fragment thereof, rather than Ang-2 polypeptide itself or a fragment thereof.

The term "variants," as used herein, include those polypeptides wherein amino acid residues are inserted into, deleted from and/or substituted into the naturally occurring (or at least a known) amino acid sequence for the binding agent. Variants of the invention include fusion proteins as described below.

"Derivatives" include those binding agents that have been chemically modified in some manner distinct from insertion, deletion, or substitution variants.

"Specifically binds" refers to the ability of a specific binding agent (such as an antibody or fragment thereof) of the present invention to recognize and bind mature, full-length or partial-length target polypeptide (herein Ang-2 and Ang-1), or an ortholog thereof, such that its affinity (as determined by, e.g., Affinity ELISA or BIAcore assays as described herein) or its neutralization capability (as determined by e.g., Neutralization ELISA assays described herein, or similar assays) is at least 10 times as great, but optionally 50 times as great, 100, 250 or 500 times as great, or even at least 1000 times as great as the affinity or neutralization capability of the same for any other angiopoietin or other peptide or polypeptide.

The term "antigen binding domain" or "antigen binding region" refers to that portion of the specific binding agent (such as an antibody molecule) which contains the specific binding agent amino acid residues (or other moieties) that interact with an antigen and confer on the binding agent its specificity and affinity for the antigen. In an antibody, the antigen-binding domain is commonly referred to as the "complementarity-determining region, or CDR."

The term "epitope" refers to that portion of any molecule capable of being recognized by and bound by a specific binding agent, e.g. an antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous. Moreover, epitopes may be mimetic in that they comprise a three dimensional structure that is identical to the epitope used to generate the antibody, yet comprise none or only some of the amino acid residues found in the Ang-2 used to stimulate the antibody immune response.

The term "inhibiting and/or neutralizing epitope" is an epitope, which when bound by a specific binding agent such as an antibody, results in the loss of (or at least the decrease in) biological activity of the molecule, cell, or organism containing such epitope, in vivo, in vitro, or in situ. In the context of the present invention, the neutralizing epitope is located on or is associated with a biologically active region of Ang-2. Alternatively, the term "activating epitope" is an epitope, which when bound by a specific binding agent of the invention, such as an antibody, results in activation, or at least maintenance of a biologically active conformation, of Ang-2.

The term "antibody fragment" refers to a peptide or polypeptide which comprises less than a complete, intact antibody. Complete antibodies comprise two functionally independent parts or fragments: an antigen binding fragment known as "Fab," and a carboxy terminal crystallizable fragment known as the "Fc" fragment. The Fab fragment includes the first constant domain from both the heavy and light chain (CH1 and CL1) together with the variable regions from both the heavy and light chains that bind the specific antigen. Each of the heavy and light chain variable regions includes three complementarity determining regions (CDRs) and framework amino acid residues which separate the individual CDRs. The Fc region comprises the second and third heavy chain constant regions (CH2 and CH3) and is involved in effector functions such as complement activation and attack by phagocytic cells. In some antibodies, the Fc and Fab regions are separated by an antibody "hinge region," and depending on how the full length antibody is proteolytically cleaved, the hinge region may be associated with either the Fab or Fc fragment. For example, cleavage of an antibody with the protease papain results in the hinge region being associated with the resulting Fc fragment, while cleavage with the protease pepsin provides a fragment wherein the hinge is associated with both Fab fragment simultaneously. Because the two Fab fragments are in fact covalently linked following pepsin cleavage, the resulting fragment is termed the F(ab')2 fragment.

An Fc domain may have a relatively long serum half-life, whereas a Fab is short-lived. [Capon et al., Nature, 337: 525-31 (1989)] When expressed as part of a fusion protein, an Fc domain can impart longer half-life or incorporate such functions as Fc receptor binding, Protein A binding, complement fixation and perhaps even placental transfer into the protein to which it is fused. The Fc region may be a naturally occurring Fc region, or may be altered to improve certain qualities, such as therapeutic qualities or circulation time.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable regions typically differ extensively in amino acid sequence even among antibodies of the same species. The variable region of an antibody typically determines the binding and specificity of each particular antibody for its particular antigen. The variability in sequence is concentrated in those regions referred to as complementarity-determining regions (CDRs), while the more highly conserved regions in the variable domain are called framework regions (FR). The CDRs of the light and heavy chains contain within them the amino acids which are largely responsible for the direct interaction of the antibody with antigen, however, amino acids in the FRs can significantly affect antigen binding/recognition as discussed herein infra.

The term "light chain" when used in reference to an antibody collectively refers to two distinct types, called kappa (k) or lambda (l) based on the amino acid sequence of the constant domains.

The term "heavy chain" when used in reference to an antibody collectively refers to five distinct types, called alpha, delta, epsilon, gamma and mu, based on the amino acid sequence of the heavy chain constant domain. The combination of heavy and light chains give rise to five known classes of antibodies: IgA, IgD, IgE, IgG and IgM, respectively, including four known subclasses of IgG, designated as $IgG_1$, $IgG_2$, $IgG_3$ and $IgG_4$.

The term "naturally occurring" when used in connection with biological materials such as nucleic acid molecules, polypeptides, host cells, and the like, refers to those which are found in nature and not modified by a human being.

The term "isolated" when used in relation to Ang-2 or to a specific binding agent of Ang-2 refers to a compound that is free from at least one contaminating polypeptide or compound that is found in its natural environment, and preferably substantially free from any other contaminating mammalian polypeptides that would interfere with its therapeutic or diagnostic use.

The term "mature" when used in relation to Ang-2, anti-Ang-2 antibody, or to any other proteinaceous specific binding agent of Ang-2 refers to a peptide or a polypeptide lacking a leader or signal sequence. When a binding agent of the invention is expressed, for example, in a prokaryotic host cell, the "mature" peptide or polypeptide may also include additional amino acid residues (but still lack a leader sequence) such as an amino terminal methionine, or one or more methionine and lysine residues. A peptide or polypeptide produced in this manner may be utilized with or without these additional amino acid residues having been removed.

Specific Binding Agents and Antibodies

As used herein, the term "specific binding agent" refers to a molecule that has specificity for recognizing and binding Ang-2 and Ang-1, as described herein. Suitable specific binding agents include, but are not limited to, antibodies and derivatives thereof, polypeptides, and small molecules. Suitable specific binding agents may be prepared using methods known in the art. An exemplary Ang-2 and Ang-1 polypeptide specific binding agent of the present invention is capable of binding a certain portion of the Ang-2 and Ang-1 polypeptides, and preferably modulating the activity or function of Ang-2 and Ang-1 polypeptides.

Specific binding agents such as antibodies and antibody fragments that specifically bind Ang-2 and Ang-1 polypeptides are within the scope of the present invention. The antibodies may be polyclonal including mono-specific polyclonal, monoclonal (mAbs), recombinant, chimeric, humanized such as CDR-grafted, human, single chain, catalytic, multi-specific and/or bi-specific, as well as antigen-binding fragments, variants, and/or derivatives thereof.

Polyclonal antibodies against Ang2 and Ang1 polypeptides generally are produced in animals (e.g., rabbits, hamsters, goats, sheep, horses, pigs, rats, gerbils, guinea pigs, mice, or any other suitable mammal, as well as other non-mammal species) by means of multiple subcutaneous or intraperitoneal injections of Ang-2 and/or Ang-1 polypeptide or a fragment thereof with or without an adjuvant. Such adjuvants include, but are not limited to, Freund's complete and incomplete, mineral gels such as aluminum hydroxide, and surface-active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants. It may be useful to conjugate an antigen polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-Ang-2 polypeptide antibody titer which can be determined using the assays described herein under "Examples". Polyclonal antibodies may be utilized in the sera from which they were detected, or may be purified from the sera, using, for example, antigen affinity chromatography or Protein A or G affinity chromatography.

Monoclonal antibodies directed toward Ang-2 polypeptides can be produced using, for example but without limitation, the traditional "hybridoma" method or the newer "phage display" technique. For example, monoclonal antibodies of the invention may be made by the hybridoma method as described in Kohler et al., *Nature* 256:495 [1975]; the human B-cell hybridoma technique [Kosbor et al., *Immunol Today* 4:72 (1983); Cote et al., *Proc Natl Acad Sci (USA)* 80: 2026-2030 (1983); Brodeur et al., *Monoclonal Antibody Production Techniques and Applications*, pp. 51-63, Marcel Dekker, Inc., New York, (1987)] and the EBV-hybridoma technique [Cole et al., *Monoclonal Antibodies and Cancer Therapy*, Alan R Liss Inc, New York N.Y., pp 77-96, (1985)]. Also provided by the invention are hybridoma cell lines that produce monoclonal antibodies reactive with Ang-2 polypeptides.

When the hybridoma technique is employed, myeloma cell lines can be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, cell lines used in mouse fusions are Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; cell lines used in rat fusions are R210.RCY3, Y3-Ag 1.2.3, IR983F and 4B210. Other cell lines useful for cell fusions are U-266, GM1500-GRG2, LICR-LON-HMy2 and UC729-6. Hybridomas and other cell lines that produce monoclonal antibodies are contemplated to be novel compositions of the present invention.

The phage display technique may also be used to generate monoclonal antibodies from any species. Preferably, this technique is used to produce fully human monoclonal antibodies in which a polynucleotide encoding a single Fab or Fv antibody fragment is expressed on the surface of a phage particle. [Hoogenboom et al., *J Mol Biol* 227: 381 (1991); Marks et al., *J Mol Biol* 222: 581 (1991); see also U.S. Pat. No. 5,885,793)]. Each phage can be "screened" using binding assays described herein to identify those antibody fragments having affinity for Ang-2. Thus, these processes mimic immune selection through the display of antibody fragment repertoires on the surface of filamentous bacteriophage, and subsequent selection of phage by their binding to Ang-2. One such procedure is described in PCT Application No. PCT/US98/17364, filed in the name of Adams et al., which describes the isolation of high affinity and functional agonistic antibody fragments for MPL- and msk-receptors using such an approach. In this approach, a complete repertoire of human antibody genes can be created by cloning naturally rearranged human V genes from peripheral blood lymphocytes as previously described [Mullinax et al., *Proc Natl Acad Sci (USA)* 87: 8095-8099 (1990)].

Once a polynucleotide sequences are identified which encode each chain of the full length monoclonal antibody or the Fab or Fv fragment(s) of the invention, host cells, either eukaryotic or prokaryotic, may be used to express the monoclonal antibody polynucleotides using recombinant techniques well known and routinely practiced in the art. Alternatively, transgenic animals are produced wherein a polynucleotide encoding the desired specific binding agent is introduced into the genome of a recipient animal, such as, for example, a mouse, rabbit, goat, or cow, in a manner that permits expression of the polynucleotide molecules encoding a monoclonal antibody or other specific binding agent. In one aspect, the polynucleotides encoding the monoclonal antibody or other specific binding agent can be ligated to mammary-specific regulatory sequences, and the chimeric polynucleotides can be introduced into the germline of the target animal. The resulting transgenic animal then produces the desired antibody in its milk [Pollock et al., *J Immunol Meth* 231:147-157 (1999); Little et al., *Immunol Today* 8:364-370 (2000)]. In addition, plants may be used to express and produce Ang-2 specific binding agents such as monoclonal antibodies by transfecting suitable plants with the polynucleotides encoding the monoclonal antibodies or other specific binding agents.

In another embodiment of the present invention, a monoclonal or polyclonal antibody or fragment thereof that is derived from other than a human species may be "humanized" or "chimerized". Methods for humanizing non-human antibodies are well known in the art. (see U.S. Pat. Nos. 5,859,205, 5,585,089, and 5,693,762). Humanization is performed, for example, using methods described in the art [Jones et al., *Nature* 321: 522-525 (1986); Riechmann et al., *Nature*, 332: 323-327 (1988); Verhoeyen et al., *Science* 239: 1534-1536 (1988)] by substituting at least a portion of, for example a rodent, complementarity-determining region (CDRs) for the corresponding regions of a human antibody. The invention also provides variants and derivatives of these human antibodies as discussed herein and well known in the art.

Also encompassed by the invention are fully human antibodies that bind Ang-2 polypeptides, as well as, antigen-binding fragments, variants and/or derivatives thereof. Such antibodies can be produced using the phage display technique described above. Alternatively, transgenic animals (e.g., mice) that are capable of producing a repertoire of human antibodies in the absence of endogenous immunoglobulin production can be used to generate such antibodies. This can be accomplished by immunization of the animal with an Ang-2 antigen or fragments thereof where the Ang-2 fragments have an amino acid sequence that is unique to Ang-2. Such immunogens can be optionally conjugated to a carrier. See, for example, Jakobovits et al., *Proc Natl Acad Sci (USA)*, 90: 2551-2555 (1993); Jakobovits et al., *Nature* 362: 255-258 (1993); Bruggermann et al., *Year in Immuno,* 7: 33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that are those having less than the full complement of these modifications, are then crossbred to obtain an animal having all of the desired immune system modifications. When administered an immunogen, these transgenic animals are capable of producing antibodies with human variable regions, including human (rather than e.g., murine) amino acid sequences, that are immuno-specific for the desired antigens. See PCT application Nos., PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1. Human antibodies may also be produced by the expression of recombinant DNA in host cells or by expression in hybridoma cells as described herein.

Transgenesis is achieved in a number of different ways. See, for example, Bruggeman et al., *Immunol Today* 17:391-7 (1996). In one approach, a minilocus is constructed such that gene segments in a germline configuration are brought artificially close to each other. Due to size limitations (i.e., having generally less than 30 kb), the resulting minilocus will contain a limited number of differing gene segments, but is still capable of producing a large repertoire of antibodies. Miniloci containing only human DNA sequences, including promoters and enhancers are fully functional in the transgenic mouse.

When larger number of gene segments are desired in the transgenic animal, yeast artificial chromosomes (YACs) are utilized. YACs can range from several hundred kilobases to 1 Mb and are introduced into the mouse (or other appropriate animal) genome via microinjection directly into an egg or via transfer of the YAC into embryonic stem (ES)-cell lines. In general, YACs are transferred into ES cells by lipofection of the purified DNA, or yeast spheroplast fusion wherein the purified DNA is carried in micelles and fusion is carried out in manner similar to hybridoma fusion protocols. Selection of desired ES cells following DNA transfer is accomplished by including on the YAC any of the selectable markers known in the art.

As another alternative, bacteriophage P1 vectors are used which are amplified in a bacterial *E. coli* host. While these vectors generally carry less inserted DNA than a YAC, the clones are readily grown in high enough yield to permit direct microinjection into a mouse egg. Use of a cocktail of different P1 vectors has been shown to lead to high levels of homologous recombination.

Once an appropriate transgenic mouse (or other appropriate animal) has been identified, using any of the techniques known in the art to detect serum levels of a circulating antibody (e.g., ELISA), the transgenic animal is crossed with a mouse in which the endogenous Ig locus has been disrupted. The result provides progeny wherein essentially all B cells express human antibodies.

As still another alternative, the entire animal Ig locus is replaced with the human Ig locus, wherein the resulting animal expresses only human antibodies. In another approach, portions of the animal's locus are replaced with specific and corresponding regions in the human locus. In certain cases, the animals resulting from this procedure may express chimeric antibodies, as opposed to fully human antibodies, depending on the nature of the replacement in the mouse Ig locus.

Human antibodies can also be produced by exposing human splenocytes (B or T cells) to an antigen in vitro, then reconstituting the exposed cells in an immunocompromised mouse, e.g. SCID or nod/SCID. See Brams et al., *J Immunol*, 160: 2051-2058 [1998]; Carballido et al., *Nat Med*, 6: 103-106 [2000]. In one approach, engraftment of human fetal tissue into SCID mice (SCID-hu) results in long-term hematopoiesis and human T-cell development [McCune et al., *Science* 241:1532-1639 (1988); Ifversen et al., *Sem Immunol* 8:243-248 (1996)]. Any humoral immune response in these chimeric mice is completely dependent on co-development of T-cells in the animals [Martensson et al., *Immunol* 83:1271-179 (1994)]. In an alternative approach, human peripheral blood lymphocytes are transplanted intraperitoneally (or otherwise) into SCID mice [Mosier et al., *Nature* 335:256-259 (1988)]. When the transplanted cells are treated with either a priming agent, such as Staphylococcal Enterotoxin A (SEA) [Martensson et al., *Immunol* 84: 224-230 (1995)], or anti-human CD40 monoclonal antibodies [Murphy et al., *Blood* 86:1946-1953 (1995)], higher levels of B cell production are detected.

Alternatively, an entirely synthetic human heavy chain repertoire is created from unrearranged V gene segments by assembling each human VH segment with D segments of random nucleotides together with a human J segment [Hoogenboom et al., *J Mol Biol* 227:381-388 (1992)]. Likewise, a light chain repertoire is constructed by combining each human V segment with a J segment [Griffiths et al., *EMBO J.* 13:3245-3260 (1994)]. Nucleotides encoding the complete antibody (i.e., both heavy and light chains) are linked as a single chain Fv fragment and this polynucleotide is ligated to a nucleotide encoding a filamentous phage minor coat protein. When this fusion protein is expressed on the surface of the phage, a polynucleotide encoding a specific antibody is identified by selection using an immobilized antigen.

In still another approach, antibody fragments are assembled as two Fab fragments by fusion of one chain to a phage protein and secretion of the other into bacterial periplasm [Hoogenboom et al., *Nucl Acids Res* 19:4133-4137 [1991]; Barbas et al., *Proc Natl Acad Sci (USA)* 88:7978-7982 (1991)].

Large-scale production of chimeric, humanized, CDR-grafted, and fully human antibodies, or antigen-binding fragments thereof, are typically produced by recombinant methods. Polynucleotide molecule(s) encoding the heavy and light chains of each antibody or antigen-binding fragments thereof, can be introduced into host cells and expressed using materials and procedures described herein. In a preferred embodiment, the antibodies are produced in mammalian host cells, such as CHO cells. Details of such production are described herein.

The specific binding agents of the present invention, such as the antibodies, antibody fragments, and antibody derivatives of the invention can further comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

In one embodiment, the specific binding agents of the present invention, such as the antibodies, antibody fragments, and antibody derivatives of the invention comprise an IgG.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

The specific binding agents of the present invention, such as the antibodies, antibody fragments, and antibody derivatives of the invention may comprise the IgG1 heavy chain constant domain or a fragment of the IgG1 heavy chain domain. The antibodies, antibody fragments, and antibody derivatives of the invention may further comprise the constant light chain kappa or lambda domains or a fragment of these. Light chain constant regions and polynucleotides encoding them are provided herein below. In another embodiment, the antibodies, antibody fragments, and antibody derivatives of the invention further comprise a heavy chain constant domain, or a fragment thereof, such as the IgG2 heavy chain constant region also shown herein below.

The nucleic acid (DNA) encoding constant heavy and constant light chain domains, and the amino acids sequences of heavy and light chain domains are provided herein below. Lambda variable domains can be fused to lambda constant domains and kappa variable domains can be fused to kappa constant domains.

```
IgG2 Heavy Constant domain DNA (SEQ ID NO: 41):
gctagcaccaagggcccatcggtcttccccctggcgccctgctccag
gagcacctccgagagcacagcggccctgggctgcctggtcaaggact
acttccccgaaccggtgacggtgtcgtggaactcaggcgctctgacc
agcggcgtgcacaccttcccagctgtcctacagtcctcaggactcta
ctccctcagcagcgtggtgaccgtgccctccagcaacttcggcaccc
agacctacacctgcaacgtagatcacaagcccagcaacaccaaggtg
gacaagacagttgagcgcaaatgttgtgtcgagtgccaccgtgccc
agcaccacctgtggcaggaccgtcagtcttcctcttcccccccaaaac
ccaaggacaccctcatgatctcccggacccctgaggtcacgtgcgtg
gtggtggacgtgagccacgaagacccccgaggtccagttcaactggta
cgtggacggcgtggaggtgcataatgccaagacaaagccacgggagg
agcagttcaacagcacgttccgtgtggtcagcgtcctcaccgttgtg
caccaggactggctgaacggcaaggagtacaagtgcaaggtctccaa
caaaggcctcccagccccccatcgagaaaaccatctccaaaaccaaag
ggcagccccgagaaccacaggtgtacaccctgcccccatcccggag
gagatgaccaagaaccaggtcagcctgacctgcctggtcaaaggctt
ctaccccagcgacatcgccgtggagtgggagagcaatgggcagccgg
agaacaactacaagaccacacctcccatgctggactccgacggctcc
ttcttcctctacagcaagctcaccgtggacaagagcaggtggcagca
ggggaacgtcttctcatgctccgtgatgcatgaggctctgcacaacc
actacacgcagaagagcctctccctgtctccgggtaaatga IgG2 Heavy Constant domain Protein
(SEQ ID NO: 42):
ASTKGPSVFPLAPCSRSTSESTAALGCLVKDYFPEPVTVSWNSGALT
SGVHTFPAVLQSSGLYSLSSVVTVPSSNFGTQTYTCNVDHKPSNTKV
DKTVERKCCVECPPCPAPPVAGPSVFLFPPKPKDTLMISRTPEVTCV
VVDVSHEDPEVQFNWYVDGVEVHNAKTKPREEQFNSTFRVVSVLTVV
HQDWLNGKEYKCKVSNKGLPAPIEKTISKTKGQPREPQVYTLPPSRE
EMTKNQVSLTCLVKGFYPSDIAVEWESNGQPENNYKTTPPMLDSDGS
FFLYSKLTVDKSRWQQGNVFSCSVMHEALHNHYTQKSLSLSPGK Kappa Light Constant domain DNA (SEQ ID NO: 43):
cgtacggtggctgcaccatctgtcttcatcttcccgccatctgatga
gcagttgaaatctggaactgcctctgttgtgtgcctgctgaataact
tctatcccagagaggccaaagtacagtggaaggtggataacgccctc
caatcgggtaactcccaggagagtgtcacagagcaggacagcaagga
cagcacctacagcctcagcagcaccctgacgctgagcaaagcagact
acgagaaacacaaagtctacgcctgcgaagtcacccatcagggcctg
agctcgcccgtcacaaagagcttcaacaggggagagtgttag Kappa Light Constant domain Protein
(SEQ ID NO: 44):
RTVAAPSVFIFPPSDEQLKSGTASVVCLLNNFYPREAKVQWKVDNAL
QSGNSQESVTEQDSKDSTYSLSSTLTLSKADYEKHKVYACEVTHQGL
SSPVTKSFNRGEC Lambda Light Constant domain DNA
(SEQ ID NO: 45):
ggccaaccgaaagcggcgccctcggtcactctgttcccgccctcctc
tgaggagcttcaagccaacaaggccacactggtgtgtctcataagtg
acttctacccgggagccgtgacagtggcctggaaggcagatagcagc
cccgtcaaggcgggagtggagaccaccacaccctccaaacaaagcaa
caacaagtacgcggccagcagctatctgagcctgacgcctgagcagt
ggaagtcccacagaagctacagctgccaggtcacgcatgaagggagc
accgtggagaagacagtggcccctacagaatgttcatag Lambda Light Constant domain Protein
(SEQ ID NO: 46):
GQPKAAPSVTLFPPSSEELQANKATLVCLISDFYPGAVTVAWKADSS
PVKAGVETTTPSKQSNNKYAASSYLSLTPEQWKSHRSYSCQVTHEGS
TVEKTVAPTECS
```

The specific binding agents of the present invention, such as the antibodies, antibody fragments, and antibody derivatives of the invention include those comprising, for example, the variable domain combinations H6L7, H5L7, H4L13, H11L7, H4L7, H10L7, H5L6, H2L7, H5L8, H6L8, H3L7, H5L4, H4L12, H6L6, H4L2, H4L6, H4L4, H5L11, H5L1, H4L11, H5L12, H5L9 having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407 (incorporated by reference herein) to alleviate a tendency to form intra-H chain disulfide bonds that can lead to heterogeneity in the IgG4 antibodies.

Additional Useful Sequence Information

The following sequences of the IgG1, IgG2, IgG3, and IgG4 isotypes are used in combination with the variable heavy chain sequences of the antibodies of the present invention to make a specific desired isotype of said antibody:

```
Human IgG1
ASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKV
DKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSV
LTVLHQDWLNGKEYKCKVSNKALPAPIEKTISKAKGQPREPQVYTLP
PSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG
K Human IgG2
ASTKGPSVFPLAPCSRSTSESTAALGCLVKDYFPEPVTVSWNSGALT
SGVHTFPAVLQSSGLYSLSSVVTVPSSNFGTQTYTCNVDHKPSNTKV
DKTVERKCCVECPPCPAPPVAGPSVFLFPPKPKDTLMISRTPEVTCV
VVDVSHEDPEVQFNWYVDGVEVHNAKTKPREEQFNSTFRVVSVLTVV
HQDWLNGKEYKCKVSNKGLPAPIEKTISKTKGQPREPQVYTLPPSRE
EMTKNQVSLTCLVKGFYPSDIAVEWESNGQPENNYKTTPPMLDSDGS
FFLYSKLTVDKSRWQQGNVFSCSVMHEALHNHYTQKSLSLSPGK Human IgG3
ASTKGPSVFPLAPCSRSTSGGTAALGCLVKDYFPEPVTVSWNSGALT
SGVHTFPAVLQSSGLYSLSSVVTVPSSSLGTQTYTCNVNHKPSNTKV
DKRVELKTPLGDTTHTCPRCPEPKSCDTPPPCPRCPEPKSCDTPPPC
PRCPEPKSCDTPPPCPRCPAPELLGGPSVFLFPPKPKDTLMISRTPE
VTCVVVDVSHEDPEVQFKWYVDGVEVHNAKTKPREEQYNSTFRVVSV
LTVLHQDWLNGKEYKCKVSNKALPAPIEKTISKTKGQPREPQVYTLP
PSREEMTKNQVSLTCLVKGFYPSDIAVEWESSGQPENNYNTTPPMLD
SDGSFFLYSKLTVDKSRWQQGNIFSCSVMHEALHNRFTQKSLSLSPG
K Human IgG4
ASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKV
DKRVESKYGPPCPSCPAPEFEGGPSVFLFPPKPKDTLMISRTPEVTC
VVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDG
SFFLYSRLTVDKSRWQEGNVFSCSVMHEALHNHYTQKSLSLSLGK
```

HC Sequences of the Antibodies of the Present Invention as an IgG2

The following sequences represent the heavy chain sequences of the antibodies of the present invention as IgG2 isotype. The light chain sequences remain the same, which are provided in the Examples. The underlined sequence portions represent the IgG2 sequences:

H2
EVQLVQSGGGVVQPGRSLRLSCAASGFTFSSYGMHWVRQAPGKGLEW
VSYISSSGSTIEYADSVKGRFTISRDNAKNSLYLQMNSLRAEDTAVY
YCARDLLDYDILTGYGYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H3
EVQLVQSGGGVVQPGRSLRLSCAASGFTFSSYGMHWVRQAPGKGLEW
VSYISSSGSTIQYADSVKGRFTISRDNAKNSLYLQMNSLRAEDTAVY
YCARDLLDYDILTGYGYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H6
EVQLVQSGGGVVQPGRSLRLSCAASGFTFSSYGMHWVRQAPGKGLEW
VSYISSSGSTIYYADSVKGRFTISRDNAKNSLYLQMNSLRAEDTAVY
YCARDLLDYDIYTGYGYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H10
EVQLVQSGGGVVQPGRSLRLSCAASGFTFSSYGMHWVRQAPGKGLEW
VSYISSSGSTIYYADSVKGRFTISRDNAKNSLYLQMNSLRAEDTAVY
YCARDLLDYDILTGYGLWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H11
EVQLVQSGGGVVQPGRSLRLSCAASGFTFSSYGMHWVRQAPGKGLEW
VSYISSSGSTIYYADSVKGRFTISRDNAKNSLYLQMNSLRAEDTAVY
YCARDLLDYDILTGYGMWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H4
EVQLVQSGGGVVQPGRSLRLSCAASGFTFSSYGMHWVRQAPGKGLEW
VSYISSSGSTIYYADSVKGRFTISRDNAKNSLYLQMNSLRAEDTAVY
YCARDLLDYDLLTGYGYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

H5
EVQLVQSGGGVVQPGRSLRLSCAASGFTFSSYGMHWVRQAPGKGLEW
VSYISSSGSTIYYADSVKGRFTISRDNAKNSLYLQMNSLRAEDTAVY
YCARDLLDYDIWTGYGYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PAPIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK

Fusion Partners of Specific Binding Agents

In a further embodiment of the invention, the polypeptides comprising the amino acid sequence variable domains of Ang-2 antibodies, such as a heavy chain variable region with an amino acid sequence as described herein or a light chain variable region with an amino acid sequence as described herein, may be fused at either the N-terminus or the C-terminus to one or more domains of an Fc region of human IgG. When constructed together with a therapeutic protein such as the Fab of an Ang-2-specific antibody, an Fc domain can provide longer half-life or incorporate such functions as Fc receptor binding, Protein A binding, complement fixation and perhaps even placental transfer. [Capon et al., Nature, 337: 525-531 (1989)].

In one example, the antibody hinge, CH2 and CH3 regions may be fused at either the N-terminus or C-terminus of the specific binding agent polypeptides such as an anti-Ang-2 Fab or Fv fragment (obtained, e.g., from a phage display library) using methods known to the skilled artisan. The resulting fusion protein may be purified by use of a Protein A or Protein G affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, decrease aggregation problems, etc. Other examples known in the art include those wherein the Fc region, which may be human or another species, or may be synthetic, is fused to the N-terminus of CD30L to treat Hodgkin's Disease, anaplastic lymphoma and T-cell leukemia (U.S. Pat. No. 5,480,981), the Fc region is fused to the TNF receptor to treat septic shock [Fisher et al., N Engl J Med, 334: 1697-1702 (1996)], and the Fc region is fused to the Cd4 receptor to treat AIDS [Capon et al., Nature, 337: 525-31 (1989)].

Catalytic antibodies are another type of fusion molecule and include antibodies to which one or more cytotoxic, or more generally one or more biologically active, moieties are attached to the specific binding agent. See, for example Rader et al., *Chem Eur J* 12:2091-2095 (2000). Cytotoxic agents of this type improve antibody-mediated cytotoxicity, and include such moieties as cytokines that directly or indirectly stimulate cell death, radioisotopes, chemotherapeutic drugs (including prodrugs), bacterial toxins (ex. *pseudomonas* exotoxin, diphtheria toxin, etc.), plant toxins (ex. ricin, gelonin, etc.), chemical conjugates (e.g., maytansinoid toxins, calechaemicin, etc.), radioconjugates, enzyme conjugates (RNase conjugates, antibody-directed enzyme/prodrug therapy [ADEPT)]), and the like. In one aspect, the cytotoxic agent can be "attached" to one component of a bi-specific or multi-specific antibody by binding of this agent to one of the alternative antigen recognition sites on the antibody. As an alternative, protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

Examples of such fusion proteins are immunogenic polypeptides, proteins with long circulating half lives, such as immunoglobulin constant regions, marker proteins, proteins or polypeptides that facilitate purification of the desired specific binding agent polypeptide, and polypeptide sequences that promote formation of multimeric proteins (such as leucine zipper motifs that are useful in dimer formation/stability).

This type of insertional variant generally has all or a substantial portion of the native molecule, linked at the N- or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-S-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

A particularly useful fusion construct may be one in which a specific binding agent peptide is fused to a hapten to enhance immunogenicity of a specific binding agent fusion construct which is useful, for example, in the production of anti-idiotype antibodies of the invention. Such fusion constructs to increase immunogenicity are well known to those of skill in the art, for example, a fusion of specific binding agent with a helper antigen such as hsp70 or peptide sequences such as from diphtheria toxin chain or a cytokine such as IL-2 will be useful in eliciting an immune response. In other embodiments, fusion construct can be made which will enhance the targeting of the antigen binding agent compositions to a specific site or cell.

Other fusion constructs including heterologous polypeptides with desired properties, e.g., an Ig constant region to prolong serum half-life or an antibody or fragment thereof for targeting also are contemplated. Other fusion systems produce polypeptide hybrids where it is desirable to excise the fusion partner from the desired polypeptide. In one embodiment, the fusion partner is linked to the recombinant specific binding agent polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The invention also provides fusion polypeptides comprising all or part of a variable domain of an Ang-2 antibody, such as a heavy chain variable region with an amino acid sequence as described herein or a light chain variable region with an amino acid sequence as described herein in combination with truncated tissue factor (tTF), a vascular targeting agent consisting of a truncated form of a human coagulation-inducing protein that acts as a tumor blood vessel clotting agent. The fusion of tTF to the anti-Ang-2 antibody, or fragments thereof may facilitate the delivery of anti-Ang-2 to target cells.

Variants of Specific Binding Agents

Variants of Specific Binding Agents of the present invention include insertion, deletion, and/or substitution variants. In one aspect of the invention, insertion variants are provided wherein one or more amino acid residues supplement a specific binding agent amino acid sequence. Insertions may be located at either or both termini of the protein, or may be positioned within internal regions of the specific binding agent amino acid sequence. Insertional variants with additional residues at either or both termini can include, for example, fusion proteins and proteins including amino acid tags or labels. Insertion variants include specific binding agent polypeptides wherein one or more amino acid residues are added to a specific binding agent amino acid sequence, or fragment thereof.

Variant products of the invention also include mature specific binding agent products. Such specific binding agent products have the leader or signal sequences removed, however the resulting protein has additional amino terminal residues as compared to wild-type Ang-2 polypeptide. The additional amino terminal residues may be derived from another protein, or may include one or more residues that are not identifiable as being derived from a specific protein. Specific binding agent products with an additional methionine residue at position −1 (Met$^{-1}$-specific binding agent) are contemplated, as are specific binding agent products with additional methionine and lysine residues at positions −2 and −1 (Met$^-$2-Lys$^{-1}$-specific binding agent). Variants of specific binding agents having additional Met, Met-Lys, Lys residues (or one or more basic residues in general) are particularly useful for enhanced recombinant protein production in bacterial host cells.

The invention also embraces specific binding agent variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position −1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins as described above, wherein the amino and/or carboxy termini of the specific binding agent-polypeptide is fused to another polypeptide, a fragment thereof, or amino acid sequences which are not generally recognized to be part of any specific protein sequence.

In another aspect, the invention provides deletion variants wherein one or more amino acid residues in a specific binding agent polypeptide are removed. Deletions can be effected at one or both termini of the specific binding agent polypeptide, or from removal of one or more residues within the specific binding agent amino acid sequence. Deletion variants necessarily include all fragments of a specific binding agent polypeptide.

Antibody fragments include those portions of the antibody that bind to an epitope on the antigen polypeptide. Examples of such fragments include Fab and F(ab")$_2$ fragments generated, for example, by enzymatic or chemical cleavage of full-length antibodies. Other binding fragments include those generated by recombinant DNA techniques, such as the expression of recombinant plasmids containing nucleic acid sequences encoding antibody variable regions. The invention also embraces polypeptide fragments of an Ang-2 binding agent wherein the fragments maintain the ability to specifically bind an Ang-2 polypeptide. Fragments comprising at least 5, 10, 15, 20, 25, 30, 35, 40, 45 or 50 or more consecutive amino acids of a peptide or polypeptide of the invention are comprehended herein. Preferred polypeptide fragments display immunological properties unique to or specific for the antigen-binding agent so of the invention. Fragments of the invention having the desired immunological properties can be prepared by any of the methods well known and routinely practiced in the art.

In still another aspect, the invention provides substitution variants of specific binding agents of the invention. Substitution variants are generally considered to be "similar" to the original polypeptide or to have a certain "percent identity" to the original polypeptide, and include those polypeptides wherein one or more amino acid residues of a polypeptide are removed and replaced with alternative residues. In one aspect, the substitutions are conservative in nature, however, the invention embraces substitutions that are also non-conservative.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine the relatedness or percent identity of two polypeptides are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3)(1978) for the PAM 250 comparison matrix; Henikoff et al., *Proc. Natl. Acad. Sci.* USA, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence comparisons include the following:

Algorithm: Needleman et al., supra (1970);

Comparison matrix: matches=+10, mismatch=0

Gap Penalty: 50

Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose.

The amino acids may have either L or D stereochemistry (except for Gly, which is neither L nor D) and the polypeptides and compositions of the present invention may comprise a combination of stereochemistries. However, the L stereochemistry is preferred. The invention also provides reverse molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asn | Glu |
| Cys | Ser, Ala | Ser |
| Gln | Asn, Glu, Asp | Asn |
| Glu | Asp, Asn, Gln | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |

TABLE 1-continued

Amino Acid Substitutions

| Original Residues | Exemplary Substitutions | Preferred Substitutions |
|---|---|---|
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.,* 7(4):422-427 (1996), Chou et al., *Biochemistry,* 13(2):222-245 (1974); Chou et al., *Biochemistry,* 113(2):211-222 (1974); Chou et al., *Adv. Enzymol. Relat. Areas Mol. Biol.,* 47:45-148 (1978); Chou et al., *Ann. Rev. Biochem.,* 47:251-276 and Chou et al., *Biophys. J.,* 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.,* 27(1):244-247 (1999). It has been suggested (Brenner et al., *Curr. Op. Struct. Biol.,* 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.,* 7(3): 377-87 (1997); Sippl et al., *Structure,* 4(1):15-19 (1996)), "profile analysis" (Bowie et al., *Science,* 253:164-170 (1991); Gribskov et al., *Meth. Enzym.,* 183:146-159 (1990); Gribskov et al., *Proc. Nat. Acad. Sci.,* 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The specific binding agent molecules of this invention that are polypeptide or peptide substitution variants may have up to about ten to twelve percent of the original amino acid sequence replaced. For antibody variants, the heavy chain may have 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid replaced, while the light chain may have 25, 24, 23, 22, 21, 20, 19, 18, 17, 16, 15, 14, 13, 12, 11, 10, 9, 8, 7, 6, 5, 4, 3, 2, or 1 amino acid replaced.

Derivatives of Specific Binding Agents

The invention also provides derivatives of specific binding agent polypeptides. Derivatives include specific binding agent polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life of a specific binding agent polypeptide, or may be designed to improve targeting capacity for the polypeptide to desired cells, tissues, or organs.

The invention further embraces derivative binding agents covalently modified to include one or more water soluble polymer attachments such as polyethylene glycol, polyoxyethylene glycol, or polypropylene glycol as described U.S. Pat. Nos. 4,640,835, 4,496,689, 4,301,144, 4,670,417, 4,791, 192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers. Particularly preferred are specific binding agent products covalently modified with polyethylene glycol (PEG) subunits. Water-soluble polymers may be bonded at specific positions, for example at the amino terminus of the specific binding agent products, or randomly attached to one or more side chains of the polypeptide. The use of PEG for improving the therapeutic capacity for specific binding agent, and for humanized antibodies in particular, is described in U.S. Pat. No. 6,133, 426 to Gonzales et al., issued Oct. 17, 2000.

Target Sites for Antibody Mutagenesis

Certain strategies can be employed to manipulate inherent properties of an Ang-1 and/or Ang-2-specific antibody, such as the affinity of the antibody for its target. These strategies include the use of site-specific or random mutagenesis of the polynucleotide molecule encoding the antibody to generate antibody variants, followed by a screening step designed to recover antibody variants that exhibit the desired change, e.g. increased or decreased affinity.

The amino acid residues most commonly targeted in mutagenic strategies are those in the CDRs. As described supra, these regions contain the residues that actually interact with Ang-1 and/or Ang-2 and other amino acids that affect the spatial arrangement of these residues. However, amino acids in the framework regions of the variable domains outside the CDR regions have also been shown to make substantial contributions to the antigen-binding properties of the antibody, and can be targeted to manipulate such properties. See Hudson, *Curr Opin Biotech*, 9:395-402 (1999) and references therein.

Smaller and more effectively screened libraries of antibody variants can be produced by restricting random or site-directed mutagenesis to sites in the CDRs that correspond to areas prone to "hyper-mutation" during the somatic affinity maturation process. See Chowdhury and Pastan, *Nature Biotech*, 17: 568-572 [1999] and references therein. The types of DNA elements known to define hyper-mutation sites in this manner include direct and inverted repeats, certain consensus sequences, secondary structures, and palindromes. The consensus DNA sequences include the tetrabase sequence Purine-G-Pyrimidine-A/T (i.e. A or G-G-C or T-A or T) and the serine codon AGY (wherein Y can be a C or a T).

Thus, an embodiment of the present invention includes mutagenic strategies with the goal of increasing the affinity of an antibody for its target. These strategies include mutagenesis of the entire variable heavy and light chain, mutagenesis of the CDR regions only, mutagenesis of the consensus hypermutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished though solving the structure of the antibody in question, and the antibody-ligand complex, through techniques known to those skilled in the art, such as X-ray crystallography. Various methods based on analysis and characterization of such antibody crystal structures are known to those of skill in the art and can be employed, although not definitive, to approximate the CDR regions. Examples of such commonly used methods include the Kabat, Chothia, AbM and contact definitions.

The Kabat definition is based on the sequence variability and is the most commonly used definition to predict CDR regions. [Johnson and Wu, *Nucleic Acids Res*, 28: 214-8 (2000)]. The Chothia definition is based on the location of the structural loop regions. [Chothia et al., *J Mol Biol*, 196: 901-17 (1986); Chothia et al., *Nature*, 342: 877-83 (1989)]. The AbM definition is a compromise between the Kabat and Chothia definition. AbM is an integral suite of programs for antibody structure modeling produced by Oxford Molecular Group [Martin et al., *Proc Natl Acad Sci (USA)* 86:9268-9272 (1989); Rees, et al., ABM™, a computer program for modeling variable regions of antibodies, Oxford, UK; Oxford Molecular, Ltd.]. The AbM suite models the tertiary structure of an antibody from primary sequencing using a combination of knowledge databases and ab initio methods. An additional definition, known as the contact definition, has been recently introduced. [MacCallum et al., *J Mol Biol*, 5:732-45 (1996)]. This definition is based on an analysis of the available complex crystal structures.

By convention, the CDR regions in the heavy chain are typically referred to as H1, H2 and H3 and are numbered sequentially in order counting from the amino terminus to the carboxy terminus. The CDR regions in the light chain are typically referred to as L1, L2 and L3 and are numbered sequentially in order counting from the amino terminus to the carboxy terminus.

The CDR-H1 is approximately 10 to 12 residues in length and typically starts 4 residues after a Cys according to the Chothia and AbM definitions or typically 5 residues later according to the Kabat definition. The H1 is typically followed by a Trp, typically Trp-Val, but also Trp-Ile, or Trp-Ala. The length of H1 is approximately 10 to 12 residues according to the AbM definition while the Chothia definition excludes the last 4 residues.

The CDR-H2 typically starts 15 residues after the end of H1 according to the Kabat and AbM definition. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of the H2 is approximately 16 to 19 residues where the AbM definition predicts the length to be typically 9 to 12 residues.

The CDR-H3 typically starts 33 residues after the end of H2 and is typically preceded by the amino acid sequence (typically Cys-Ala-Arg). The H3 is typically followed by the amino acid sequence-Gly. The length of H3 can be anywhere between 3 to 25 residues.

The CDR-L1 typically starts at approximately residue 24 and will typically follow a Cys. The residue after the CDR-L1 is always a Trp and will typically begin the sequence Trp-Tyr-Gln, Trp-Leu-Gln, Trp-Phe-Gln, or Trp-Tyr-Leu. The length of CDR-L1 is approximately 10 to 17 residues. The punitive CDR-L1 for the antibodies of the invention follows this pattern exactly with a Cys residue followed by 15 amino acids then Trp-Tyr-Gln.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-XXX-Gly. The length of L3 is approximately 7 to 11 residues.

Various methods for modifying antibodies have been described in the art. For example, U.S. Pat. No. 5,530,101 (to Queen et al., Jun. 25, 1996) describes methods to produce humanized antibodies wherein the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to affect binding affinity, such as one or more amino acids which are immediately adjacent to a CDR in the donor immunoglobulin or those within about 3 angstroms as predicted by molecular modeling. The heavy and light chains may each be designed by using any one or all of various position criteria. When combined into an intact antibody, the humanized immunoglobulins of the present invention will be substantially non-immunogenic in humans and retain substantially the same affinity as the donor immunoglobulin to the antigen, such as a protein or other compound containing an epitope. See also, related methods in U.S. Pat. No. 5,693,761 to Queen, et al., issued Dec. 2, 1997 ("Polynucleotides encoding improved humanized immunoglobulins"); U.S. Pat. No. 5,693,762 to Queen, et al., issued Dec. 2, 1997 ("Humanized Immunoglobulins"); U.S. Pat. No. 5,585,089 to Queen, et al. issued Dec. 17, 1996 ("Humanized Immunoglobulins").

In one example, U.S. Pat. No. 5,565,332 to Hoogenboom et al. issued Oct. 15, 1996 ("Production of chimeric antibodies—a combinatorial approach") describes methods for the production of antibodies, and antibody fragments which have similar binding specificity as a parent antibody but which have increased human characteristics. Humanized antibodies are obtained by chain shuffling, using, for example, phage display technology, and a polypeptide comprising a heavy or light chain variable domain of a non-human antibody specific for an antigen of interest is combined with a repertoire of human complementary (light or heavy) chain variable domains. Hybrid pairings that are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and used in a second humanizing shuffling step. Alternatively, this second step is eliminated if the hybrid is already of sufficient human character to be of therapeutic value. Methods of modification to increase human character are also described. See also Winter, *FEBS Letts* 430:92-92 (1998).

As another example, U.S. Pat. No. 6,054,297 to Carter et al., issued Apr. 25, 2000 describes a method for making humanized antibodies by substituting a CDR amino acid sequence for the corresponding human CDR amino acid sequence and/or substituting a FR amino acid sequence for the corresponding human FR amino acid sequences.

As another example, U.S. Pat. No. 5,766,886 to Studnicka et al., issued Jun. 16, 1998 ("Modified antibody variable domains") describes methods for identifying the amino acid residues of an antibody variable domain which may be modified without diminishing the native affinity of the antigen binding domain while reducing its immunogenicity with respect to a heterologous species and methods for preparing these modified antibody variable domains which are useful for administration to heterologous species. See also U.S. Pat. No. 5,869,619 to Studnicka issued Feb. 9, 1999.

As discussed, modification of an antibody by any of the methods known in the art is typically designed to achieve increased binding affinity for an antigen and/or reduce immunogenicity of the antibody in the recipient. In one approach, humanized antibodies can be modified to eliminate glycosylation sites in order to increase affinity of the antibody for its cognate antigen [Co et al., *Mol Immunol* 30:1361-1367 (1993)]. Techniques such as "reshaping," "hyperchimerization," and "veneering/resurfacing" have produced humanized antibodies with greater therapeutic potential. [Vaswami et al., Annals of *Allergy, Asthma, & Immunol* 81:105 (1998); Roguska et al., *Prot Engineer* 9:895-904 (1996)]. See also U.S. Pat. No. 6,072,035 to Hardman et al., issued Jun. 6, 2000, which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., *J Immunol* 62(6): 3663-71 (1999).

In many instances, humanizing antibodies result in a loss of antigen binding capacity. It is therefore preferable to "back mutate" the humanized antibody to include one or more of the amino acid residues found in the original (most often rodent) antibody in an attempt to restore binding affinity of the antibody. See, for example, Saldanha et al., *Mol Immunol* 36:709-19 (1999).

Non-Peptide Specific Binding Agent Analogs/Protein Mimetics

Furthermore, nonpeptide specific binding agent analogs of peptides that provide a stabilized structure or lessened biodegradation, are also contemplated. Specific binding agent peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind Ang-1 and/or Ang-2. In one aspect, the resulting analog/mimetic exhibits increased binding affinity for Ang-1 and/or Ang-2. One example of methods for preparation of nonpeptide mimetic analogs from specific binding agent peptides is described in Nachman et al., *Regul Pept* 57:359-370 (1995). If desired, the specific binding agent peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The specific binding agent peptides also can be modified to create peptide derivatives by forming covalent or noncovalent complexes with other moieties. Covalently-bound complexes can be prepared by linking the chemical moieties to functional groups on the side chains of amino acids comprising the specific binding agent peptides, or at the N- or C-terminus.

In particular, it is anticipated that the specific binding agent peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. No. 3,817,837; U.S. Pat. No. 3,850,752; U.S. Pat. No. 3,996,345 and U.S. Pat. No. 4,277,437. Other labels that will be useful include but are not limited to radioactive labels, fluorescent labels and chemiluminescent labels. U.S. patents concerning use of such labels include for example U.S. Pat. No. 3,817,837; U.S. Pat. No. 3,850,752; U.S. Pat. No. 3,939,350 and U.S. Pat. No. 3,996,345. Any of the peptides of the present invention may comprise one, two, or more of any of these labels.

Methods of Making Specific Binding Agents

Specific binding agents of the present invention that are proteins can be prepared by chemical synthesis in solution or on a solid support in accordance with conventional techniques. The current limit for solid phase synthesis is about 85-100 amino acids in length. However, chemical synthesis techniques can often be used to chemically ligate a series of smaller peptides to generate full length polypeptides. Various automatic synthesizers are commercially available and can be used in accordance with known protocols. See, for example, Stewart and Young, Solid Phase Peptide Synthesis, 2d. ed., Pierce Chemical Co., (1984); Tam et al., *J Am Chem Soc*, 105:6442, (1983); Merrifield, *Science*, 232:341-347, (1986); and Barany and Merrifield, The Peptides, Gross and Meienhofer, eds, Academic Press, New York, 1-284; Barany et al., Int. J. Peptide Protein Res., 30, 705-739 (1987); and U.S. Pat. No. 5,424,398), each incorporated herein by reference.

Solid phase peptide synthesis methods use a copoly(styrene-divinylbenzene) containing 0.1-1.0 mM amines/g polymer. These methods for peptide synthesis use butyloxycarbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide (See, Coligan et al., Current Protocols in Immunology, Wiley Interscience, 1991, Unit 9). On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hour at 0° C.). After evaporation of the reagents, the specific binding agent peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous specific binding agent peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Chemical synthesis of anti-Ang-1 and/or anti-Ang-2 antibodies, derivatives, variants, and fragments thereof, as well as other protein-based Ang-2 binding agents permits incorporation of non-naturally occurring amino acids into the agent.

Recombinant DNA techniques are a convenient method for preparing full length antibodies and other large proteinaceous specific binding agents of the present invention, or fragments thereof. A cDNA molecule encoding the antibody or fragment may be inserted into an expression vector, which can in turn be inserted into a host cell for production of the antibody or fragment. It is understood that the cDNAs encoding such antibodies may be modified to vary from the "original" cDNA (translated from the mRNA) to provide for codon degeneracy or to permit codon preference usage in various host cells.

Generally, a DNA molecule encoding an antibody can be obtained using procedures described herein in the Examples. Where it is desirable to obtain Fab molecules or CDRs that are related to the original antibody molecule, one can screen a suitable library (phage display library; lymphocyte library, etc.) using standard techniques to identify and clone related Fabs/CDRs. Probes used for such screening may be full length or truncated Fab probes encoding the Fab portion of the original antibody, probes against one or more CDRs from the Fab portion of the original antibody, or other suitable probes. Where DNA fragments are used as probes, typical hybridization conditions are those such as set forth in Ausubel et. al. (Current Protocols in Molecular Biology, Current Protocols Press [1994]). After hybridization, the probed blot can be washed at a suitable stringency, depending on such factors as probe size, expected homology of probe to clone, the type of library being screened, and the number of clones being screened. Examples of high stringency screening are 0.1× SSC, and 0.1 percent SDS at a temperature between 50-65° C.

A variety of expression vector/host systems may be utilized to contain and express the polynucleotide molecules encoding the specific binding agent polypeptides of the invention. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian cells that are useful in recombinant specific binding agent protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells, as well as hybridoma cell lines as described herein. Mammalian cells are preferred for preparation of those specific binding agents such as antibodies and antibody fragments that are typically glycosylated and require proper refolding for activity. Preferred mammalian cells include CHO cells, hybridoma cells, and myeloid cells.

Some exemplary protocols for the recombinant expression of the specific binding agent proteins are described herein below.

The term "expression vector" refers to a plasmid, phage, virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant specific binding agent protein is expressed without a leader or transport sequence, it may include an amino terminal methionine residue. This residue may or may not be subsequently cleaved from the expressed recombinant protein to provide a final specific binding agent product.

For example, the specific binding agents may be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted specific binding agent peptide is purified from the yeast growth medium by, e.g., the methods used to purify the peptide from bacterial and mammalian cell supernatants.

Alternatively, the cDNA encoding the specific binding agent peptide may be cloned into the baculovirus expression vector pVL1393 (PharMingen, San Diego, Calif.). This vector can be used according to the manufacturer's directions (PharMingen) to infect *Spodoptera frugiperda* cells in sF9 protein-free media and to produce recombinant protein. The specific binding agent protein can be purified and concentrated from the media using a heparin-Sepharose column (Pharmacia).

Alternatively, the peptide may be expressed in an insect system. Insect systems for protein expression are well known to those of skill in the art. In one such system, *Autographa californica* nuclear polyhedrosis virus (AcNPV) can be used as a vector to express foreign genes in *Spodoptera frugiperda* cells or in *Trichoplusia* larvae. The specific binding agent peptide coding sequence can be cloned into a nonessential region of the virus, such as the polyhedrin gene, and placed under control of the polyhedrin promoter. Successful insertion of the specific binding agent peptide will render the polyhedrin gene inactive and produce recombinant virus lacking coat protein coat. The recombinant viruses can be used to infect *S. frugiperda* cells or *Trichoplusia* larvae in which peptide is expressed [Smith et al., *J Virol* 46: 584 (1983); Engelhard et al., *Proc Nat Acad Sci (USA)* 91: 3224-7 (1994)].

In another example, the DNA sequence encoding the specific binding agent peptide can be amplified by PCR and cloned into an appropriate vector for example, pGEX-3x (Pharmacia). The pGEX vector is designed to produce a fusion protein comprising glutathione-S-transferase (GST), encoded by the vector, and a specific binding agent protein encoded by a DNA fragment inserted into the vector's cloning site. The primers for the PCR can be generated to include for example, an appropriate cleavage site. Where the specific binding agent fusion moiety is used solely to facilitate expression or is otherwise not desirable as an attachment to the peptide of interest, the recombinant specific binding agent fusion protein may then be cleaved from the GST portion of the fusion protein. The pGEX-3x/specific binding agent peptide construct is transformed into *E. coli* XL-1 Blue cells (Stratagene, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

Expression of polynucleotides encoding anti-Ang-1 and/or anti-Ang-2 antibodies and fragments thereof using the recombinant systems described above may result in production of antibodies or fragments thereof that must be "refolded" (to properly create various disulphide bridges) in order to be biologically active. Typical refolding procedures for such antibodies are set forth in the Examples herein and in the following section.

Specific binding agents made in bacterial cells may be produced as an insoluble inclusion body in the bacteria, can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000×g. The specific binding agent-containing pellet can be resuspended in 50 mM Tris, pH 8, and 10 mM EDTA, layered over 50% glycerol, and centrifuged for 30 min. at 6000×g. The pellet can be resuspended in standard phosphate buffered saline solution (PBS) free of $Mg^{++}$ and $Ca^{++}$. The specific binding agent can be further purified by fractionating the resuspended pellet in a denaturing SDS polyacrylamide gel (Sambrook et al., supra). The gel can be soaked in 0.4 M KCl to visualize the protein, which can be excised and electroeluted in gel-running buffer lacking SDS. If the GST fusion protein is produced in bacteria, as a soluble protein, it can be purified using the GST Purification Module (Pharmacia).

Mammalian host systems for the expression of the recombinant protein are well known to those of skill in the art. Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, WI38, as well as hybridoma cell lines, and the like have specific cellular machinery and characteristic mechanisms for such post-translational activities and can be chosen to ensure the correct modification and processing of the introduced, foreign protein.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Purification and Refolding of Specific Binding Agents

In some cases, the specific binding agents produced using procedures described above may need to be "refolded" and oxidized into a proper tertiary structure and generating disulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for dusykfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

It will be desirable to purify specific binding agent proteins or variants thereof of the present invention. Protein purification techniques are well known to those of skill in the art. These techniques involve, at one level, the crude fractionation of the polypeptide and non-polypeptide fractions. Having separated the specific binding agent polypeptide from other proteins, the polypeptide of interest can be further purified using chromatographic and electrophoretic techniques to achieve partial or complete purification (or purification to homogeneity). Analytical methods particularly suited to the preparation of a pure specific binding agent peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concerns the purification, and in particular embodiments, the substantial purification, of an encoded specific binding agent protein or peptide. The term "purified specific binding agent protein or peptide" as used herein, is intended to refer to a composition, isolatable from other components, wherein the specific binding agent protein or peptide is purified to any degree relative to its naturally-obtainable state. A purified specific binding agent protein or peptide therefore also refers to a specific binding agent protein or peptide, free from the environment in which it may naturally occur.

Generally, "purified" will refer to a specific binding agent composition that has been subjected to fractionation to remove various other components, and which composition substantially retains its expressed biological activity. Where the term "substantially purified" is used, this designation will refer to a specific binding agent composition in which the specific binding agent protein or peptide forms the major component of the composition, such as constituting about 50%, about 60%, about 70%, about 80%, about 90%, about 95% or more of the proteins in the composition.

Various methods for quantifying the degree of purification of the specific binding agent will be known to those of skill in the art in light of the present disclosure. These include, for example, determining the specific binding activity of an active fraction, or assessing the amount of specific binding agent polypeptides within a fraction by SDS/PAGE analysis. A preferred method for assessing the purity of a specific binding agent fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the expressed specific binding agent protein or peptide exhibits a detectable binding activity.

Various techniques suitable for use in specific binding agent protein purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified specific binding agent.

There is no general requirement that the specific binding agent always be provided in its most purified state. Indeed, it is contemplated that less substantially specific binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of specific binding agent protein product, or in maintaining binding activity of an expressed specific binding agent protein.

It is known that the migration of a polypeptide can vary, sometimes significantly, with different conditions of SDS/PAGE [Capaldi et al., *Biochem Biophys\Res Comm*, 76: 425 (1977)]. It will therefore be appreciated that under differing electrophoresis conditions, the apparent molecular weights of purified or partially purified specific binding agent expression products may vary.

Binding Assays

Immunological binding assays typically utilize a capture agent to bind specifically to and often immobilize the analyte target antigen. The capture agent is a moiety that specifically binds to the analyte. In one embodiment of the present invention, the capture agent is an antibody or fragment thereof that specifically binds Ang-2 and/or Ang-1. These immunological binding assays are well known in the art [see, Asai, ed., Methods in Cell Biology, Vol. 37, Antibodies in Cell Biology, Academic Press, Inc., New York (1993)].

Immunological binding assays frequently utilize a labeling agent that will signal the existence of the bound complex formed by the capture agent and antigen. The labeling agent can be one of the molecules comprising the bound complex; i.e. it can be labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species [see, generally Akerstrom, *J Immunol*, 135:2589-2542 (1985); and Chaubert, *Mod Pathol*, 10:585-591 (1997)].

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-Competitive Binding Assays:

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized antibodies then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. [See, Harlow and Lane, Antibodies, A Laboratory Manual, Ch 14, Cold Spring Harbor Laboratory, NY (1988), incorporated herein by reference].

B. Competitive Binding Assays:

Immunological binding assays can be of the competitive type. The amount of analyte present in the sample is measure indirectly by measuring the amount of an added analyte displaced, or competed away, from a capture agent by the analyte present in the sample. In one preferred competitive binding assay, a known amount of analyte, usually labeled, is added to the sample and the sample is then contacted with an antibody (the capture agent). The amount of labeled analyze bound to the antibody is inversely proportional to the concentration of analyte present in the sample. (See, Harlow and Lane, Antibodies, A Laboratory Manual, Ch 14, pp. 579-583, supra).

In another preferred competitive binding assay, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein. See, Harlow and Lane, Antibodies, A Laboratory Manual, Ch 14, supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for cross-reactivity determinations to permit a skilled artisan to determine if a protein or enzyme complex which is recognized by a specific binding agent of the invention is the desired protein and not a cross-reacting molecule or to determine whether the antibody is specific for the antigen and does not bind unrelated antigens. In assays of this type, antigen can be immobilized to a solid support and an unknown protein mixture is added to the assay, which will compete with the binding of the specific binding agents to the immobilized protein. The competing molecule also binds one or more antigens unrelated to the antigen. The ability of the proteins to compete with the binding of the specific binding agents antibodies to the immobilized antigen is compared to the binding by the same protein that was immobilized to the solid support to determine the cross-reactivity of the protein mix.

D. Other Binding Assays:

The present invention also provides Western blot methods to detect or quantify the presence of Ang-1 and/or Ang-2 in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or fragments thereof that specifically bind Ang-1 and/or Ang-2 and the resulting complex is detected. These antibodies may be directly labeled or alternatively may be subsequently detected using labeled antibodies that specifically bind to the antibody.

Binding assays to detect those Ang-1 and/or Ang-2 specific binding agents that disrupt Ang-2 binding to its receptor are set forth in the Examples herein.

Diagnostic Assays

The antibodies or antigen-binding fragments thereof of present invention are useful for the diagnosis of conditions or diseases characterized by expression of Ang-1 and/or Ang-2 or subunits, or in assays to monitor patients being treated with inducers of Ang-1 and/or Ang-2, its fragments, agonists or inhibitors of Ang-1 and/or Ang-2 activity. Diagnostic assays for Ang-1 and/or Ang-2 include methods utilizing a specific binding agent and a label to detect Ang-1 and/or Ang-2 in human body fluids or extracts of cells or tissues. The specific binding agents of the present invention can be used with or without modification. In a preferred diagnostic assay, the specific binding agents will be labeled by attaching, e.g., a label or a reporter molecule. A wide variety of labels and reporter molecules are known, some of which have been already described herein. In particular, the present invention is useful for diagnosis of human disease.

A variety of protocols for measuring Ang-1 and/or Ang-2 proteins using either polyclonal or monoclonal antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on Ang-1 and/or Ang-2 is preferred, but a competitive binding assay can be employed. These assays are described, for example, in Maddox et al., *J Exp Med*, 158:1211 [1983].

In order to provide a basis for diagnosis, normal or standard values for human Ang-1 and/or Ang-2 expression are usually established. This determination can be accomplished by combining body fluids or cell extracts from normal subjects, preferably human, with a specific binding agent, for example, an antibody, to Ang-1 and/or Ang-2, under conditions suitable for complex formation that are well known in the art. The amount of standard complex formation can be quantified by comparing the binding of the specific binding agents to known quantities of Ang-1 and/or Ang-2 protein, with both control and disease samples. Then, standard values obtained from normal samples can be compared with values obtained from samples from subjects potentially affected by disease. Deviation between standard and subject values suggests a role for Ang-1 and/or Ang-2 in the disease state.

For diagnostic applications, in certain embodiments, specific binding agents typically will be labeled with a detectable moiety. The detectable moiety can be any one that is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase, or horseradish peroxidase [Bayer et al., *Meth Enz,* 184: 138-163, (1990)].

Diseases

The present invention provides a specific binding agent that binds to Ang-1 and/or Ang-2 that is useful for the treatment of human diseases and pathological conditions. Agents that modulate Ang-1 and/or Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-1 and/or Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent that inhibits or decreases Ang-1 and/or Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells amenable to treatment according to the invention include, for example, ACTH-producing tumor, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with Ang-2 expression or activity are especially susceptible to being inhibited or even induced to regress by means of the invention.

The invention can also be practiced by including with a specific binding agent of the invention, such as an antibody, in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

The present invention thus provides compositions and methods useful for the treatment of a wide variety of cancers, including solid tumors and leukemias. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small lung cell carcinoma; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; tophoblastic tumor. Further, the following types of cancers may also be treated: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Another aspect of the present invention is using the materials and methods of the present invention to prevent and/or treat any hyperproliferative condition of the skin including psoriasis and contact dermatitis or other hyperproliferative diseases. It has been demonstrated that patients with psoriasis and contact dermatitis have elevated Ang-2 activity within these lesions [Ogoshi et al., *J. Inv. Dermatol.*, 110:818-23 (1998)]. Preferably, specific binding agents specific for Ang-2 will be used in combination with other pharmaceutical agents to treat humans that express these clinical symptoms. The specific binding agents can be delivered using any of the various carriers through routes of administration described herein and others that are well known to those of skill in the art.

Other aspects of the present invention include treating various retinopathies (including diabetic retinopathy and age-related macular degeneration) in which angiogenesis is involved, as well as disorders/diseases of the female reproductive tract such as endometriosis, uterine fibroids, and other such conditions associated with dysfunctional vascular proliferation (including endometrial microvascular growth) during the female reproductive cycle.

Still another aspect of the present invention relates to treating abnormal vascular growth including cerebral arteriovenous malformations (AVMs) gastrointestinal mucosal injury and repair, ulceration of the gastroduodenal mucosa in patients with a history of peptic ulcer disease, including ischemia resulting from stroke, a wide spectrum of pulmonary vascular disorders in liver disease and portal hypertension in patients with nonhepatic portal hypertension.

Another aspect of present invention is the prevention of cancers utilizing the compositions and methods provided by the present invention. Such reagents will include specific binding agents against Ang-2.

Pharmaceutical Compositions

Pharmaceutical compositions of Ang-1 and/or Ang-2 specific binding agents are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of a specific binding agent, such as an antibody, or a fragment, variant, derivative or fusion thereof as described herein, in admixture with a pharmaceutically acceptable agent. In a preferred embodiment, pharmaceutical compositions comprise antagonist specific binding agents that modulate partially or completely at least one biological activity of Ang-1 and/or Ang-2 in admixture with a pharmaceutically acceptable agent. Typically, the specific binding agents will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., *Biopolymers,* 22:547-556 (1983)], poly(2-hydroxyethyl-methacrylate) [Langer et al., *J Biomed Mater Res,* 15:167-277, (1981)] and [Langer et al., *Chem Tech,* 12:98-105 (1982)], ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., *Proc Natl Acad Sci (USA),* 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent which is a polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapy

Specific binding agents of the invention can be utilized in combination with other therapeutic in the treatment of Ang-1 and/or Ang-2 pathologies. These other therapeutics include, for example radiation treatment, chemotherapeutic agents, as well as other growth factors or inhibitors.

Chemotherapy treatment can employ anti-neoplastic agents including, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy can done in conjunction with the growth factors listed below or with agents that are designed to inhibit the growth factors listed below. The growth factors include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other are compositions can include known angiopoietins, for example Ang-1, -2, -4, -Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor-IA, bone morphogenic protein receptor IB, brain derived neurotrophic factor, ciliary neutrophic factor, ciliary neutrophic factor receptor, cytokine-induced neutrophil chemotactic factor-1, cytokine-induced neutrophil, chemotactic factor-2, cytokine-induced neutrophil chemotactic factor-2, endothelial cell growth factor, endothelin-1, epidermal growth factor, epithelial-derived neutrophil attractant, fibroblast growth factor-4, fibroblast growth factor-5, fibroblast growth factor-6, fibroblast growth factor-7, fibroblast growth factor-8, fibroblast growth factor-8b, fibroblast growth factor-8c, fibroblast growth factor-9, fibroblast growth factor-10, fibroblast growth factor acidic, fibroblast growth factor basic, glial cell line-derived neutrophic factor receptor-1, glial cell line-derived neutrophic factor receptor-2, growth related protein, growth related protein-2, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor-2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-3, transforming growth factor-1.2, transforming growth factor-4, transforming growth factor-5, latent transforming growth factor-1, transforming growth factor binding protein I, transforming growth factor binding protein II, transforming growth factor binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Combination therapy can also be achieved with a specific binding agent of the present invention, such as an antibody, in combination with an apoptotic inducer such as a specific binding agent (e.g., an agonistic antibody or TRAIL ligand) that induces apoptosis via the DR4 (TRAIL R-1) and/or the DR5 (TRAIL R-2) receptor. Examples of such specific binding agents are provided in WO 2007/027713, incorporated herein by reference, which discloses agonistic antibodies that induce apoptosis via the DR5 receptor.

Immunotherapeutics

Immunotherapeutics generally rely on the use of immune effector cells and molecules to target and destroy cancer cells. The immune effectors may be, for example an antibody of the present invention that recognizes some marker on the surface of a target cell. The antibody alone may serve as an effector of therapy or it may recruit other cells to actually effect cell killing. The antibody may also be conjugated to a drug or toxin (chemotherapeutic, radionuclide, ricin A chain, cholera toxin, pertussis toxin, etc.) and thus may merely serve as a targeting agent.

According to the present invention, mutant forms of Ang-1 and/or Ang-2 may be targeted by immunotherapy either antibodies or antibody conjugates of the invention. It is particularly contemplated that the antibody compositions of the invention may be used in a combined therapy approach in conjunction with Ang-2 targeted therapy.

Passive immunotherapy has proved to be particularly effective against a number of cancers. See, for example, WO 98/39027.

The following examples are intended for illustration purposes only, and should not be construed as limiting the scope of the invention in any way.

Example 1

Generation of Affinity Matured Antibodies Against Ang2 by Phage Display

Overall Strategy

CDR randomization was employed to enhance the activity of Ang2 antibody, similar to previous approaches (Chen Y et al., 1999 J Mol Biol (293)865-881; Yelton D E et al., 1995 J Immunol (155) 1994-2004; Yang W—P et al., 1995 J Mol Biol (254) 392-403). Briefly, the variable regions of Ang2 antibody 536 were cloned into the TargetQuest modified pCES-1 vector (Dyax Corp, de Haard H J et al 1999 J Biol Chem (274) 18218-30). All CDR regions were targeted for randomization of each CDR residue by mutagenesis using NNK containing oligonucleotides. After the mutagenesis reaction, phage clones were interrogated for each position using phage ELISA to identify beneficial mutations (for methods see WO 2004/046306, WO 2003/03057134, and US 2003/0099647 A1, for general phage antibody refs., Marks J D et al., 1991 J Mol Biol (222) 581-597; Hoogenboom H R et al 1992 J Mol Biol (227) 381-388; Griffiths A D et al., 1993 EMBO J. (12) 725-734; Vaughan T P et al., 1996 Nat Biotechnol (14) 309-314). Clones with beneficial mutations were converted to full antibodies. Heavy chain clones were paired with light chain clones and resulting IgG was tested for neutralization activity. Top 22 clones were characterized further.

A. Ab536 Fab Template Construction

The variable regions of 536 antibody were cloned into pCES-1 vector using standard molecular biology techniques (Molecular Cloning: A Laboratory Manual, 3$^{rd}$ Edition Cold Spring Harbor Laboratory Press, Cold Spring Harbor, N.Y., 2001). The heavy chain variable and full length light chain fragments were generated by PCR using the following oligonucleotides:

```
Heavy chain reverse:
CCGCTGTGCCCCAGAGGTGC

Heavy chain forward:
tttttccatggccgaggtccagctggtgcagtc

Light chain reverse:
TTTTTTGGCGCGCCTTATTAACACTCTCCCCTGTTGAAGCT

Light chain forward:
tttttgtgcacttgacattgtgatgactcagtct
```

The variable region of heavy chain was inserted between the restriction sites, NcoI and BstEII. The full length light chain was inserted between restriction sites, ApaLI and AscI. The resulting construct was used as a template for CDR randomization.

B. CDR Mutations

Antibody 536 as a Fab in vector pCES-1 was affinity matured by a step-wise site-directed mutagenesis using oligonucleotides bearing NNK (N=ATCG; K=GT) codons for each of the CDR positions. The QuikChange Site-Directed Mutagenesis Kit (Stratagene #200518-5) was used following the manufacturer recommended protocol. To identify phages with enhanced binding to Ang2, phage ELISA performed with biotinylated human Ang2 protein coated at 2 ug/ml in PBS onto the 96 well Maxisorp plates (NUNC). Briefly, after blocking with 2% milk in PBS, overnight phage culture that were grown with helper phage was incubated and bound phages were detected with anti-M13 antibodies conjugated with HRP (Pharmacia). Luminescence signal was compared relative to parental 536 Fab, and clones with superior signal were selected for further analysis.

C. IgG Conversion of Phage Fab

After phage ELISA and sequence analysis, 95 clones each from light chain and heavy chain mutagenesis with enhanced binding against Ang2 were selected and converted into IgG. Briefly, the variable regions of each clone were PCR amplified using a pair of primers. Primer sequences for LC were CTG CTG CTG TGG CTG AGA GGT GCG CGC TGT GAT ATT GTG ATG ACT CAG TCT CCA CTC TCC and AAA AAA CGT ACG TTT GAT CTC CAG CTT GGT CC. Primers for HC were TTTTTTTTGCGCGCTGTGAGGTC-CAGCTGGTGCAGTC and AAAAAAGGCACTA GAGACGGTGACCAGGGTTCC. After digesting with BssHII and BsiWI for LC, and BssHII and BsmBI for HC, the variable regions were inserted into pcDNA3 vectors containing VK1 leader sequence and constant sequence of human Kappa and human IgG1 using standard molecular biology techniques. Each ligation mixture was transformed into two 96 well plates of XL10 gold competent cells (Stratagene), and the transformation mixture were grown overnight for plasmid prep the next day. Resulting DNA were paired with relative parental 536 LC or HC DNA, and transiently transfected into 293T cells in OPTI-MEM using Fugene6. After 7 days, the media from transfected cells were collected, and IgG concentration was quantified by Lance assay using anti-human IgG antibody (Fc specific) labeled with europium and anti-human IgG antibody labeled with APC (Perkin Elmer).

D. Selection of IgG Clones

Conditioned media that contain IgG were tested in HTRF neutralizing assay for its inhibitory effect of Tie-2 interaction with either Ang1 or Ang2. From initial screening, 15LC clones and 11HC clones that showed improved activity were picked. The DNA of selected clones were prepared and confirmed by sequencing. Then the combination of each LC and HC mutants, along with 536 parental clone, were transfected into two 96 plates seeded with 293T cells. Conditioned media were collected, and analyzed for the IgG concentration and inhibitory effect in Tie2 neutralizing assay. From this combination, 22 clones that contain single mutation in each LC and HC were selected for further analysis.

E. Expression and Purification of Human Affinity Matured Ang2 Antibodies in CHO Cells CS-9 cells used for transfection of the anti-Ang2 IgG expression plasmid(s) are a serum-free suspension CHO cell line. They were derived by gradually adapting DXB-11 CHO cells to grow in serum-free medium as described in Rasmussen et al, 1998 (Rasmussen, B., Davis, R., Thomas, J., Reddy, P. 1998. Isolation, characterization and recombinant protein expression in Veggie-CHO: A serum-free CHO host cell line. Cytotechnology. 28: 31-42). DXB-11 cells are a DHFR-deficient mutant derivative from CHO-K1 cells. (Chasin and Urlaub, 1983; Urlaub and Chasin. 1980. Isolation of Chinese hamster cell mutants deficient in dihydrofolate reductase activity. Proc. Natl. Acad. Sci. USA 77, 4216-4220.; Chasin L.A., Graf, L., Ellis, N., Lanzberg, M., Urlaub, G. 1982. Gene amplification in dihydro folate reductase deficient mutants. Schimke, R. T. (Ed.) Gene amplification; Cold Spring Harbor, N.Y. Cold Spring Harbor Laboratory: Cold Spring Harbor, N.Y., p 161-166.). CHO-K1 is an epithelioid cell line originally isolated from the Chinese hamster ovary (Kao and Puck. Genetics of somatic mammalian cells. VII. Induction and isolation of nutritional mutants in Chinese hamster cells. *Proc. Nat. Acad. Sci.* 60: 1275-1281, 1968.).

To derive the CS-9 host cell line, DXB-11 cells were grown in media with gradual reduction in serum over 100 passages to obtain serum-free-adapted cells referred to as SF-CHO (Rasmussen et al, 1998). The SF-CHO cells were subsequently sub-cloned by limiting dilution cloning and individual clones were evaluated. The CS-9 clone was selected as the host cell line for expression of recombinant proteins and banked in serum-free medium. The bank was tested for adventious agents and sterility and found to be free of viral, mycoplasma and microbial agents. The host cell line, CS-9, is a DHFR deficient CHO cell line auxotrophic for glycine, hypoxanthine and thymidine (GHT). The plasmids pDC323 and pDC324 each encode a portion of the DHFR cDNA and the 2 plasmids must complement each other to express a functional DHFR molecule by association of the 2 DHFR fragments in vivo.

The following twenty-two antibodies, each consisted of two heavy chains and 2 light (kappa or lambda) chains as designated in the following Table 2.

TABLE 2

| Antibody* | Antibody Heavy Chain | Antibody Light Chain |
|---|---|---|
| H6L7 | H6 HC | L7 LC |
| H5L7 | H5 HC | L7 LC |
| H4L13 | H4 HC | L13 LC |
| H11L7 | H11 HC | L7 LC |
| H10L7 | H10 HC | L7 LC |
| H4L7 | H4 HC | L7 LC |
| H5L6 | H5 HC | L6 LC |
| H2L7 | H2 HC | L7 LC |
| H5L8 | H5 HC | L8 LC |
| H6L8 | H6 HC | L8 LC |
| H3L7 | H3 HC | L7 LC |
| H5L4 | H5 HC | L4 LC |
| H4L12 | H4 HC | L12 LC |
| H6L6 | H6 HC | L6 LC |
| H4L2 | H4 HC | L2 LC |
| H4L6 | H4 HC | L6 LC |
| H4L4 | H4 HC | L4 LC |
| H5L11 | H5 HC | L11 LC |
| H5L1 | H5 HC | L1 LC |
| H4L11 | H4 HC | L11 LC |
| H5L12 | H5 HC | L12 LC |
| H5L9 | H5 HC | L9 LC |

*Tested for binding to hAng-2, mAng-2, and hAng-1 as described herein.

Tables 3 and 4 set forth the sequences and SEQ ID NOs. of the heavy and light (kappa and lambda) chains of the 22 anti-Ang-1 and/or anti-Ang-2 antibodies converted from phage to full length IgG1 antibodies. The complementarity-determining regions (CDRs) of the monoclonal antibodies were predicted using the VBASE database which uses the technique described by Kabat et al in: *Sequences of Proteins of Immunological Interest* (NIH Publication No. 91-3242; U.S. Dept. Health and Human Services, 5$^{th}$ ed.). Fab regions were aligned to sequences in the database with the closest germline sequence and then visually compared with such sequences. The CDRs for each variable region (heavy or light chain), both residue and sequences are set forth in Table 5.

TABLE 3

Heavy Chain Variable Regions

| Antibody HC | Sequence |
|---|---|
| 536 HC (Ref) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDILTGYGYWGQGTLVTVSS |
| H2 (SEQ ID NO. 1) | EVQLVQSGGGVVQPGRSLRLSCAASGFTFSSYG MHYWVRQAPGKGLEWVSYISSSGSTIEYADSVK GRFTISRDNAKNSLYLQMNSLRAEDTAVYYCAR DLLDYDILTGYGYWGQGTLVTVSS |
| H3 (SEQ ID NO. 2) | EVQLVQSGGGVVQPGRSLRLSCAASGFTFSSYG MHWVRQAPGKGLEWVSYISSSGSTIQTADSVKG RFTISRDNAKNSLYLQMNSLRAEDTAVYYCARD LLDYDILTGYGYWGQGTLVTVSS |
| H4 (SEQ ID NO. 3) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDLLTGYGYWGQGTLVTVSS |
| H6 (SEQ ID NO. 4) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDIYTGYGYWGQGTLVTVSS |
| H10 (SEQ ID NO. 5) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDILTGYGLWGQGTLVTVSS |
| H11 (SEQ ID NO. 6) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDILTGYGMWGQGTLVTVSS |
| H5P (SEQ ID NO. 7) | EVQLVQSGGGVVQPGRSLRLSCAASGFTFSSYG MHWVRQAPGKGLEWVSYISSSGSTIYYADSVKG RFTISRDNAKNSLYLQMNSLRAEDTAVYYCARD LLDYDIWTGYGYWGQGTLVTVSS |

TABLE 4

Light Chain Variable Regions

| Antibody LC | Sequence |
|---|---|
| 536 kappa (Ref) | DIVMTQSPLSLPVTPGEPASISCRSSQSLLHSN GYNYLDWYLQKPGQSPQLLIYLGSNRASGVPDR FSGSGSGTDFTLKISRVEAAEDVGVYYCMQGTH WPPTFGQGTKLEIK |
| L1 (SEQ ID NO. 8) | DIVMTQSPLSLPVTPGEPASISVRSIQSLLQSN GYNYLDWYLQKPGQSPQLLIYLGSNRASGVPDR FSGSGSGTDFTLKISRVEAEDVGVYYCMQGTHW PPTFGQGTKLEIK |
| L2 (SEQ ID NO. 9) | DIVMTQSPLSLPVTPGEPASISCRSSQSLLLSN GYNYLDWYLQKPGQSPQLLIYLGSNRASGVPDR FSGSGSGTDFTLKISRVEAEDVGVYYCMQGTHW PPTFGQGTKLEIK |
| L4 (SEQ ID NO. 10) | DIVMTQSPLSLPVTPGEPASISCRSSQSLLHSH GYNYLDWYLQKPGQSPQLLIYLGSNRASGVPDR FSGSGSGTDFTLKISRVEAEDVGVYYCMQGTHW PPTFGQGTKLEIK |

TABLE 4-continued

Light Chain Variable Regions

| Antibody LC | Sequence |
|---|---|
| L6 (SEQ ID NO. 11) | DIVMTQSPLSLPVTPGEPASISCRSSQSLLHSV GYNYLDWYLQKPGQSPQLLIYLGSNRASGVPDR FSGSGSGTDFTLKISRVEAEDVGVYYCMQGTHW PPTFGQGTKLEIK |
| L7 (SEQ ID NO. 12) | DIVMTQSPLSLPVTPGEPASISCRSSQSLLHSN GYNFLDWYLQKPGQSPQLLIYLGSNRASGVPDR FSGSGSGTDFTLKISRVEAEDVGVYYCMQGTHW PPTFGQGTKLEIK |
| L8 (SEQ ID NO. 13) | DIVMTQSPLSLPVTPGEPASISCRSSQSLLHSN GYNMLDWYLQKPGQSPQLLIYLGSNRASGVPDR FSGSGSGTDFTLKISRVEAEDVGVYYCMQGTHW PPTFGQGTKLEIK |
| L9 (SEQ ID NO. 14) | DIVMTQSPLSLPVTPGEPASISCRSSQSLLHSN GYNYLDWYLQKPGQSPQLLIYAGSNRASGVPDR FSGSGSGTDFTLKISRVEAEDVGVYYCMQGTHW PPTFGQGTKLEIK |
| L11 (SEQ ID NO. 15) | DIVMTQSPLSLPVTPGEPASISCRSSQSLLHSN GYNYLDWYLQKPGQSPQLLIYLGSDRASGVPDR FSGSGSGTDFTLKISRVEAEDVGVYYCMQGTHW PPTFGQGTKLEIK |
| L12 (SEQ ID NO. 16) | DIVMTQSPLSLPVTPGEPASISCRSSQSLLHSN GYNYLDWYLQKPGQSPQLLIYLGSNRASGVPDR FSGSGSGTDFTLKISRVEAEDVGVYYCMQATHW PPTFGQGTKLEIK |
| L13 (SEQ ID NO. 17) | DIVMTQSPLSLPVTPGEPASISVRSSQSLLHSN GYNYLDWYLQKPGQSPQLLIYLGSNRASGVPDR FSGSGSGTDFTLKISRVEAEDVGVYYCMQVTHW PPTFGQGTKLEIK |

TABLE 5

Complementarity-Determining Regions (CDRs) of Heavy Chains (HC) and Light Chains (LC) of Ang-1 and/or Ang-2 Antibodies; Residues and Sequence

| Antibody | CDR 1 Residues | CDR 1 Sequence | CDR 2 Residues | CDR 2 Sequence | CDR 3 Residues | CDR 3 Sequence |
|---|---|---|---|---|---|---|
| Ab 536 HC | 31-35 | SYGMH | 50-66 | YISSSGSTIYYADSVKG | 99-111 | DLLDYDILTGYGY |
| Ab 536 LC | 24-39 | RSSQSLLHSNGYNYLD | 55-61 | LGSNRAS | 94-102 | MQGTHWPPT |
| H6L7 HC | 31-35 | SYGMH (SEQ ID NO. 18) | 50-66 | YISSSGSTIYYADSVKG | 99-111 | DLLDYDIYGYGY (SEQ ID NO. 32) |
| H6L7 LC | 24-39 | RSSQSLLHSNGYNFLD (SEQ ID NO. 19) | 55-61 | LGSNRAS (SEQ ID NO. 27) | 94-102 | MQGTHWPPT (SEQ ID NO. 33) |
| H5L7 HC | 31-35 | SYGMH (SEQ ID NO. 18) | 50-66 | YISSSGSTIYYADSVKG (SEQ ID NO. 26) | 99-111 | DLLDYDIWGYGY (SEQ ID NO. 34) |
| H5L7 LC | 24-39 | RSSQSLLHSNGYNFLD (SEQ ID NO. 19) | 55-61 | LGSNRAS (SEQ ID NO. 27) | 94-102 | MQGTHWPPT (SEQ ID NO. 33) |
| H4L13 HC | 31-35 | SYGMH (SEQ ID NO. 18) | 50-66 | YISSSGSTIYYADSVKG (SEQ ID NO. 26) | 99-111 | DLLDYDLLTGYGY (SEQ ID NO. 35) |
| H4L13 LC | 24-39 | RSSQSLLHSNGYNYLD (SEQ ID NO. 20) | 55-61 | LGSNRAS (SEQ ID NO. 27) | 94-102 | MQVHWPPT (SEQ ID NO. 36) |
| H11L7 HC | 31-35 | SYGMH (SEQ ID NO. 18) | 50-66 | YISSSGSTIYYADSVKG (SEQ ID NO. 26) | 99-111 | DLLDYDILTGMGY (SEQ ID NO. 37) |
| H11L7 LC | 24-39 | RSSQSLLHSNGYNFLD (SEQ ID NO. 19) | 55-61 | LGSNRAS (SEQ ID NO. 27) | 94-102 | MQGTHWPPT (SEQ ID NO. 33) |
| H10L7 HC | 31-35 | SYGMH (SEQ ID NO. 18) | 50-66 | YISSSGSTIYYADSVKG (SEQ ID NO. 26) | 99-111 | DLLDYDILTGLGY (SEQ ID NO. 38) |
| H10L7 LC | 24-39 | RSSQSLLHSNGYNFLD (SEQ ID NO. 19) | 55-61 | LGSNRAS (SEQ ID NO. 27) | 94-102 | MQGTHWPPT (SEQ ID NO. 33) |
| H4L7 HC | 31-35 | SYGMH (SEQ ID NO. 18) | 50-66 | YISSSGSTIYYADSVKG (SEQ ID NO. 26) | 99-111 | DLLDYDLLTGYGY (SEQ ID NO. 35) |
| H4L7 LC | 24-39 | RSSQSLLHSNGYNFLD (SEQ ID NO. 19) | 55-61 | LGSNRAS (SEQ ID NO. 27) | 94-102 | MQGTHWPPT (SEQ ID NO. 33) |
| H5L6 HC | 31-35 | SYGMH (SEQ ID NO. 18) | 50-66 | YISSSGSTIYYADSVKG (SEQ ID NO. 26) | 99-111 | DLLDYDIWTGYGY (SEQ ID NO. 34) |

TABLE 5-continued

Complementarity-Determining Regions (CDRs) of Heavy
Chains (HC) and Light Chains (LC) of Ang-1 and/or Ang-2
Antibodies; Residues and Sequence

| Antibody | CDR 1 Residues | CDR 1 Sequence | CDR 2 Residues | CDR 2 Sequence | CDR 3 Residues | CDR 3 Sequence |
|---|---|---|---|---|---|---|
| H5L6 LC | 24-39 | RSSQSLLHS*V*GYNYLD (SEQ ID NO. 21) | 55-61 | LGSNRAS (SEQ ID NO. 27) | 94-102 | MQGTHWPPT (SEQ ID NO. 33) |
| H2L7 HC | 31-35 | SYGMH (SEQ ID NO. 18) | 50-66 | YISSSGSTI*E*YADSVKG (SEQ ID NO. 28) | 99-111 | DLLDYDILTGYGY (SEQ ID NO. 39) |
| H2L7 LC | 24-39 | RSSQSLLHSNGYN*F*LD (SEQ ID NO. 19) | 55-61 | LGSNRAS (SEQ ID NO. 27) | 94-102 | MQGTHWPPT (SEQ ID NO. 33) |
| H5L8 HC | 31-35 | SYGMH (SEQ ID NO. 18) | 50-66 | YISSSGSTIYYADSVKG (SEQ ID NO. 26) | 99-111 | DLLDYDI*W*TGYGY (SEQ ID NO. 34) |
| H5L8 LC | 24-39 | RSSQSLLHSNGYN*M*LD (SEQ ID NO. 22) | 55-61 | LGSNRAS (SEQ ID NO. 27) | 94-102 | MQGTHWPPT (SEQ ID NO. 33) |
| H6L8 HC | 31-35 | SYGMH (SEQ ID NO. 18) | 50-66 | YISSSGSTIYYADSVKG (SEQ ID NO. 26) | 99-111 | DLLDYDI*Y*TGYGY (SEQ ID NO. 32) |
| H6L8 LC | 24-39 | RSSQSLLHSNGYN*M*LD (SEQ ID NO. 22) | 55-61 | LGSNRAS (SEQ ID NO. 27) | 94-102 | MQGTHWPPT (SEQ ID NO. 33) |
| H3L7 HC | 31-35 | SYGMH (SEQ ID NO. 18) | 50-66 | YISSSGSTI*Q*YADSVKG (SEQ ID NO. 29) | 99-111 | DLLDYDILTGYGY (SEQ ID NO. 39) |
| H3L7 LC | 24-39 | RSSQSLLHSNGYN*F*LD (SEQ ID NO. 19) | 55-61 | LGSNRAS (SEQ ID NO. 27) | 94-102 | MQGTHWPPT (SEQ ID NO. 33) |
| H5L4 HC | 31-35 | SYGMH (SEQ ID NO. 18) | 50-66 | YISSSGSTIYYADSVKG (SEQ ID NO. 26) | 99-111 | DLLDYDI*W*TGYGY (SEQ ID NO. 34) |
| H5L4 LC | 24-39 | RSSQSLLHS*H*GYNYLD (SEQ ID NO. 23) | 55-61 | LGSNRAS (SEQ ID NO. 27) | 94-102 | MQGTHWPPT (SEQ ID NO. 33) |
| H4L12 HC | 31-35 | SYGMH (SEQ ID NO. 18) | 50-66 | YISSSGSTIYYADSVKG (SEQ ID NO. 26) | 99-111 | DLLDYD*L*LTGYGY (SEQ ID NO. 35) |
| H4L12 LC | 24-39 | RSSQSLLHSNGYNYLD (SEQ ID NO. 20) | 55-61 | LGSNRAS (SEQ ID NO. 27) | 94-102 | MQ*A*THWPPT (SEQ ID NO. 40) |
| H6L6 HC | 31-35 | SYGMH (SEQ ID NO. 18) | 50-66 | YISSSGSTIYYADSVKG (SEQ ID NO. 26) | 99-111 | DLLDYDI*Y*TGYGY (SEQ ID NO. 32) |
| H6L6 LC | 24-39 | RSSQSLLHS*V*GYNYLD (SEQ ID NO. 21) | 55-61 | LGSNRAS (SEQ ID NO. 27) | 94-102 | MQGTHWPPT (SEQ ID NO. 33) |
| H4L2 HC | 31-35 | SYGMH (SEQ ID NO. 18) | 50-66 | YISSSGSTIYYADSVKG (SEQ ID NO. 26) | 99-111 | DLLDYD*L*LTGYGY (SEQ ID NO. 35) |
| H4L2 LC | 24-39 | RSSQSLL*L*SNGYNYLD (SEQ ID NO. 24) | 55-61 | LGSNRAS (SEQ ID NO. 27) | 94-102 | MQGTHWPPT (SEQ ID NO. 33) |
| H4L6 HC | 31-35 | SYGMH (SEQ ID NO. 18) | 50-66 | YISSSGSTIYYADSVKG (SEQ ID NO. 26) | 99-111 | DLLDYD*L*LTGYGY (SEQ ID NO. 35) |
| H4L6 LC | 24-39 | RSSQSLLHS*V*GYNYLD (SEQ ID NO. 21) | 55-61 | LGSNRAS (SEQ ID NO. 27) | 94-102 | MQGTHWPPT (SEQ ID NO. 33) |
| H4L4 HC | 31-35 | SYGMH (SEQ ID NO. 18) | 50-66 | YISSSGSTIYYADSVKG (SEQ ID NO. 26) | 99-111 | DLLDYD*L*LTGYGY (SEQ ID NO. 35) |
| H4L4 LC | 24-39 | RSSQSLLHS*H*GYNYLD (SEQ ID NO. 23) | 55-61 | LGSNRAS (SEQ ID NO. 27) | 94-102 | MQGTHWPPT (SEQ ID NO. 33) |
| H5L11 HC | 31-35 | SYGMH (SEQ ID NO. 18) | 50-66 | YISSSGSTIYYADSVKG (SEQ ID NO. 26) | 99-111 | DLLDYDI*W*TGYGY (SEQ ID NO. 34) |
| H5L11 LC | 24-39 | RSSQSLLHSNGYNYLD (SEQ ID NO. 20) | 55-61 | LGS*D*RAS (SEQ ID NO. 30) | 94-102 | MQGTHWPPT (SEQ ID NO. 33) |
| H5L1 HC | 31-35 | SYGMH (SEQ ID NO. 18) | 50-66 | YISSSGSTIYYADSVKG (SEQ ID NO. 26) | 99-111 | DLLDYDI*W*TGYGY (SEQ ID NO. 34) |

TABLE 5-continued

Complementarity-Determining Regions (CDRs) of Heavy
Chains (HC) and Light Chains (LC) of Ang-1 and/or Ang-2
Antibodies; Residues and Sequence

| Antibody | CDR 1 Residues | CDR 1 Sequence | CDR 2 Residues | CDR 2 Sequence | CDR 3 Residues | CDR 3 Sequence |
|---|---|---|---|---|---|---|
| H5L1 LC | 24-39 | RS *I*QSLL *Q*SNGYNLD (SEQ ID NO. 25) | 55-61 | LGSNRAS (SEQ ID NO. 27) | 94-102 | MQGTHWPPT (SEQ ID NO. 33) |
| H4L11 HC | 31-35 | SYGMH (SEQ ID NO. 18) | 50-66 | YISSSGSTIYYADSVKG (SEQ ID NO. 26) | 99-111 | DLLDYD *L*LTGYGY (SEQ ID NO. 35) |
| H4L11 LC | 24-39 | RSSQSLLHSNGYNYLD (SEQ ID NO. 20) | 55-61 | LGS *D*RAS (SEQ ID NO. 30) | 94-102 | MQGTHWPPT (SEQ ID NO. 33) |
| H5L12 HC | 31-35 | SYGMH (SEQ ID NO. 18) | 50-66 | YISSSGSTIYYADSVKG (SEQ ID NO. 26) | 99-111 | DLLDYDI *W*TGYGY (SEQ ID NO. 34) |
| H5L12 LC | 24-39 | RSSQSLLHSNGYNYLD (SEQ ID NO. 20) | 55-61 | LGSNRAS (SEQ ID NO. 27) | 94-102 | MQ *A*THWPPT (SEQ ID NO. 40) |
| H5L9 HC | 31-35 | SYGMH (SEQ ID NO. 18) | 50-66 | YISSSGSTIYYADSVKG (SEQ ID NO. 26) | 99-111 | DLLDYDI *W*TGYGY (SEQ ID NO. 34) |
| H5L9 LC | 24-39 | RSSQSLLHSNGYNYLD (SEQ ID NO. 20) | 55-61 | *A*GSNRAS (SEQ ID NO. 31) | 94-102 | MQGTHWPPT (SEQ ID NO. 33) |

Example 2

Molecular Assays to Evaluate Ang-2 Antibodies

Molecular assays (Affinity ELISA, Neutralization ELISA and BIAcore) were developed to assess direct antibody binding to Ang-2 and related family members (for example, Ang-1), and the effect of antibodies on the Ang-2:Tie2 interaction. These in vitro and cell-based assays are described as follows.

A. Affinity ELISA

For the initial screening of candidate anti-Ang-2 antibodies, purified human Ang-2 (R and D Systems, Inc; catalog number 623-AN; Ang-2 is provided as a mixture of 2 truncated versions) or murine Ang-2 polypeptide (prepared as described above) were used. For confirmatory binding assays, human Ang-2 was obtained from conditioned media of human 293T cells transfected with full length human Ang-2 DNA and cultured in serum free DMEM containing about 50 micrograms per ml of bovine serum albumin (BSA).

Using microtiter plates, approximately 100 microliters per well of Ang-2 was added to each well and the plates were incubated about 2 hours, after which the plates were washed with phosphate buffered saline (PBS) containing about 0.1 percent Tween-20 four times. The wells were then blocked using about 250 microliters per well of about 5 percent BSA in PBS, and the plates were incubated at room temperature for about 2 hours. After incubation, excess blocking solution was discarded, and about 100 microliters of candidate anti-Ang-2 antibody was added to each well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog #31416) previously diluted 1:5000 in PBS containing 1 percent BSA (bovine serum albumin) was added. Plates were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma chemical Company, St. Louis, Mo., catalog number T8665) substrate was added and plates were incubated about 5-15 minutes until blue color developed. Absorbance was then read in a spectrophotomer at about 370 nm.

B. Neutralization ELISA

Microtiter plates to which human Ang-2 polypeptide was bound were prepared as described for the Affinity ELISA. Candidate anti-Ang-2 antibodies were prepared in serial dilutions as described for the Affinity ELISA above in a solution of PBS containing about 1 percent BSA and about 1 nM Tie2 (provided as a Tie2-Fc molecule where the Tie2 portion contains only the soluble extracellular portion of the molecule; R and D Systems, catalog number 313-TI). After about 100 microliters of the antibody/Tie2 solution was added to each well, the plates were incubated overnight at room temperature, and then washed five times in PBS containing about 0.1 percent Tween-20. After washing, about 100 microliters per well of anti-Tie2 antibody (Pharmingen Inc., catalog #557039) was added to a final concentration of about 1 microgram per ml and the plates were incubated about 1 hour at room temperature then washed five time in PBS containing about 0.1 percent Tween-20. Next, about 100 microliters per well of goat anti-mouse-IgG-HRP (Pierce Chemical CO., catalog #31432) was added at a dilution of 1:10,000 in PBS containing about 1 percent BSA. Plates were incubated at room temperature for about 1 hour, after which they were washed five times with PBS containing about 0.1 percent Tween-20. About 100 microliters per well of TMB substrate (described above) was then added and color was allowed to develop. Absorbance was then read in a spectrophotomer at 370 nm.

C. Affinity BiaCore™

An affinity analysis of each candidate Ang-2 antibody was performed on a BIAcore®2000 (Biacore, Inc., Piscataway, N.J.) with PBS and 0.005 percent P20 surfactant (BIAcore, Inc.) as running buffer. Recombinant Protein G (Repligen, Needham, Mass.) was immobilized to a research grade CM5 sensor chip (Biacore, Inc.) via primary amine groups using the Amine Coupling Kit (Biacore, Inc.) according to the manufacturer's suggested protocol.

Binding assays were carried out by first attaching about 100 Ru of each candidate anti-Ang-2 antibody to the immobilized Protein G, after which various concentrations (0-100 nM) of huAng-2 or mAng-2 were then injected over the bound antibody surface at a flow rate of about 50 ul/min for about 3 minutes. Antibody binding kinetics including $k_a$ (association rate constant), $k_d$ (dissociation rate constant) and $K_D$ (dissociation equilibrium constant) were determined using the BIA evaluation 3.1 computer program (BIAcore, Inc.). Lower dissociation equilibrium constants indicated greater affinity of the antibody for Ang-2.

All twenty two of the antibodies and a negative control IgG1 (referred to as RDB1) were tested using affinity and neutralization ELISA (as described in Example 3 above) as well as the BIAcore neutralization assay to determine their affinity, neutralization, and specificity capabilities. The results are set forth below (Table 2) and were calculated using standard procedures. Three antibodies, H6L7, H4L4 and H4L11 were evaluated for IC50 neutralizing concentrations against human and murine Ang-1 and Ang-2., using the ELISA analysis described above. All three antibodies were shown to crossreact with mouse, rabbit, and cynomolgus monkey Ang1 and Ang2, exhibiting similar potencies across angiopoietin orthologs. The results are reported in the following Table 3.

D. HTRF hAng-1 and hAng-2 Antibody IC50s and IC90s

Equal volume of 1.6 nM Streptavidin-Europium (SA-EU) and 8 nM Biotinylated angiopoietin 2 (in-house) or Biotinylated agiopoietin 1 (R&D Cat #BAF923) were mixed and incubated at room temperature for 30 minutes in the dark with rotation in a 15 ml conical tube (Fisher 352096). Then 50 ul of the above SA-EU/Biotinylated Ang 2(1) mixture was added to each well on a Mixing Plate (Costar 3356). To the Mixing Plate, 50 ul of serial diluted Ang1 and Ang2 antibody at 4× final concentrations were added to each well. The Mixing Plate was then incubated at room temperature for 1 hour on a shaker in the dark. On an Assay Plate (Costar 3356), 20 ul of 10 nM huTie-2-Fc-APC (Prozyme Custom Lot #DF99-048) was added to each well. Then 20 ul of the mixture from each well on the Mixing Plate was transferred to each well on the Assay Plate. The Assay Plate was incubated at room temperature for 2 hours in the dark with rotation. Then the Assay Plate was read on RUBYstar plate reader (BMG labtechnologies, INC). All the reagents in the assay were diluted with HTRF buffer (50 mM Tris HCl, 100 mM NaCl, 0.1% BSA and 0.05% Tween™20). IC50 and IC90 were calculated with GRAFIT 5.0.

TABLE 6

Biochemical Potency of Antibodies Against hAng1 and hAng2

| Antibody | IC50 hAng1 (nM) | IC90 hAng1 (nM) | IC90/IC50 | IC50 hAng2 (nM) | IC90 hAng2 (nM) | IC90/IC50 |
|---|---|---|---|---|---|---|
| H6L7 | 0.06 | 0.49 | 8.0 | 0.06 | 0.19 | 3.3 |
| H5L7 | 0.07 | 0.42 | 6.3 | 0.07 | 0.23 | 3.6 |
| H4L13 | 0.15 | 1.6 | 11 | 0.06 | 0.19 | 3.2 |
| H11L7 | 0.15 | 1.2 | 8.1 | 0.06 | 0.20 | 3.2 |
| H10L7 | 0.15 | 2.2 | 14 | 0.06 | 0.19 | 3.4 |
| H4L7 | 0.23 | 2.8 | 12 | 0.06 | 0.22 | 3.5 |
| H5L6 | 0.32 | 3.6 | 11 | 0.07 | 0.23 | 3.4 |
| H2L7 | 0.33 | 3.6 | 11 | 0.06 | 0.20 | 3.3 |
| H5L8 | 0.37 | 3.6 | 10 | 0.07 | 0.21 | 3.1 |
| H6L8 | 0.57 | 7.7 | 13 | 0.05 | 0.19 | 3.6 |
| H3L7 | 0.58 | 7.1 | 12 | 0.06 | 0.23 | 4.0 |
| H5L4 | 0.60 | 11 | 19 | 0.07 | 0.21 | 2.8 |
| H4L12 | 0.63 | 8.7 | 14 | 0.06 | 0.21 | 3.4 |
| H6L6 | 0.66 | 10 | 16 | 0.06 | 0.20 | 3.4 |
| H4L2 | 0.66 | 6.8 | 10 | 0.06 | 0.19 | 3.1 |
| H4L6 | 0.74 | 15 | 20 | 0.06 | 0.20 | 3.2 |
| H4L4 | 0.87 | 8.2 | 9.4 | 0.06 | 0.16 | 2.7 |
| H5L11 | 0.97 | 18 | 18 | 0.08 | 0.25 | 3.3 |
| H5L1 | 1.7 | 24 | 15 | 0.06 | 0.29 | 4.4 |
| AMG 386* | 2.6 | 106 | 41 | 0.03 | 0.13 | 4.1 |
| AMG 386* | 3.9 | 278 | 71 | 0.03 | 0.15 | 4.4 |
| H4L11 | 7.3 | 107 | 15 | 0.05 | 0.17 | 3.4 |
| H5L12 | 14 | 159 | 11 | 0.07 | 0.31 | 4.4 |
| H5L9 | 18 | 181 | 10 | 0.19 | 1.57 | 8.5 |

*Peptibody.

Example 3

Molecular Characterization of Angiopoietin Antibodies

Four of the fully human IgG2 antibodies (Ab536, H4L4, H6L7, and H4L11) with potent hAng2 inhibitory activity and a range of hAng1 inhibitory activities were selected for further studies. All 4 antibodies were shown to crossreact with mouse, rabbit, and cynomolgus monkey Ang1 and Ang2, exhibiting similar potencies across angiopoietin orthologs (Tables 7 and 8).

TABLE 7

Biochemical Potency of Angiopoietin Antibodies Against Ang2 Orthologs

| Clone | Human Ang2 IC50 (nM) | Cyno Ang2 IC50 (nM) | Murine Ang2 IC50 (nM) | Rabbit Ang2 IC50 (nM) |
|---|---|---|---|---|
| H6L7 | 0.22 | 0.19 | 0.13 | 0.15 |
| H4L4 | 0.22 | 0.24 | 0.15 | 0.15 |
| AMG 386 | 0.12 | 0.17 | 0.10 | 0.10 |
| H4L11 | 0.21 | 0.16 | 0.12 | 0.12 |
| 536 LC1 | 0.27 | 0.19 | 0.14 | 0.20 |

ELISA measuring neutralization of ligand/receptor interaction.

TABLE 8

Biochemical Potency of Angiopoietin Antibodies Against Ang1 Orthologs

| Clone | Human Ang1 IC50 (nM) | Cyno Ang1 IC50 (nM) | Murine Ang1 IC50 (nM) | Rabbit Ang1 IC50 (nM) |
|---|---|---|---|---|
| H6L7 | 0.12 | 0.19 | 0.12 | 0.18 |
| H4L4 | 3.2 | 4.0 | 3.3 | 2.8 |
| AMG 386 | 1.2 | 2.9 | 2.7 | 4.3 |
| H4L11 | 17 | 14 | 7.7 | 16 |
| 536 LC1 | 515 | 531 | 305 | 502 |

ELISA measuring neutralization of ligand/receptor interaction.

Example 4

Activity of Andopoietin Antibodies in Colo205 Tumor Xenografts

Three antibodies (H6L7, H4L4 and H4L11) were evaluated in the Colo205 human colorectal carcinoma xenograft model. For each study group, mice were injected subcutaneously on the right flank with $2\times10^6$ cells in Matrigel™. Ten animals with average tumor volume of 300 mm3 were randomly assigned to each experimental group. The animals were injected IP twice per week, beginning on day 17 post implantation, with 300 µg of the angiopoietin-targeted antibodies or isotype control antibody. AMG 386 at the optimum biological dose (OBD) in this model of 14 µg (SC) twice weekly was included as a positive control and antibody 536LC1 was included at 300 µg twice weekly. Body weight and tumor size were measured twice weekly.

Figure 1:
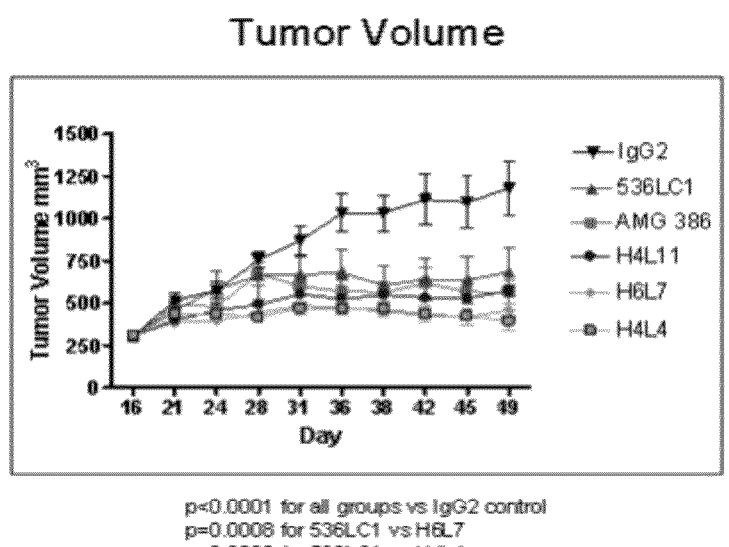
FIG. 1 depicts a graph of tumor size (y-axis) versus time (x-axis) in tumor-bearing mice treated with either an anti-Ang1/2 antibody (H4L4, H4L11, or H6L7) of the invention or a highly potent control peptibody (AMG 386) or antibody 536, compared to treatment with an isotype control antibody. Details are described in the Examples.
Figure 2:
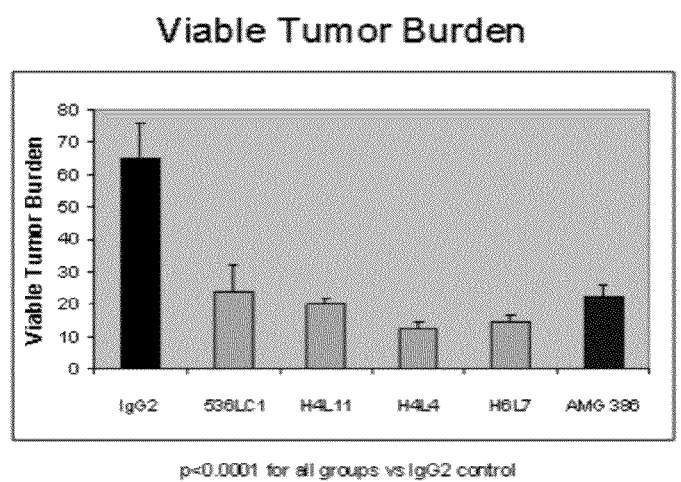
FIG. 2 depicts the tumor burden (% viable tumor [bisected section]×tumor weight) in tumor-bearing mice treated with an anti-Ang1/2 antibody (H4L4, H4L11, or H6L7) of the invention or a highly potent control peptibody (AMG 386) or antibody 536 compared to treatment with an isotype control antibody. Details are described in the Examples.

As shown in FIG. 1, all three antibodies significantly inhibited tumor growth compared to treatment with an isotype control antibody (p<0.0001). Treatment with H6L7 and H4L4, resulted in significantly greater inhibition of tumor growth compared to 536LC1. Data represents mean±SEM. At the end of the experiment, tumors were harvested, fixed in zinc-formalin and paraffin embedded. Histological sections of tumor were stained with hematoxylin. The viable tumor fraction was then estimated, using RGB thresholding and automated pixel counting, from a 1× digital image of the entire tumor cross-section. Viable tumor burden was calculated as the viable fraction multiplied by the terminal tumor weight. Data represents mean±SEM (n=10). FIG. 2 demonstrates that antibodies H6L7, H4L4 and H4L11 also significantly reduced tumor burden relative to control (p<0.0001), suggesting that the volume-based tumor measurements underestimated the anti-tumor effect of the antibodies.

Histopathology was performed on tumors and normal tissues from the mice in the study shown in FIGS. 1 and 2. Treatment of xenograft-bearing nude mice with the angiopoietin inhibitors (AMG 386, 536LC1, H4L4, H4L11, or H6L7) did not elicit adverse anatomic effects in non-target tissues.

Example 5

Figure 3:
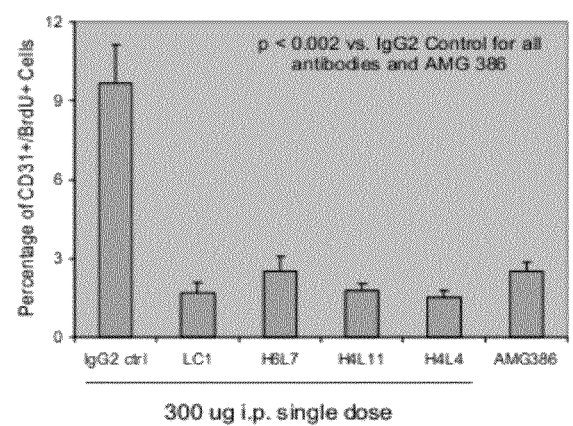
FIG. 3 depicts the effect of H4L4, H4L11, and H6L7 of the invention, a highly potent control peptibody (AMG 386) and antibody 536 on endothelial cell proliferation in Colo205 tumor-bearing mice. Details are described in the Examples.

Effect of Anti-Ang-1 and/or Ang-2 Antibodies on Endothelial Cell Proliferation In a parallel experiment, animals with approximately 400 mm³ tumors were treated with 536LC1 (AKA LC1), H4L11, H4L4, H6L7, AMG 386 or control IgG2 for 72 hrs. Seventeen hours prior to sacrifice, animals were implanted with osmotic minipumps containing 3 mg/mL BrdU. Upon sacrifice, endothelial cells were isolated from the Colo205 tumor-bearing mice and were analyzed by flow cytometry to assess proliferation. Dissociated cells were stained with anti-mouse CD45-FITC and CD31-PE antibodies, followed by fixation and staining with anti-BrdU-alexa647 antibodies. Data represents mean±SEM (n=5). As shown in FIG. 3, treatment with all antibodies significantly reduced the percentage of BrdU positive cells (p<0.002 compared to IgG2 control). These data are consistent with an anti-angiogenic therapeutic mechanism whereby the angiopoietin-targeted antibodies inhibit tumor endothelial cell proliferation in vivo.

Example 6

Dose Titration of H4L4 in Colo205 Tumor Xenografts

Figure 4:
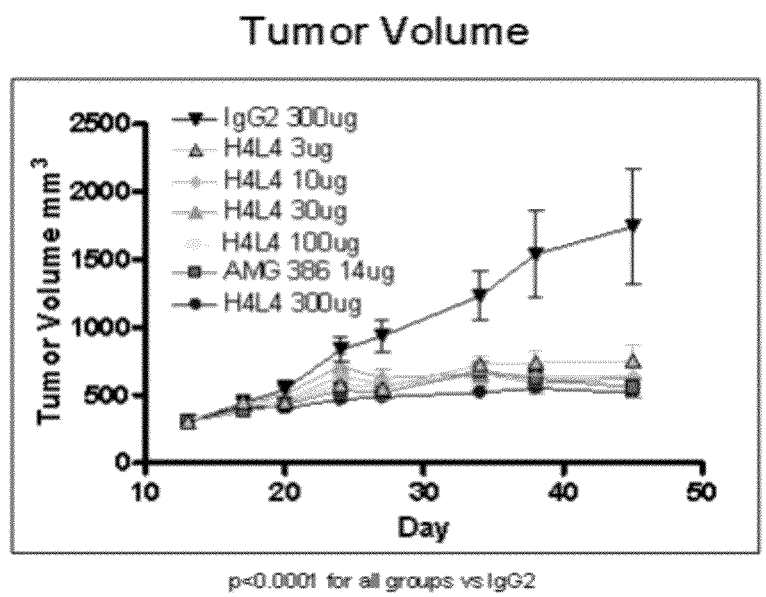
FIG. 4 depicts the H4L4 antibody dose-response relationship in Colo205 tumor-bearing mice. Details are described in the Examples.
Figure 5:
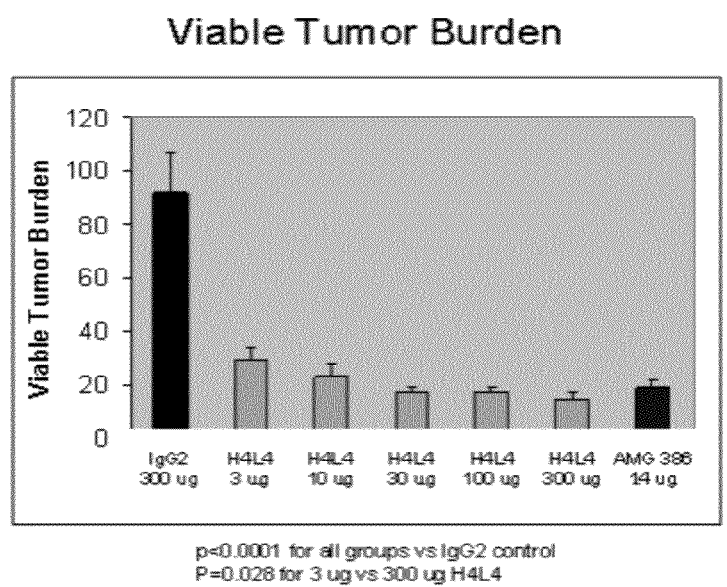
FIG. 5 depicts the effect of H4L4 antibody on Colo205 tumor burden in vivo. Details are described in the Examples.

The antibody H4L4 was selected for more extensive analysis exploring the dose dependency of H4L4-mediated tumor growth inhibition. The animals were injected with H4L4 IP twice-weekly beginning on day 14 at doses ranging from 3 µg to 300 µg. AMG 386 at the optimum biological dose of 14 µg (SC) twice weekly was included as a positive control. As shown in FIG. 4, all doses of H4L4 significantly inhibited tumor growth and viable tumor burden (p<0.0001), with an OBD of ~30 µg in the viable tumor burden analysis (FIG. 5.).

Example 7

Effect of H4L4 on Colo205 Tumor Endothelial Cell Proliferation In Vivo

In a parallel experiment, Colo205 tumor-bearing mice with tumors of approximately 450 mm³ were treated with a single dose of H4L4, AMG 386 or control IgG2 for 72 hours and then analyzed as in FIG. 3. As shown in FIG. 6, treatment with H4L4 significantly inhibited endothelial cell proliferation in a dose-dependent manner, with an OBD of 30 µg.

Example 8

Pharmacokinetics of H4L4, H6L7, H4L11, and 536LC1 in Mice, Rats and Cynomologus Monkey The pharmacokinetics (PK) of H4L4, H6L7, H4L11, and 536LC1 have been characterized in CD-1 mice after single-dose intravenous (IV) or intraperitoneal (IP) administration. The PK of H4L4 and H6L7 was also characterized in Sprague-Dawley rats and cynomolgus monkeys after single-dose IV administration.

After single-dose IV or IP administration to mice, H4L4 exposure appeared to increase approximately dose-proportionally in the dose range of 0.1 to 10 mg/kg (Table 4). The overall mean terminal half-life ($t_{1/2,z}$), clearance (CL), and volume of distribution at steady-state ($V_{ss}$) was 207 hrs, 0.43 mL/hr/kg, and 128 mL/kg, respectively. The bioavailability (% F) after IP administration was greater than 90% for all dose groups. In contrast, H6L7, H4L11, and 536LC1 exhibited nonlinear PK in mice with exposure increasing greater than dose proportionally from 0.1 to 10 mg/kg. The exposure of H6L7 in rats and monkeys also increased greater than dose-proportionally after a single IV dose of 0.1 to 10 mg/kg.

In contrast to its linear PK profile in mice, H4L4 exhibited nonlinear rat and monkey PK. The mean residence time (MRT) in rats ranged from 57 to 217 hours; the CL ranged from 0.3 to 1.4 mL/hr/kg; the $V_{ss}$ ranged from 57 to 68 mL/kg. In monkeys, the MRT ranged from 40 to 163 hours; the CL ranged from 0.4 to 1.9 mL/hr/kg; the $V_{ss}$ ranged from 49 to 75 mL/kg.

The PK of H4L4 was also assessed in nude mice bearing Colo205 tumor xenografts in a pharmacology study at 3, 10, 30, 100 or 300 µg dose/mouse, administered IP twice weekly for 4 weeks. Serum H4L4 exposure increased approximately dose proportionally as assessed by serum trough concentrations. The PK of H4L4 in nude mice was similar to that observed in CD-1 mice, and PK did not appear to change over time.

TABLE 9

PK Parameters of H4L4 and H6L7 in Preclinical Species

| | Mouse | | | Rat | | | Monkey | | |
| | \multicolumn{9}{c}{Dose (mg/kg)} |
| | 0.1 | 1 | 10 | 0.1 | 1 | 10 | 0.1 | 1 | 10 |
|---|---|---|---|---|---|---|---|---|---|
| H4L4 | | | | | | | | | |
| $t_{1/2,z}$ (hr) | 196 | 180 | 244 | 42.5 | 66.7 | 213 | 36.2 | 35.6 | 80.1 |
| MRT (hr) | 259 | 273 | 420 | 57.4 | 107 | 217 | 40.1 | 52.0 | 163 |
| CL (mL/hr/kg) | 0.666 | 0.386 | 0.249 | 1.39 | 0.552 | 0.319 | 1.89 | 0.933 | 0.414 |
| $V_{ss}$ (mL/kg) | 173 | 105 | 105 | 66.4 | 57.0 | 68.5 | 74.9 | 48.6 | 67.4 |
| $V_0$ (mL/kg) | 71.0 | 46.6 | 46.7 | 43.3 | 34.5 | 36.1 | 48.2 | 40.8 | 44.0 |
| H6L7 | | | | | | | | | |
| $t_{1/2,z}$ (hr) | 8.27 | 99.0 | 82.8 | 9.43 | 25.8 | 92.9 | 10.4 | 32.6 | 65.0 |
| MRT (hr) | 11.6 | 54.3 | 263 | 13.2 | 41.2 | 158 | 15.1 | 51.8 | 158 |
| CL (mL/hr/kg) | 19.4 | 2.00 | 0.349 | 3.31 | 1.02 | 0.331 | 2.81 | 0.824 | 0.358 |
| $V_{ss}$ (mL/kg) | 224 | 109 | 91.8 | 43.3 | 41.3 | 51.9 | 41.3 | 42.2 | 55.2 |
| $V_0$ (mL/kg) | 90.9 | 58.4 | 56.6 | 35.4 | 35.3 | 38.1 | 40.0 | 37.7 | 43.1 |

Example 9

Angiopoietin-1 Neutralization Mediates Context-Dependent Suppression of Angiogenesis and Tumor Growth While Angiopoietin-2 (Ang2) is a key mediator of postnatal angiogenesis, the role of Angiopoietin-1 (Ang1) in this setting is less clear. To investigate the postnatal function of Ang1, we have developed potent and selective peptibodies (peptide-Fc fusion proteins) that inhibit the interaction between Ang1 and its receptor, Tie2. We show that selective Ang1 antagonism has no independent effect in models of angiogenesis-associated diseases (cancer and diabetic retinopathy), although it can induce ovarian atrophy in normal juvenile rats and inhibit ovarian follicular angiogenesis in a hormone-induced ovulation model. Surprisingly, the activity of Ang1 inhibitors appears to be unmasked in some disease models when combined with Ang2 inhibitors. Dual inhibition of Ang1 and Ang2 cooperatively suppresses ovarian follicular angiogenesis and tumor xenograft growth; however, Ang1 inhibition fails to augment the activity of Ang2 inhibition in suppressing tumor endothelial cell proliferation, corneal angiogenesis, and oxygen-induced retinal angiogenesis. In no case was Ang1 inhibition shown to 1) confer superior activity to that of Ang2 inhibition or dual Ang1/Ang2 inhibition or 2) antagonize the effects of Ang2 inhibition. These results imply that Ang1 plays a context-dependent role in promoting postnatal angiogenesis and angiogenesis-associated pathology.

Ang1 plays an important role in developmental angiogenesis, but its function in postnatal neovascularization is less clear. Ang1 has been shown to mediate both pro- and anti-angiogenic effects in various postnatal settings. To investigate the function of Ang1 by inhibiting endogenous Ang1. To that end, we have developed Ang1-neutralizing peptibodies and tested them alone or in combination with Ang2 inhibitors in preclinical models of postnatal angiogenesis.

Figure 7:
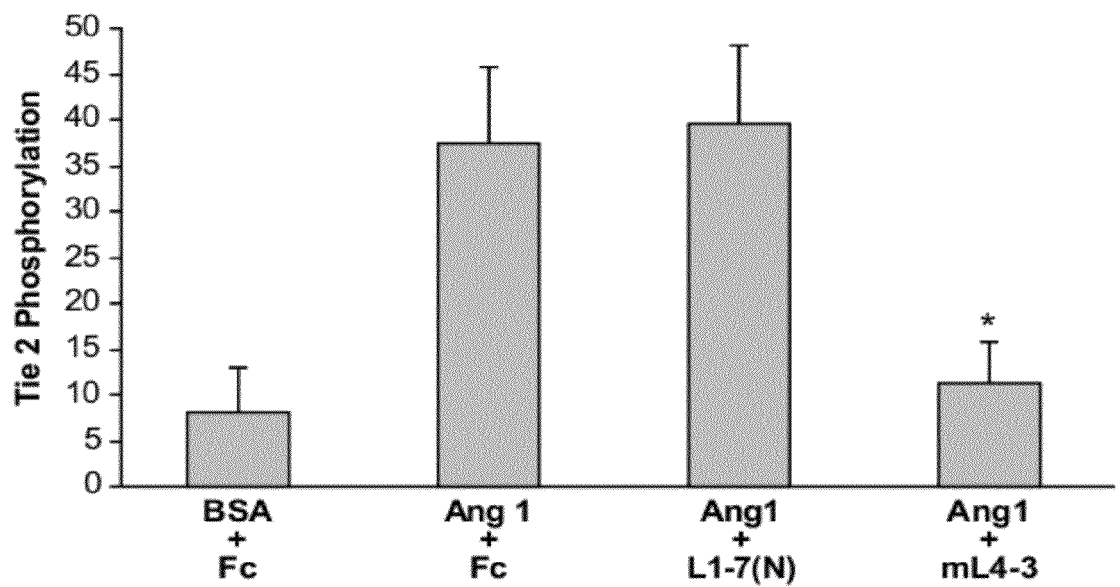
FIG. 7 depicts systemically administered mL4-3 neutralizes Ang1-induced Tie2 phosphorylation in mouse lungs. Mice (n=3 per group) were treated with L1-7(N) (2 mg/kg), mL4-3 (20 mg/kg) or Fc control (20 mg/kg) daily for 23 days prior to i.v. challenge with Ang1 or BSA. Mouse lungs were subsequently harvested, and the levels of phosphorylated Tie2 were determined by immunoprecipitation-Western blot analysis. Data are mean values±SE. *P=0.0005 vs Ang1 plus Fc, ANOVA with Fisher's post hoc test.

We generated Ang1-neutralizing peptibodies to investigate the functional role of Ang1 in angiogenesis. Phage display peptide libraries were panned to identify peptides that bound Ang1, but not Ang2. The resulting clones were converted into peptibodies by expressing the peptides in E. coli as fusions to the Fc portion of human IgG1. Peptibodies were then screened by enzyme-linked immunosorbent assay (ELISA) and homogeneous time-resolved fluorescence (HTRF) assays for their ability to neutralize the interaction between Tie2 and angiopoietins. One of these peptibodies was affinity-matured to increase its ability to antagonize Ang1, and a resultant peptibody, mL4-3, was chosen for the studies herein. mL4-3 exhibited similar potency against several Ang1 orthologs, and it displayed >40,000-fold selectivity over Ang2 (Tables 10 and 11). Also shown in Table 10 are two previously described peptibodies: AMG 386 [also known as 2xCon4 (C)] and L1-7(N). L1-7(N) is a very potent and selective Ang2 inhibitor, and AMG 386 is a dual inhibitor of Ang1 and Ang2. The pharmacokinetic profiles of mL4-3 in rodents were acceptable for daily to weekly s.c. dosing (Table 3).

mL4-3 can be used as a reagent for interrogating Ang1 function in vivo. To assess whether mL4-3 was capable of selectively sequestering Ang1 in vivo, mL4-3, L1-7(N), and Fc were administered s.c. to mice, followed by an i.v. challenge with recombinant Ang1. Ang1 induced Tie2 phosphorylation in mouse lung endothelium (approximately 5-fold), an effect that could be prevented by mL4-3, but not by L1-7 (N) or Fc (FIG. 7).

Figure 8:
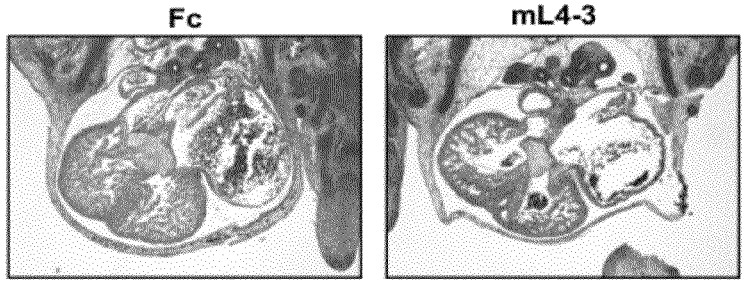
FIG. 8 depicts pharmacologic inhibition of Ang1 during early organogenesis alters heart development. A) Mouse embryos exposed to 300 mg/kg mL4-3 (right panel) had smaller hearts with fewer, narrower, and more widely spaced trabeculae relative to the larger hearts with large, wide trabeculae found in stage-matched embryos exposed to 300 mg/kg Fc control (left panel). Representative images are shown. B) Incidence of cardiac abnormalities in Fc- and mL4-3-treated embryos. *P<0.0001 vs Fc, chi-square test.

Next, we wanted to determine whether mL4-3 could neutralize endogenous Ang1 in a setting in which Ang1 was known to play a physiologically relevant role. Developmental genetic knockout studies have shown that Ang1 deletion reduces cardiac size and endocardial folding in embryos. In an attempt to replicate this phenotype pharmacologically, mL4-3 was administered to pregnant mice in early and middle gestation. Embryos were harvested at embryonic day 12.5, the time at which lethality was observed in Ang1-null mouse embryos. Pharmacokinetic assessment of mouse embryo lysates demonstrated a mean mL4-3 trough level of 3.0 µg/g of tissue, confirming that mL4-3 was capable of crossing the placenta. Histological analysis revealed reduced cardiac size and trabeculation, similar to, but less dramatic than that observed in Ang1-null embryos (FIG. 8). The less pronounced phenotype of the mL4-3 treated embryos may be a consequence of suboptimal embryonic mL4-3 exposures and incomplete Ang1 sequestration. Nonetheless, mL4-3 clearly induces embryonic cardiac defects that phenocopy those of Ang1 genetic knockout mice, confirming the utility of mL4-3 as a reagent for investigating Ang1 function in vivo.

Figure 9:
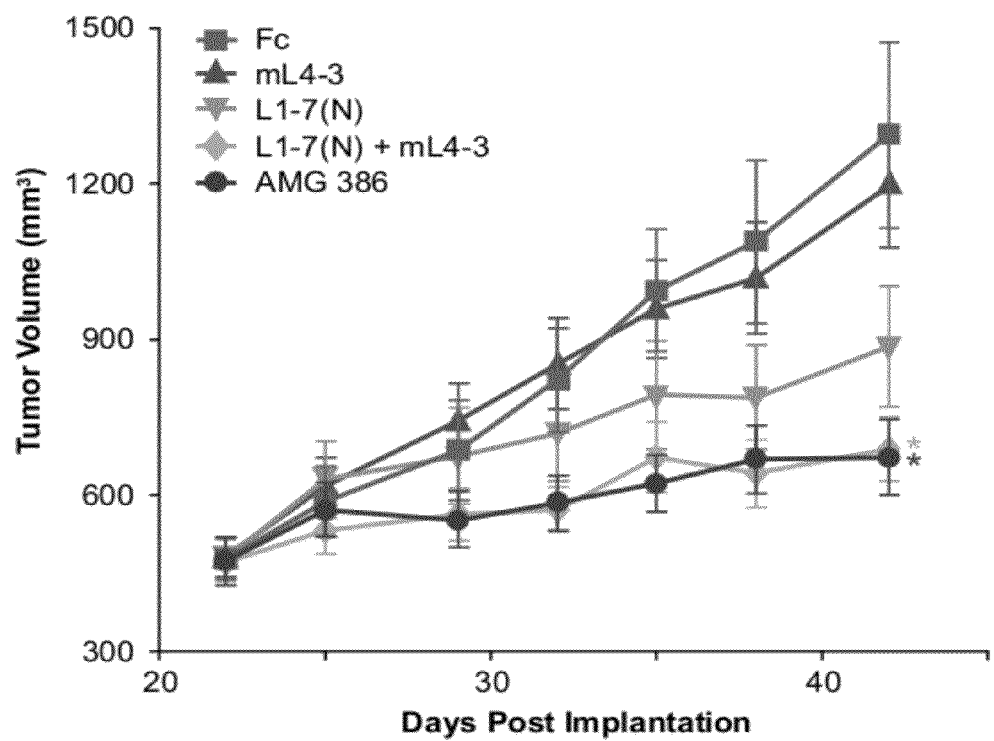
FIG. 9 depicts the effect of combined Ang1 and Ang2 inhibition on the growth of Colo205 tumor xenografts. Mice (n=10 per group) were implanted with Colo205 cells, and treatment began when tumors reached approximately 500 mm$^3$ with Fc control (5.2 mg/kg QD), mL4-3 (3.2 mg/kg QD), L1-7(N) (2.0 mg/kg QD), L1-7(N) combined with mL4-3 (at the same dosing regimens used in the single-agent groups), or AMG 386 (5.6 mg/kg twice per week). One of four representative experiments is shown. Data are mean values±SE. *P<0.0001 vs L1-7(N), RMANOVA with Scheffé post hoc test.

Ang1 antagonism augments Ang2 antagonism in suppressing tumor growth. In a previous report, we demonstrated that systemically administered L1-7(N) and AMG 386 were capable of inhibiting the growth of Colo205 tumor xenografts implanted into nude mice. In that study, the antitumor effects of AMG 386 were modestly superior to those of L1-7(N) (P=0.006). To confirm that dual Ang1/Ang2 inhibition confers better tumor growth suppression than Ang2 inhibition alone, a similar experiment was performed, but this time groups treated with mL4-3 or a combination of mL4-3 and L1-7(N) were also tested (FIG. 9). The AMG 386 treatment group and the mL4-3/L1-7(N) combination treatment group showed comparable antitumor efficacy; moreover, both groups exhibited efficacy superior to that mediated by either L1-7(N) or mL4-3 alone. In fact, mL4-3 had no discernable single-agent effect on tumor growth, implying that combining Ang2 antagonism with Ang1 antagonism may have unmasked the antitumor effect of Ang1 inhibition. Additional replicates of these experiments confirmed that AMG 386 and the mL4-3/L1-7(N) combination mediated greater tumor growth suppression than L1-7(N) alone (data not shown). However, in a minority of instances, these differences did not reach statistical significance, perhaps reflecting the subtle nature of the incremental advantage conferred by dual Ang1/Ang2 inhibition over selective Ang2 inhibition. Selective Ang1 inhibition had no antitumor effect on its own in any of the experiments in which it was tested (FIG. 9 and data not shown).

Figure 10:
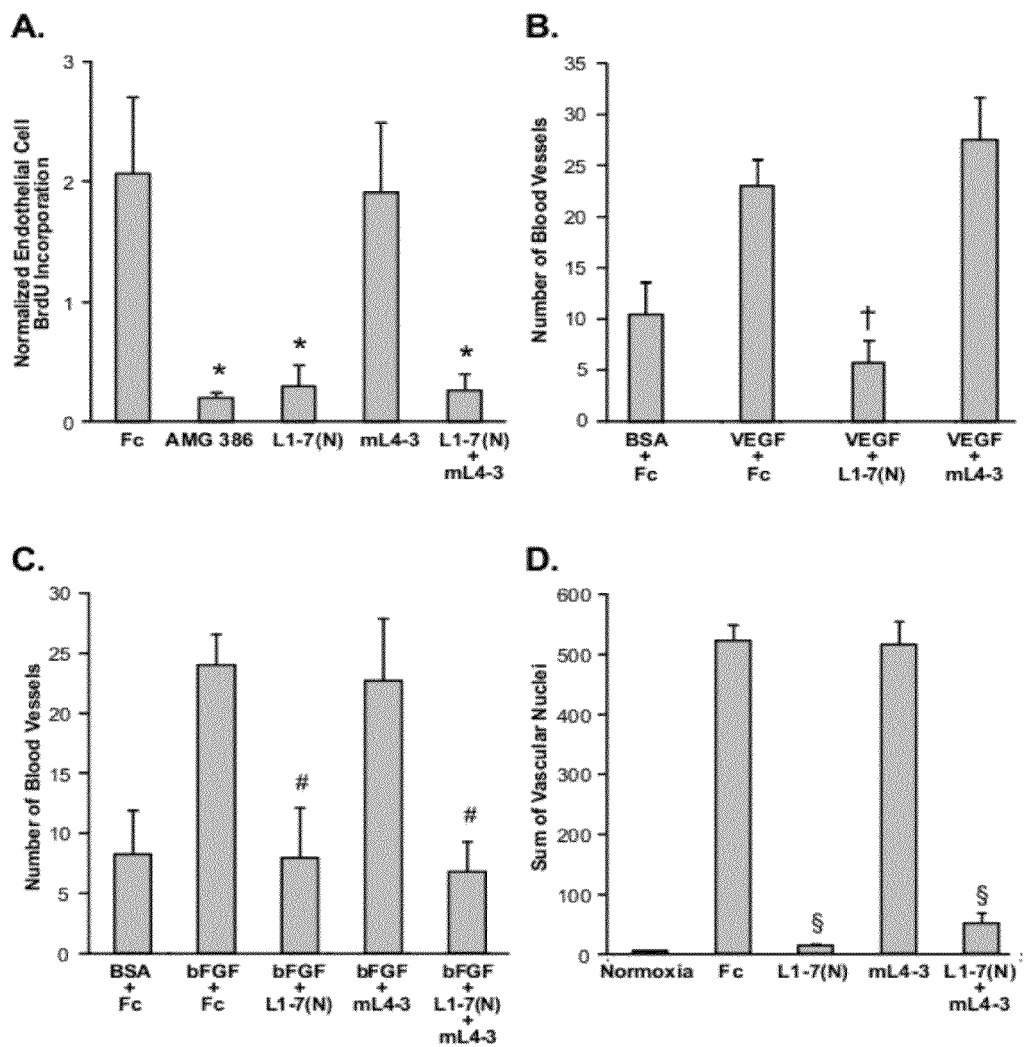
FIG. 10 depicts the effect of Ang1 and Ang2 antagonism on tumor endothelial cell proliferation, corneal angiogenesis, and retinal angiogenesis. A) The effect of inhibition of Ang1 and Ang2 on BrdU uptake in mouse endothelial cells derived from Colo205 tumor xenografts. Tumor-bearing mice were treated for 3 days with Fc (5.7 mg/kg QD), AMG 386 (6 mg/kg single dose), L1-7(N) (2.2 mg/kg QD), mL4-3 (3.5 mg/kg QD), or L1-7(N) combined with mL4-3 (at the same doses and schedules used in the single-agent groups). Each bar represents mean endothelial:total mouse cell BrdU ratios (n=3). Data are mean values±SE. *P<0.05 vs. Fc, unpaired Student's t-test. B and C) The effect of inhibition of Ang1 and Ang2 on (B) VEGF-induced and (C) bFGF-induced corneal angiogenesis. Angiogenesis was induced by implanting VEGF- or bFGF-soaked nylon discs into the corneal stroma of rats (n=8 per group). Treatment was initiated one day prior to corneal implantation and continued every 3 days with: Fc (60 mg/kg), L1-7(N) (5 mg/kg), mL4-3 (60 mg/kg) and L1-7(N) combined with mL4-3 (at the same dose and schedule used in the single-agent groups). Data are mean values±SE. $^†$P<0.0001 vs Fc+VEGF (B); $^\#$P<0.002 vs Fc+bFGF (C), ANOVA with Fisher's post hoc test. D) Inhibition of Ang2 prevents oxygen-induced neovascularization in the mouse retina. Starting on postnatal day P8, pups (n=5 per group) were treated daily s.c. for nine days with Fc (200 mg/kg) L1-7(N) (100 mg/kg) mL4-3 (100 mg/kg) or L1-7(N) combined with mL4-3 (at the same dose and schedule used in the single-agent groups). Data are mean values±SE. $^§$P<0.0001 vs Fc, ANOVA with Fisher's post hoc test.

Ang2 antagonism, but not Ang1 antagonism, inhibits tumor endothelial cell proliferation, corneal angiogenesis, and retinal angiogenesis. We previously showed that dual Ang1/Ang2 inhibition was capable of suppressing Colo205 tumor endothelial cell proliferation in vivo. To investigate whether this effect was conferred through Ang1 inhibition, Ang2 inhibition, or a combination of the two, Colo205 tumor-bearing mice were treated with mL4-3, L1-7(N), mL4-3/L1-7(N), or AMG 386. As with the tumor volume readout described in the previous section, mL4-3 had no single-agent effect on tumor endothelial cell proliferation, while L1-7(N) was inhibitory (FIG. 10A). Curiously, however, dual Ang1/Ang2 inhibition conferred no greater effect on endothelial cell proliferation than Ang2 inhibition alone (FIG. 10A), an observation that has been repeatedly reproduced (data not shown) and stands in contrast to the apparently cooperative effects of combined Ang1/Ang2 inhibition on Colo205 tumor growth. This dissimilarity implies that repression of endothelial cell proliferation is only one component underlying the tumor growth inhibition mediated by angiopoietin antagonism.

These agents were next tested in two models of ocular angiogenesis, one involving the cornea and the other involving the retina. The cornea is normally avascular, but pathological angiogenesis can occur in the cornea secondary to conditions such as keratitis and corneal transplant rejection. VEGF- and basic fibroblast growth factor (bFGF)-induced models of corneal angiogenesis were used to test the roles of Ang1 and Ang2 antagonism in neovessel formation. As observed with endothelial cell proliferation, corneal angiogenesis appeared to be dependent on Ang2, but not on Ang1 (FIGS. 10B and 10C). The same conclusion could be drawn from evaluation of these angiopoietin-antagonizing peptibodies in a Tie2-dependent retinal model of angiogenesis in which neovascularization was induced by changes in ambient oxygen tension (FIG. 10D). Thus, in three preclinical settings (endothelial cell proliferation, corneal angiogenesis, and retinal angiogenesis), Ang2 inhibition dramatically suppressed neovessel formation, while Ang1 inhibition had no effect alone or in combination with Ang2 inhibition.

Selective inhibition of Ang1 or Ang2 induces ovarian atrophy, but not epiphyseal plate thickening. To assess the effects of angiopoietin inhibition in normal animals, rats were treated systemically with mL4-3, L1-7(N), or AMG 386 for one month. AMG 386, like VEGF antagonists, has been observed to induce epiphyseal plate thickening and ovarian atrophy, effects considered to be mechanism-based consequences of antiangiogenic therapy. In the present study, AMG 386 provoked epiphyseal plate thickening in all treated animals, while, remarkably, L1-7(N) and mL4-3 failed to alter epiphyseal morphology in any rats (Table 13). Thus, induction of epiphyseal plate thickening appears to require inhibition of both Ang1 and Ang2. In striking contrast, all three peptibodies produced ovarian atrophy at similar incidence rates, indicating that selective inhibition of Ang1 or Ang2 is sufficient to induce ovarian atrophy.

Figure 11:
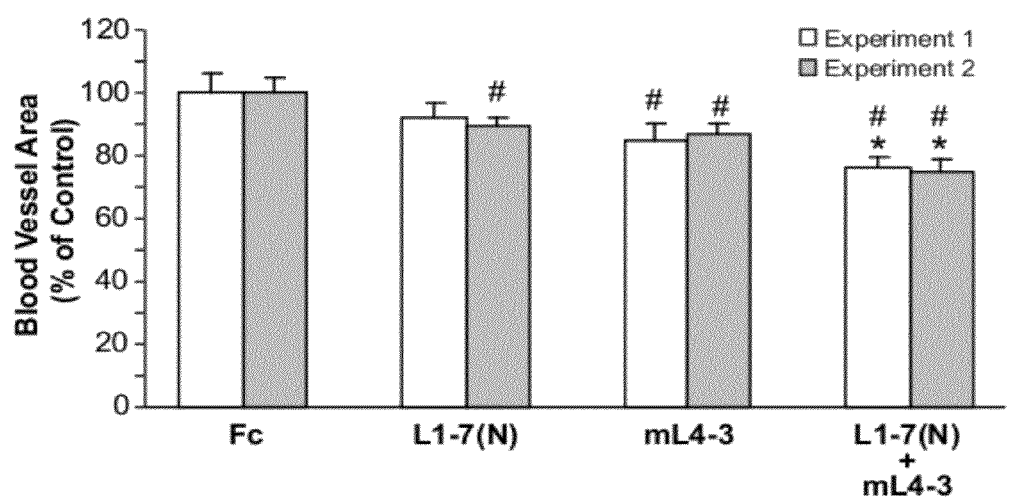
FIG. 11 depicts Ang1 and Ang2 inhibitors cooperatively suppress ovarian follicular angiogenesis. HCG was used to induce superovulation in mice. Fc (300 mg/kg), mL4-3 (150 mg/kg), L1-7(N) (150 mg/kg), or an mL4-3/L1-7(N) combination (150 mg/kg each) administered s.c. (n=7-10 mice per group) were evaluated for the ability to prevent neovascularization in ovulating follicles. Blood vessel area was calculated from anti-CD31 immunostained sections of individual follicles. Data are mean values±SE. Two independent experiments are shown. *P=0.005 comparing mL4-3/L1-7(N) combination vs either single agent alone; $^\#$P<0.05 vs Fc, ANOVA with Dunnett's post hoc test.

Ang1 and Ang2 Inhibitors Cooperatively Suppress Ovarian Follicular Angiogenesis. To better understand the effects of angiopoietin inhibition on the ovary, we employed a hormone-induced model of ovarian follicular angiogenesis that allowed controlled assessment of neovascularization in mice that had never previously ovulated. In this model, pregnant mare serum (PMS) and human chorionic gonadotropin (HCG) were used to induce rapid, synchronized ovulation in multiple follicles (FIG. 11). Mice were treated systemically with Fc control, mL4-3, L1-7(N), or an mL4-3/L1-7(N) combination to determine the effects of these agents on neovessel formation in transforming Graafian follicles. Two identically-designed replicates of this experiment were performed on different days, and remarkably, both yielded almost identical activity profiles with respect to percentage inhibition of blood vessel area (replicate 1, replicate 2): L1-7(N) (8%, 11%), mL4-3 (15%, 14%), mL4-3/L1-7(N) (24%, 26%). All single-agent and combination peptibody groups, with the exception of the L1-7(N) group in Experiment 1, mediated statistically significant inhibition of angiogenesis relative to the Fc control ($P<0.05$) (FIG. 11). Thus, both inhibition of ovarian angiogenesis and induction of ovarian atrophy could be elicited by inhibiting Ang1, Ang2, or both, consistent with the notion that the observed ovarian atrophy was a consequence of failed neovessel development.

We demonstrate that Ang1 inhibition plays a context-dependent role in the suppression of angiogenesis in preclinical disease models and in normal animals. In utero, pharmacologic Ang1 inhibition partially phenocopied the genetic ablation of Ang1, consistent with the important role of Ang1 in developmental angiogenesis. Postnatally, selective Ang1 antagonism inhibited ovarian angiogenesis and induced ovarian atrophy, effects that could also be achieved by inhibiting Ang2 alone or Ang1 plus Ang2 together. However, in postnatal disease models, Ang1 inhibition had little effect on its own, although its biological activity appeared to be unmasked in some settings when combined with Ang2 suppression. The mechanism underlying the differential dependency on Ang1 in these settings remains to be determined.

The ovary, by virtue of its role in reproductive cycling, is one of the few organs that undergoes normal angiogenesis in adults. Based on the ovarian expression patterns of Ang1 and Ang2 in hormone-induced ovulating rats, it has been proposed that Ang2 plays an early role in vessel invasion, and Ang1 plays a later role to mature the newly-formed vessels. Under this hypothesis, Ang2 and Ang1 perform opposing functions, where Ang2 initially displaces Ang1 from Tie2, resulting in vessel destabilization and angiogenesis. This state of plasticity is subsequently reversed when Ang1 ousts Ang2 from the receptor to re-establish vascular quiescence and stability. In conflict with this model, the data from the current study imply that Ang1 and Ang2 both play pro-angiogenic roles in the ovary.

In the Colo205 tumor xenograft model, antagonism of Ang1 and Ang2 mediated greater tumor suppression than was achieved by inhibiting Ang1 or Ang2 individually, indicating that this model is dependent on both angiopoietins. However, in the same model, only Ang2 inhibition was capable of down-modulating tumor endothelial cell proliferation, suggesting that Ang1 is not involved in this function. What accounts for the different dependencies of these two endpoints on Ang1? One possibility is that Ang1 inhibition has a direct effect on tumor cells. This seems unlikely, however, given that AMG 386, a dual inhibitor of Ang1 and Ang2, has no effect on the in vitro growth of cultured Colo205 tumor cells. A second possibility is that Ang1 antagonism plays an anti-angiogenic role that is not conferred through inhibition of endothelial cell proliferation, but instead through mechanisms that might impact functions such as endothelial cell migration or invasion. This explanation could be applicable if Ang1 and Ang2 mediated qualitatively or quantitatively different signals through Tie2, or if Ang1 signaled through additional receptors that were not responsive to Ang2. A third possibility is that Ang1 signals through Tie2 on non-endothelial cells, such as Tie2-expressing monocytes (TEMs). TEMs are recruited to tumors, where they cluster around neovessels. Selective ablation of TEMs in tumor-bearing mice suppresses tumor angiogenesis and inhibits tumor growth, and it has been postulated that TEMs promote tumor angiogenesis by providing paracrine signals that stimulate neovessels. Perhaps Ang1 stimulates TEMs to release pro-angiogenic cytokines other than the angiopoietins. In such a setting, inhibition of Ang1 could have an indirect anti-neovascular effect that might complement the direct anti-angiogenic effect of Ang2 suppression.

In contrast to the subtle and context-dependent effects of Ang1 inhibition, Ang2 inhibition frequently mediated effects that were equivalent or nearly equivalent to those conferred by combined antagonism of Ang1 and Ang2, implying that Ang2 may be the dominant angiopoietin involved in postnatal angiogenesis. Ang1 appears to be the dominant angiopoietin involved in prenatal angiogenesis, suggesting a shift in the dependency on these two factors around the time of birth. Our inhibitors do not antagonize Ang4, but the functional relevance of this factor is unclear, given its lung-restricted expression pattern.

Ang1 and Ang2 have been shown to play both similar and opposing functional roles in various in vitro and in vivo systems. The inability to draw consistent conclusions in this regard across multiple publications may be in part a consequence of the different conditions under which the question was examined. These differences include evaluation of 1) in vitro versus in vivo systems, 2) prenatal versus postnatal angiogenesis, 3) varying vascular beds, 4) pathological versus normal angiogenesis, and 5) gain-of-function versus loss-of-function experimental designs. This final difference may be particularly important, as the addition of exogenous factors to a model system may be a less physiologically relevant means to elucidate function than removal of endogenous factors. Perhaps the most informative published experiments in this regard are those in which Ang1 and Ang2 have been genetically deleted in the germline of rodents. These studies provide significant insight into the developmental roles of Ang1 and Ang2. However, it is more difficult to genetically examine the postnatal in vivo function of Ang1 and Ang2 without the availability of conditional knockout systems; the constitutive Ang1 knockout mouse dies in utero (as does the constitutive Ang2 knockout on some strain backgrounds), and the postnatal phenotype of surviving Ang2 knockout mice may be influenced by residual effects of developmental gene deletion. By using pharmacologic Ang1 and Ang2 inhibitors to examine the postnatal roles of Ang1 and Ang2 in vivo, we have circumvented these issues. The results of the current study imply that Ang1 and Ang2 do not functionally oppose one another in postnatal systems, and in some cases, they appear to act cooperatively.

Pathological angiogenesis is associated with altered angiopoietin levels in a number of diseases, including cancer, diabetic retinopathy, macular degeneration, rheumatoid arthritis, osteoarthritis, and psoriasis. Angiopoietin-targeted interventions in these therapeutic indications may provide clinical benefit. The data presented herein suggest that, in some settings, combined inhibition of Ang1 and Ang2 may provide superior therapeutic efficacy to that mediated by targeting Ang2 alone.

Methods

Phage display selection of Ang1-binding peptides. Three filamentous phage libraries, TN8-IX ($5 \times 10^9$ independent transformants), TN12-I ($1.4 \times 10^9$ independent transformants), and Linear ($2.3 \times 10^9$ independent transformants) (Dyax Corp., Cambridge, Mass.), were used to select for Ang1-binding phage. After negative selection on empty streptavidin Dynabeads (Invitrogen Corporation, Carlsbad, Calif.) blocked with 2% bovine serum albumin (BSA) or beads loaded with biotinylated Ang2 (R&D Systems, Inc., Minneapolis, Minn.), remaining phage were incubated with beads loaded with biotinylated Ang1 (R&D Systems, Inc.). After extensive washing, the phage from each round of selection were eluted in a nonspecific manner using 100 mM triethylamine solution (Sigma-Aldrich Inc., St. Louis, Mo.). The eluted phage were amplified in E. coli strain XL-1 Blue MRF', purified by precipitation, and then used for the next round of selection.

After three rounds of selection, individual phage clones were isolated and analyzed by phage ELISA and DNA sequencing. Briefly, Ang1 protein was coated on 96-well Maxisorp plates (Nunc brand, Thermo Fisher Scientific, Rochester, N.Y.) and blocked with PBST (PBS with 0.05% Tween-20) containing 4% dry milk. Phage supernatants were incubated in the wells and bound phage were detected with an HRP-conjugated anti-M13 antibody (Amersham Pharmacia Biotech, Piscataway, N.J.). To check cross-reactivity to Ang2 or streptavidin, control plates were set up in a similar fashion. ELISA results and DNA sequencing data were used as criteria for selecting peptide sequences to express in a peptibody format. Peptibodies were evaluated in an HTRF assay, and several were chosen for affinity maturation.

Peptide affinity maturation was performed by generating and panning nucleotide-doped phage display libraries. Libraries with over $1 \times 10^9$ independent transformants were obtained. These focused libraries were panned by a procedure similar to that used for panning the primary libraries.

Peptibody expression and purification. Peptibody mL4-3 was expressed and purified as described in Oliner, J., et al. 2004., *Cancer Cell* 6:507-516. The amino acid sequence of mL4-3 is as follows, where Fc in bold italics denotes the human IgG1 Fc sequence as described previously in Oliner, J., et al. 2004., *Cancer Cell* 6:507-516:

(SEQ ID NO: 47)
MREWTEEMQVIFDAMMFGPRNDRGGSGSATGSGSTASSGSGSATHRE

WTEEMQVIFDAMMFGPRNDRGGGG-*Fc*

The amino acid sequence of the Fc portion of the peptibody mL4-3 is as follows (from amino terminus to carboxyl terminus):

(SEQ ID NO: 48)
DKTHTCPPCPAPELLGGPSVFLFPPKPKDTLMISRTPEVTCVVVDV

SHEDPEVKFNWYVDGVEVHNAKTKPREEQYNSTYRVVSVLTVLHQD

WLNGKEYKCKVSNKALPAPIEKTISKAKGQPREPQVYTLPPSRDEL

TKNQVSLTCLVKGFYPSDIAVEWESNGQPENNYKTTPPVLDSDGSF

FLYSKLTVDKSRWQQGNVFSCSVMHEALHNHYTQKSLSLSPGK

Angiopoietin: Tie2 neutralization HTRF assay. Europium-labeled streptavidin (LANCE reagent, PerkinElmer Inc., Boston, Mass.) and biotinylated human Ang1 (R&D Systems, Inc.) or Ang2 were mixed in HTRF buffer (50 mM Tris-HCl, pH 7.5, 100 mM NaCl, 0.05% Tween 20, 0.1% BSA) and incubated at room temperature in the dark for 30 minutes on a shaker. Equal volumes of the above mixture and serially diluted peptibodies or Fc were mixed and incubated for 1 hour at room temperature. Equal volumes of allophycocyanin-conjugated Tie2-Fc (Tie2-APC) (Prozyme, San Leandro, Calif.) and the above mixture were mixed and incubated for 2 hours at room temperature. The final concentrations of reagents in the assay were 4 nM europium-streptavidin, 2 nM biotinylated Ang1 or Ang2, and 5 nM Tie2-APC. Peptibodies were serially diluted from 10,000 nM to 0.5 nM or 100 nM to 0.005 nM to generate full titration curves. Neutralization of angiopoietin:Tie2 interaction was measured by the diminishing energy transfer between APC and europium and was quantified using a Rubystar plate reader (BMG Labtechnologies, Offenberg, Germany). The potency of angiopoietin/Tie2 neutralization was determined by calculating the percentage inhibition of each peptibody dilution in reference to the maximum (no angiopoietin in the assay mixture) and minimum inhibition (no peptibody in the assay mixture) controls. $IC_{50}$ values were calculated by plotting percentage inhibition using XLfit4, where fit=A+((B−A)/(1+((C/X)^D))) (IDBS, Guildford, UK).

Angiopoietin: Tie2 neutralization ELISA. Ninety-six-well microtiter plates were coated with a panel of recombinant angiopoietins in 293T cell conditioned media (DMEM/50 ug/ml BSA) at 37° C. for 1 hour. The conditioned media were used at angiopoietin concentrations that conferred 70% of maximally achievable binding to 1 nM hTie2-Fc (Recombinant hTie2-Fc, Catalog #313-TI, R&D Systems Inc.). Plates were washed three times with PBS/0.1% Tween-20 and then block for 2 hours at room temperature with PBS/5% BSA. The blocking solution was removed without washing the plates. mL4-3 or Fc serially diluted in a solution of 1 nM Tie2-Fc/1% BSA/PBS was added to the angiopoietin-coated plates, which were incubated overnight at room temperature and then washed with PBS/1% Tween-20. A mouse-derived anti-Tie2 antibody (Catalog #557039, BD Pharmingen Inc., San Jose, Calif.) was added to each well at a final concentration of 1 ug/ml and incubated for 1 hour at room temperature. Plates were then washed 3 times with PBS/0.1% Tween-20. Goat anti-mouse-IgG-HRP (Horseradish peroxidase-conjugated goat anti-mouse antibody, Catalog #31432, Pierce, Rockford, Ill.) was added at a dilution of 1:10,000 in PBS/1% BSA to each well and the plates were incubated for 1 hour at room temperature. Plates were washed three times with PBS/0.1% Tween-20 before TMB substrate (SureBlue Reserve TMB, Catalog #53-00002, KPL, Gaithersburg, Md.) was added and optical density at 650 nM was measured on a plate reader (SpectraMax, Molecular Devices, Sunnyvale, Calif.). The degree of angiopoietin:Tie2 neutralization ($IC_{50}$) was determined by comparison against a Tie2 standard curve (the binding activity of serially diluted Tie2 in the absence of competitor) using XLfit.

Animal studies. All procedures were approved by the Amgen Animal Care and Use Committee and met Association for Assessment and Accreditation of Laboratory Animal Care standards.

Pharmacokinetic assessment. Three CD-1 mice received a single s.c. injection of 3.2 mg/kg of mL4-3, and two Sprague-Dawley rats received a single i.v. injection of 10 mg/kg of mL4-3. Blood samples were collected up to 274 hours from the mice and 336 hours from the rats for serum pharmacokinetic assessment. mL4-3 concentrations in serum samples from each species were measured by an enzyme-linked immunosorbent assay (ELISA). Polystyrene 96-well plates were coated with human Ang1, followed by incubation with mL4-3-containing serum samples. After washing away any unbound substances, a horseradish peroxidase-labeled monoclonal mouse anti-IgG1 antibody was added to the wells. Following a wash step to remove any unbound monoclonal antibody, TMB-peroxidase substrate was added to the wells. The optical density units measured at 450-650 nm were converted to concentrations by comparing to a concurrently analyzed standard curve.

Pharmacokinetic parameters were calculated by noncompartmental analysis of the individual serum concentration-time data (WinNonlin Professional, version 3.3; Pharsight Corp, Mountain View, Calif.). Terminal phase half-life ($t_{1/2}$) was calculated as $t_{1/2}=\ln(2)/\lambda_z$, in which $\lambda_z$ is the first-order terminal phase elimination rate constant estimated via linear regression of the terminal log-linear decay phase. Area under the serum concentration-time curve ($AUC_{0-last}$) was estimated by the linear/log trapezoidal method from time 0 to the time of the last quantifiable concentration ($C_{last}$). $AUC_{0-inf}$ was estimated from time 0 to infinity as $AUC_{0-inf}=AUC_{0-last}+C_{last}/\lambda_z$. $AUC_{0-inf}$ values were normalized to a 1 mg/kg dose.

Because the pharmacokinetic properties of mL4-3, L1-7, and AMG 386 were dissimilar, the dose levels and schedules of each agent were chosen, where possible, to achieve equimolar serum steady-state $C_{min}$ concentrations within pharmacology studies.

Administration of mL4-3 to pregnant mice. Two groups of six 129/SV female mice were impregnated by C57BL/6 males. Pregnant females were dosed with 300 mg/kg Fc control or mL4-3 by s.c. administration on gestational days E4.5, E7.5 and E11.5. Conceptuses (embryos and placentae) were removed on day E12.5, evaluated for gross abnormalities, and fixed by immersion in IHC-zinc (mL4-3-treated, n=10; Fc control-treated, n=10) or Bouin's solution (mL4-3-treated, n=5; Fc control-treated, n=6). Paraffin-embedded tissues were step-sectioned at 50-µm intervals through the heart (embryos in both longitudinal and transverse orientation) and the middle of the placenta. Serial sections from each interval were stained with hematoxylin and eosin (H&E) or stained with a conventional indirect immunohistochemistry procedure using polyclonal anti-CD31 (rat anti-mouse monoclonal MEC 13.3, BD Biosciences Pharmingen, San Diego, Calif.) to specifically label blood vessels. Criteria for scoring changes were established by evaluating sections with a foreknowledge of the treatment. Subsequently, lesion severity was graded rapidly using a tiered scale (minimal, mild, moderate, or marked) and a blinded analytical paradigm. These ordinal pathology data were analyzed using the Chi-square test contained in the JMP statistical software package (v.5.1; SAS Institute Inc., Cary, N.C.). An embryo from each pregnant mother collected on day E12.5 was analyzed by ELISA using human Ang1 as a capture reagent and horseradish peroxidase-labeled monoclonal mouse anti-IgG1 antibody as a detection reagent.

Tie2 phosphorylation assay. The effect of the selective angiopoietin inhibitors on Ang1-induced Tie2 phosphorylation in mouse lungs was performed as described in Hodous, B. L., et al. 2007., *J. Med. Chem.* 50:611-626). Briefly, CD-1 nude mice (Charles River Laboratories, Wilmington, Mass.) were treated s.c. once daily for 23 days with Fc control (20 mg/kg), mL4-3 (20 mg/kg) or L1-7(N) (2 mg/kg). Mice (n=3 per group) were then administered 12 μg by i.v. injection of recombinant Ang1 (R&D Systems Inc.). Fifteen minutes later, mouse lungs were harvested, and the levels of phosphorylated Tie2 were determined by immunoprecipitation-Western blot analysis. Statistical analysis was performed using analysis of variance (ANOVA) followed by Fisher's post hoc test using StatView 5.0.1 software (SAS Institute Inc.). Results are expressed as mean±standard error (SE).

Tumor xenograft models. Eight- to 10-week old female CD1 nude mice (Charles River Laboratories) were used in all experiments. Mice were injected s.c. with $2\times10^6$ Colo205 cells in one-third volume Matrigel (BD Biosciences, San Jose, Calif.). Peptibodies or Fc control were administered by s.c. injection once tumors were established. AMG 386 was dosed twice per week; the other peptibodies and Fc control were dosed once daily. Where necessary, Fc control protein was added to the treatment groups to match the total amount of protein delivered in the combination group (5.2 mg/kg). Tumor measurements and body weights were recorded twice per week. All tumor studies were performed in a blinded fashion. Tumor volume was calculated as length×width×height in $mm^3$ Results are expressed as mean±SE. Statistical analysis was performed using repeated measures analysis of variance followed by a Scheffé post hoc test using StatView 5.0.1 software (SAS Institute Inc.).

Tumor endothelial cell proliferation assay. Tumor endothelial cell proliferation was assayed as previously described (Oliner, J., et al. 2004., Cancer Cell 6:507-516). Briefly, Colo205 tumor-bearing mice were treated systemically with peptibodies for 72 hours and implanted with osmotic pumps containing 3 mg/mL BrdU 16 hours prior to euthanasia. Tumors were harvested, dissociated, fixed, and stained to allow determination of BrdU incorporation in tumor endothelial cells. Statistical analysis was performed using an unpaired t-test.

Corneal angiogenesis model. VEGF and bFGF-induced angiogenesis studies were performed in female CD rats (n=8 per group) as described in Coxon, A., et al. *Arthritis Rheum* 46:2604-2612, 2002 Inhibition of interleukin-1 but not tumor necrosis factor suppresses neovascularization in rat models of corneal angiogenesis and adjuvant arthritis. Treatment with Fc (60 mg/kg), L1-7(N) (5 mg/kg), mL4-3 (60 mg/kg), or the combination of L1-7(N) and mL4-3 (at the same doses used in the single-agent groups) was initiated on the day prior to surgery and continued on day 3 and day 6. On day 8 the study was terminated and the corneas were photographed, as described (Oliner, J., et al. 2004., Cancer Cell 6:507-516). For each corneal image, the number of blood vessels intersecting the midpoint between the implanted disc and the limbus was counted. All evaluations were performed in a blinded fashion. Statistical significance was assessed by ANOVA followed by Fisher's post hoc test.

Retinal neovascularization. Ischemic retinopathy was produced in C57BL/6J mice using the method described by Smith et al., *Invest. Ophthalmol V is Sci* 35: 101-111, 1994. Postnatal day seven (P7) pups and their mothers were placed in a hyperoxic chamber (75±0.5% oxygen) for 5 days and then returned to room air for an additional 5 days (n=7 pups per group). Chamber temperature was maintained between 20° C. and 22° C., and oxygen was constantly controlled by an oxygen control unit (ProOx Model P110 coupled to an oxygen sensor Model E702 Biospherix Ltd, Redfield, N.Y.). One cage with P7 pups remained at room air (normoxia condition). Fc control (200 mg/kg), mL4-3 (100 mg/kg), L1-7(N) (100 mg/kg), or mL4-3/L1-7(N) combination (100 mg/kg each) was administered s.c. once daily for nine days starting on P8. From P8 to P11 the injections were administered using ports to gain access into the chamber. On P17 the pups were sacrificed and their eyes removed and fixed using Davidson's fixative. The eyes were then processed into paraffin using standard methods. Step sections were cut parallel to the optical axis at 100-1 μm intervals. The blocks were completely through-sectioned, resulting in 15 or 16 sections per eye. All sections were stained with H&E. Of the 15 or 16 slides in the step-section series, the middle 10 consecutive slides were used in the analyses, bracketing either side of the optical axis. For each section, the number of vascular nuclei (both endothelial and pericyte nuclei) that were on the vitreous side of the inner limiting membrane were counted. The individual slide counts were recorded and all ten section counts summed for each animal. Five mice in each study group were counted. All counts were performed in a blinded fashion, without knowledge of treatment conditions. Statistical analysis was performed by ANOVA followed by Fisher's post hoc test.

Ovarian follicular angiogenesis. Superovulation was induced in study mice using standard methodology. Briefly, four-week old female C57BL/6J mice were injected with 5-7 IU PMS, effectively resetting the estrus cycle. Forty-eight hours later, the mice were injected with 5 IU of HCG to induce superovulation. The females were then faux-bred and remained on study for 24 hours. Study mice were treated with peptibodies twice per day. Dosing commenced at the time of the initial PMS injection and continued for two consecutive days, with the fourth dose given concurrently with the HCG injection. Mice were euthanized 48 hours following the HCG injection. Right and left ovaries were removed and immersion-fixed in cold zinc tris solution. After 48 hours, ovaries were transferred to 70% ethanol and processed to paraffin using standard methods. Two sequential sections were cut from each ovary pair and individually stained either with H&E or immunostained for vascular endothelium (CD31, rat anti-mouse monoclonal MEC 13.3, BD Biosciences Pharmingen) using DAB as the chromogen. Additionally, the anti-CD31 IHC sections were lightly counterstained with hematoxylin. The individual follicles selected for analysis were identified based on transformational state. This was determined by treatment-blind inspection of the H&E sections under low power. Corresponding images of ten transformed follicles per animal, where feasible, were then captured at 10× objective magnification from the anti-CD31 immunostained sections. The follicle section area was delineated as a ROI, and the CD31-positive area fraction was determined via RGB thresholding using MetaMorph image analysis software (MetaMorph v6.1, UIC, Downingtown, Pa.). Statistical analysis was performed by ANOVA followed by Dunnett's post hoc test.

Evaluation of normal tissues in treated rats. Peptibodies were evaluated in Sprague-Dawley rats (Charles River Laboratories) for effects on normal tissues Animals received 300 mg/kg of AMG 386, L1-7(N) or mL4-3 IV twice weekly for 28 days (n=10 animals per group). At scheduled necropsy, a full tissue set was sectioned, stained, and observed for microscopic changes.

TABLE 10

Peptibodies competitively inhibit angiopoietin: Tie2 interactions

| Agent | hAng1 $IC_{50}$ (nM) | hAng2 $IC_{50}$ (nM) |
|---|---|---|
| L1-7(N) | >10,000 | 0.064 |
| mL4-3 | 0.022 | 3085 |
| AMG 386 | 6.2 | 0.029 |
| Fc | >10,000 | >10,000 | h, human

TABLE 11 mL4-3 selectively neutralizes Ang1:Tie2 interactions

| Agent | hAng1 IC$_{50}$ (nM) | mAng1 IC$_{50}$ (nM) | rAng1 IC$_{50}$ (nM) | cAng1 IC$_{50}$ (nM) | hAng2 IC$_{50}$ (nM) | mAng2 IC$_{50}$ (nM) | cAng2 IC$_{50}$ (nM) |
|---|---|---|---|---|---|---|---|
| mL4-3 | 0.045 | 0.033 | 0.061 | 0.039 | 1876 | >10,000 | 1890 |
| Fc | >10,000 | >10,000 | >10,000 | >10,000 | >10,000 | >10,000 | >10,000 | h, human;
m, mouse;
r, rabbit;
c, cynomolgus monkey

TABLE 12

Mean pharmacokinetic parameters of angiopoietin inhibitors in mice and rats

| | Mouse | | Rat | |
|---|---|---|---|---|
| Agent | $t_{1/2}$ (hr) | Dose-normalized AUC$_{0\text{-}inf}$ (μM · hr/mg/kg) | $t_{1/2}$ (hr) | Dose-normalized AUC$_{0\text{-}inf}$ (μM · hr/mg/kg) |
| mL4-3 | 45 | 5.0 | 42 | 3.6 |
| L1-7(N)[a] | 56 | 7.0 | 47 | 4.6 |
| AMG 386[a] | 97 | 15 | 85 | 8.7 |

[a] Adapted from Oliner et al (18).

TABLE 13

Selective inhibition of Ang1 or Ang2 induces ovarian atrophy, but not epiphyseal plate thickening

| Agent | Epiphyseal plate thickening (males) | Epiphyseal plate thickening (females) | Ovarian atrophy |
|---|---|---|---|
| AMG 386 | 10 | 10 | 8 |
| L1-7(N) | 0 | 0 | 8 |
| mL4-3 | 0 | 0 | 6 | n = 10 per group

What is claimed is:

1. A method of inhibiting undesired angiogenesis that comprises administering to a subject in need thereof, an effective amount of an isolated monoclonal antibody which comprises a heavy chain variable domain and a light chain variable domain, wherein said heavy chain comprises 3 CDRs and said light chain comprises 3 CDRs, wherein the sequences of said CDRs of said antibody are selected from the group consisting of:
    (a) SEQ ID NOs: 18, 26, 32 of the HC plus SEQ ID NOs: 19, 27, 33 of the LC,
    (b) SEQ ID NOs: 18, 26, 34 of the HC plus SEQ ID NOs: 19, 27, 33 of the LC,
    (c) SEQ ID NOs: 18, 26, 35 of the HC plus SEQ ID NOs: 20, 27, 36 of the LC,
    (d) SEQ ID NOs: 18, 26, 37 of the HC plus SEQ ID NOs: 19, 27, 33 of the LC,
    (e) SEQ ID NOs: 18, 26, 38 of the HC plus SEQ ID NOs: 19, 27, 33 of the LC,
    (f) SEQ ID NOs: 18, 26, 35 of the HC plus SEQ ID NOs: 19, 27, 33 of the LC,
    (g) SEQ ID NOs: 18, 26, 34 of the HC plus SEQ ID NOs: 21, 27, 33 of the LC,
    (h) SEQ ID NOs: 18, 28, 39 of the HC plus SEQ ID NOs: 19, 27, 33 of the LC,
    (i) SEQ ID NOs: 18, 26, 34 of the HC plus SEQ ID NOs: 22, 27, 33 of the LC,
    (j) SEQ ID NOs: 18, 26, 32 of the HC plus SEQ ID NOs: 22, 27, 33 of the LC,
    (k) SEQ ID NOs: 18, 29, 39 of the HC plus SEQ ID NOs: 19, 27, 33 of the LC,
    (l) SEQ ID NOs: 18, 26, 34 of the HC plus SEQ ID NOs: 23, 27, 33 of the LC,
    (m) SEQ ID NOs: 18, 26, 35 of the HC plus SEQ ID NOs: 20, 27, 40 of the LC,
    (n) SEQ ID NOs: 18, 26, 32 of the HC plus SEQ ID NOs: 21, 27, 33 of the LC,
    (o) SEQ ID NOs: 18, 26, 35 of the HC plus SEQ ID NOs: 24, 27, 33 of the LC,
    (p) SEQ ID NOs: 18, 26, 35 of the HC plus SEQ ID NOs: 21, 27, 33 of the LC,
    (q) SEQ ID NOs: 18, 26, 35 of the HC plus SEQ ID NOs: 23, 27, 33 of the LC,
    (r) SEQ ID NOs: 18, 26, 34 of the HC plus SEQ ID NOs: 20, 30, 33 of the LC,
    (s) SEQ ID NOs: 18, 26, 34 of the HC plus SEQ ID NOs: 25, 27, 33 of the LC,
    (t) SEQ ID NOs: 18, 26, 35 of the HC plus SEQ ID NOs: 20, 30, 33 of the LC,
    (u) SEQ ID NOs: 18, 26, 34 of the HC plus SEQ ID NOs: 20, 27, 40 of the LC, and
    (v) SEQ ID NOs: 18, 26, and 34 of the HC plus SEQ ID NOs: 20, 31, and 33 of the LC;
wherein said antibody specifically binds to at least one of Ang1 and Ang2 ligands of Tie 2 receptor.

2. A method of inhibiting undesired angiogenesis that comprises administering to a subject in need thereof, an effective amount of an isolated monoclonal antibody which comprises a heavy chain variable domain and a light chain variable domain, wherein said heavy chain variable domain comprises 3 CDRs having the sequences given in SEQ ID NOs: 18, 26, 35 and said light chain variable domain comprises 3 CDRs having the sequences given in SEQ ID NOs: 23, 27, 33, wherein said antibody specifically binds to at least one of Ang1 and Ang2 ligands of Tie 2 receptor.

3. A method of inhibiting undesired angiogenesis that comprises administering to a subject in need thereof, an effective amount of an isolated monoclonal antibody that specifically binds to at least one of Ang1 and Ang2 ligands of Tie 2 receptor, wherein said antibody comprises a heavy chain variable domain having the sequence given in SEQ ID NO: 3 and a light chain variable domain having the sequence given in SEQ ID NO: 10.

4. A method of inhibiting endothelial cell proliferation that comprises administering to a subject in need thereof, an effective amount of an isolated monoclonal antibody which comprises a heavy chain variable domain and a light chain variable domain, wherein said heavy chain comprises 3 CDRs and said light chain comprises 3 CDRs, wherein the sequences of said CDRs of said antibody are selected from the group consisting of:
    (a) SEQ ID NOs: 18, 26, 32 of the HC plus SEQ ID NOs: 19, 27, 33 of the LC,
    (b) SEQ ID NOs: 18, 26, 34 of the HC plus SEQ ID NOs: 19, 27, 33 of the LC,
    (c) SEQ ID NOs: 18, 26, 35 of the HC plus SEQ ID NOs: 20, 27, 36 of the LC,
    (d) SEQ ID NOs: 18, 26, 37 of the HC plus SEQ ID NOs: 19, 27, 33 of the LC,
    (e) SEQ ID NOs: 18, 26, 38 of the HC plus SEQ ID NOs: 19, 27, 33 of the LC,
    (f) SEQ ID NOs: 18, 26, 35 of the HC plus SEQ ID NOs: 19, 27, 33 of the LC,
    (g) SEQ ID NOs: 18, 26, 34 of the HC plus SEQ ID NOs: 21, 27, 33 of the LC,
    (h) SEQ ID NOs: 18, 28, 39 of the HC plus SEQ ID NOs: 19, 27, 33 of the LC,
    (i) SEQ ID NOs: 18, 26, 34 of the HC plus SEQ ID NOs: 22, 27, 33 of the LC,
    (j) SEQ ID NOs: 18, 26, 32 of the HC plus SEQ ID NOs: 22, 27, 33 of the LC,
    (k) SEQ ID NOs: 18, 29, 39 of the HC plus SEQ ID NOs: 19, 27, 33 of the LC,
    (l) SEQ ID NOs: 18, 26, 34 of the HC plus SEQ ID NOs: 23, 27, 33 of the LC,
    (m) SEQ ID NOs: 18, 26, 35 of the HC plus SEQ ID NOs: 20, 27, 40 of the LC,
    (n) SEQ ID NOs: 18, 26, 32 of the HC plus SEQ ID NOs: 21, 27, 33 of the LC,
    (o) SEQ ID NOs: 18, 26, 35 of the HC plus SEQ ID NOs: 24, 27, 33 of the LC,
    (p) SEQ ID NOs: 18, 26, 35 of the HC plus SEQ ID NOs: 21, 27, 33 of the LC,
    (q) SEQ ID NOs: 18, 26, 35 of the HC plus SEQ ID NOs: 23, 27, 33 of the LC,
    (r) SEQ ID NOs: 18, 26, 34 of the HC plus SEQ ID NOs: 20, 30, 33 of the LC,
    (s) SEQ ID NOs: 18, 26, 34 of the HC plus SEQ ID NOs: 25, 27, 33 of the LC,
    (t) SEQ ID NOs: 18, 26, 35 of the HC plus SEQ ID NOs: 20, 30, 33 of the LC,
    (u) SEQ ID NOs: 18, 26, 34 of the HC plus SEQ ID NOs: 20, 27, 40 of the LC, and
    (v) SEQ ID NOs: 18, 26, and 34 of the HC plus SEQ ID NOs: 20, 31, and 33 of the LC;
wherein said antibody specifically binds to at least one of Ang1 and Ang2 ligands of Tie 2 receptor.

5. A method of inhibiting endothelial cell proliferation that comprises administering to a subject in need thereof, an effective amount of an isolated monoclonal antibody which comprises a heavy chain variable domain and a light chain variable domain, wherein said heavy chain variable domain comprises 3 CDRs having the sequences given in SEQ ID NOs: 18, 26, 35 and said light chain variable domain comprises 3 CDRs having the sequences given in SEQ ID NOs: 23, 27, 33, wherein said antibody specifically binds to at least one of Ang1 and Ang2 ligands of Tie 2 receptor.

6. A method of inhibiting endothelial cell proliferation that comprises administering to a subject in need thereof, an effective amount of an isolated monoclonal antibody that specifically binds to at least one of Ang1 and Ang2 ligands of Tie 2 receptor, wherein said antibody comprises a heavy chain variable domain having the sequence given in SEQ ID NO: 3 and a light chain variable domain having the sequence given in SEQ ID NO: 10.

7. The any of claims 1-6, wherein said isolated antibody further comprises an IgG heavy constant domain and an IgG light chain constant domain.

8. The any of claims 1-6, wherein said antibody is an IgG.

9. The any of claims 1-6, wherein said antibody is a fully human antibody.

10. The any of claims 1-6, wherein said antibody is in admixture with a pharmaceutically acceptable carrier.

11. The any of claims 1-6, wherein said undesired angiogenesis is associated with cancer.

12. The any of claims 1-6, further comprising the administration of radiation treatment.

13. The any of claims 1-6, further comprising the administration of a chemotherapeutic agent.

* * * * *

UNITED STATES PATENT AND TRADEMARK OFFICE
Certificate

Patent No. 8,221,749 B2                                                                           Patented: July 17, 2012

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Thomas C. Boone, Newbury Park, CA (US); Jonathan D. Oliner, Newbury Park, CA (US); and Eunkyung Lee, Newbury Park, CA (US).

Signed and Sealed this Fifth Day of February 2013.

MISOOK YU
*Supervisory Patent Examiner*
Art Unit 1642
Technology Center 1600

UNITED STATES PATENT AND TRADEMARK OFFICE
CERTIFICATE OF CORRECTION

| | | |
|---|---|---|
| PATENT NO. | : 8,221,749 B2 | Page 1 of 1 |
| APPLICATION NO. | : 13/194854 | |
| DATED | : July 17, 2012 | |
| INVENTOR(S) | : Boone et al. | |

It is certified that error appears in the above-identified patent and that said Letters Patent is hereby corrected as shown below:

In the Claims

Column 111, Line 12, Claim 7 should read
7. The method of any of claims 1-6, wherein said isolated antibody further comprises an IgG heavy constant domain and an IgG light chain constant domain.

Column 112, Line 1, Claim 8 should read
8. The method of any of claims 1-6, wherein said antibody is an IgG.

Column 112, Line 2-3, Claim 9 should read
9. The method of any of claims 1-6, wherein said antibody is a fully human antibody.

Column 112, Line 4-5, Claim 10 should read
10. The method of any of claims 1-6, wherein said antibody is in admixture with a pharmaceutically acceptable carrier.

Column 112, Line 6-7, Claim 11 should read
11. The method of any of claims 1-6, wherein said undesired angiogenesis is associated with cancer.

Column 112, Line 8-9, Claim 12 should read
12. The method of any of claims 1-6, further comprising the administration of radiation treatment.

Column 112, Line 10, Claim 13 should read
13. The method of any of claims 1-6, further comprising the administration of a chemotherapeutic agent.

Signed and Sealed this
Sixth Day of January, 2015

Michelle K. Lee
*Deputy Director of the United States Patent and Trademark Office*